United States Patent
Linnik et al.

(10) Patent No.: US 7,081,242 B1
(45) Date of Patent: Jul. 25, 2006

(54) METHODS OF TREATING LUPUS BASED ON ANTIBODY AFFINITY AND SCREENING METHODS AND COMPOSITIONS FOR USE THEREOF

(75) Inventors: Matthew D. Linnik, Solana Beach, CA (US); Patricia A. McNeeley, San Diego, CA (US)

(73) Assignee: La Jolla Pharmaceutical Company, San Diego, CA (US)

( * ) Notice: Subject to any disclaimer, the term of this patent is extended or adjusted under 35 U.S.C. 154(b) by 0 days.

(21) Appl. No.: 09/724,822

(22) Filed: Nov. 28, 2000

Related U.S. Application Data

(60) Provisional application No. 60/167,716, filed on Nov. 28, 1999.

(51) Int. Cl.
  *A61K 39/385* (2006.01)

(52) U.S. Cl. .................. 424/193.1; 523/23.1; 523/24.1
(58) Field of Classification Search .............. 424/193.1; 523/23.1, 24.1
  See application file for complete search history.

(56) References Cited

U.S. PATENT DOCUMENTS

| | | |
|---|---|---|
| 5,126,131 A | 6/1992 | Dintzis et al. |
| 5,162,515 A | 11/1992 | Conrad et al. |
| 5,268,454 A | 12/1993 | Barstad et al. |
| 5,276,013 A | 1/1994 | Conrad et al. |
| 5,370,871 A | 12/1994 | Dintzis et al. |
| 5,391,785 A | 2/1995 | Jones et al. |
| 5,470,570 A | 11/1995 | Taylor et al. |
| 5,487,890 A | 1/1996 | Taylor et al. |
| 5,552,391 A | 9/1996 | Coutts et al. |
| 5,606,047 A | 2/1997 | Coutts et al. |
| 5,633,395 A | 5/1997 | Coutts et al. |
| 5,726,329 A | 3/1998 | Jones et al. |
| 5,786,512 A | 7/1998 | Jones et al. |
| 5,817,752 A | 10/1998 | Yu |
| 5,856,464 A | 1/1999 | Livingston |
| 5,874,409 A | 2/1999 | Victoria et al. |
| 5,874,552 A | 2/1999 | Jones et al. |
| 5,879,679 A | 3/1999 | Taylor et al. |
| 6,022,544 A | 2/2000 | Dintzis et al. |
| 6,060,056 A | 5/2000 | Coutts et al. |
| 6,207,160 B1 | 3/2001 | Victoria et al. |
| 6,340,460 B1 | 1/2002 | Dintzis |
| 6,362,254 B1 | 3/2002 | Harris et al. |
| 6,375,951 B1 | 4/2002 | Dintzis |
| 6,399,578 B1 | 6/2002 | Jack et al. |
| 6,458,953 B1 | 10/2002 | Jones |
| 6,572,856 B1 | 6/2003 | Taylor et al. |
| 6,858,210 B1 | 2/2005 | Marquis et al. |
| 2001/0010808 A1 | 8/2001 | Yagi et al. |
| 2001/0010818 A1 | 8/2001 | Engle et al. |
| 2002/0082400 A1 | 6/2002 | Coutts et al. |
| 2002/0103343 A1 | 8/2002 | Taylor et al. |
| 2002/0107389 A1 | 8/2002 | Coutts et al. |
| 2002/0110535 A1 | 8/2002 | Jones |
| 2002/0187156 A1 | 12/2002 | Dintizis et al. |
| 2003/0077273 A1 | 4/2003 | Linnik et al. |
| 2003/0103990 A1 | 6/2003 | Coutts et al. |
| 2003/0114405 A1 | 6/2003 | Linnik et al. |
| 2003/0162953 A1 | 8/2003 | Coutts et al. |
| 2004/0208864 A1 | 10/2004 | Strand et al. |
| 2004/0224366 A1 | 11/2004 | Jones et al. |
| 2004/0258683 A1 | 12/2004 | Linnik et al. |
| 2005/0004351 A1 | 1/2005 | Marquis et al. |
| 2005/0026856 A1 | 2/2005 | Coutts et al. |
| 2005/0031635 A1 | 2/2005 | Coutts et al. |

FOREIGN PATENT DOCUMENTS

| | | |
|---|---|---|
| EP | 0 438 259 A1 | 7/1991 |
| EP | 0 642 798 A2 | 3/1995 |
| EP | 0 743 856 | 11/1996 |
| WO | WO 91/10426 | 7/1991 |
| WO | WO 92/05801 | 4/1992 |
| WO | WO 92/13558 | 8/1992 |
| WO | WO 93/02093 | 2/1993 |
| WO | WO 95/07073 | 3/1995 |
| WO | WO 95/22977 | 8/1995 |
| WO | WO 96/40197 | 12/1996 |
| WO | WO 96/40708 | 12/1996 |
| WO | WO 97/46248 | 12/1997 |
| WO | WO 97/46251 | 12/1997 |
| WO | WO 99/40434 A1 | 8/1999 |
| WO | WO 99/64595 | 12/1999 |
| WO | WO 00/15259 | 3/2000 |
| WO | WO 00/33887 | 6/2000 |
| WO | WO 00/34231 | 6/2000 |
| WO | WO 00/34296 | 6/2000 |
| WO | WO 00/75105 | 12/2000 |
| WO | WO 01/41813 | 6/2001 |
| WO | WO 01/45669 | 6/2001 |
| WO | WO 01/80883 | 11/2001 |
| WO | WO 01/93914 | 12/2001 |
| WO | WO 02/46208 | 6/2002 |
| WO | WO 02/092011 | 11/2002 |
| WO | WO 2004/060320 | 7/2004 |

OTHER PUBLICATIONS

Jones et al. Immunospecific Reduction of Antioligonucleotide Antibody Forming Cell with a Tetrakis–oligonucleotide Conjugate, a Therapeutic Candidate for the Treatment of Lupus Nephritis. J. Med. Chem. 1995, vol. 38, No. 12, pp. 2138–2144.*

(Continued)

*Primary Examiner*—David Guzo
*Assistant Examiner*—Celine Qian
(74) *Attorney, Agent, or Firm*—Morrison & Foerster LLP

(57) ABSTRACT

The invention provides methods identifying individuals suitable for treatment for lupus and methods of monitoring treatment, based on measuring antibody affinities, as well as of treating lupus based on measuring antibody affinities. The treatment entails administration of a conjugate comprising a non-immunogenic valency platform molecule and at least two double stranded DNA epitopes, such as DNA molecules, which bind to anti-DNA antibodies from the patient.

64 Claims, 20 Drawing Sheets

OTHER PUBLICATIONS

Bootsma, H. et al. (1995). "Prevention of Relapses in Systematic Lupus Erythematosus", *Lancet*, 345:1595–1599.

Borel, Y. et al. (1990) "A Novel Technique to Link Either Proteins or Peptides to Gammaglobulin to Construct Tolerogens" *J. Immunol. Methods* 126:159–168.

Borel, Y. et al. (1995) "Food Allergens Transformed into Tolerogens" *Int. Arch. Allergy Immunol.* 107:264–267.

Borel, Y. et al. (1996) "Parenteral and Oral Administration of Tolerogens: Protein–IgG Conjugates" *Ann. N.Y. Acad. Sci.* 778:80–87.

Borg, E. J. et al. (1990). "Measurement of Increases in Anti–Double–Stranded DNA Antibody Levels as a Predictor of Disease Exacerbation in Systemic Lupus Erythematosus", *Arthritis Rheumatism.* 33:634–643.

Coutts, S. M. et al. (1996). "Pharmacological Intervention in Antibody Mediated Disease", *Lupus* 5:158–159.

Dintzis, R. Z. et al. (1983). "Studies on the Immunogenicity and Tolerogenicity of T–Independent Antigens", *The Journal of Immunology* 13(5):2196–2203.

Dintzis, R. Z. et al. (1989). "The Immunogenicity of Soluble Haptenated Polymers is Determined by Molecular Mass and Hapten Valence", *The Journal of Immunology* 143:1239–1244.

Dumas, V. et al. (1995). "Induction of Tolerance by Administration of Hapten–Immunoglobin Conjugates is Assoicated with Decreased IL–2 and IL–4 Production", *Arch. Dematol.Res.*, 287:123–128.

Foster, M. H. et al. (1993). "Biology of Disease Nephritogenic Autoantibodies in Systematic Lupus Erythematosus: Immunochemical Properties, Mechanisms of Immune Deposition, and Genetic Origins", *Laboratory Investigation*, 69(5):494–507.

Jones, D. et al. (1994). "Conjugates of Double –Stranded Oligonucleotides with Poly(ethylene glycol) and Keyhole Limpet Hemocyann: a Model for Treating Systematic Lupus Erythematosus", *Bioconjugate Chemistry* 5:390–399.

Jones, D. et al. (1995). "Immunospecific Reduction of Antioligonucleotide Antibody–Forming Cells with a Tetrakis–Oligonucleotide Conjugate (LJP 394), a Therapeutic Candidate for the Treatment of Lupus Nephritis", *J. Med. Chem.* 38:2138–2144.

Morimoto, C. et al. (1982). "A Defect of Immunoregulatory T Cell Subsets in Systematic Lupus Erythematosus Patients Demonstrated with Anti–2H4 Antibody", *The Journal of Immunology* 139:1960–1965.

Plunkett, M. L. et al. (1995). "LJP 394: A Novel Clinical Candidate for the Treatment of Lupus Nephritis", *Lupus* 4:S99.

Seleznick, M. J. et al. (1991). "Variables Associated with Decreased Survival in Systematic Lupus Erythematosus", *Seminars in Arthritis and Rheumatism* 21:73–80.

Sem, D. S. et al. (1999). "Antibody Affinities and Relative Titers in Polyclonal Population: Surface Plasmon Resonance Analysis of Anti–DNA Antibodies", *Archives of Biochemistry and Biophysics* 1:372(1):62–68.

Weisman, M. H. et al. (1997). "Reduction in Circulating dsDNA Antibody Titer after Administration of LJP 394", *The Journal of Rheumatology* 24:314–318.

U.S. Appl. No. 10/748,541, filed Dec. 29, 2003, Strand et al.

U.S. Appl. No. 10/814,555, filed Mar. 30, 2004, Linnik et al.

Ferguson, P. J. et al. (1995). "Antigen–Based Heteropolymers Facilitate, Via Primate Erythrocyte Complement Receptor Type 1, Rapid Erythrocyte Binding of an Autoantibody and Its Clearance From The Circulation in Rhesus Monkeys," *The Journal of Immunology* 155:339–347.

Ferguson, P. J. et al. (1994). "Antigen–Based Heteropolymers (AHP): A Potential Therapeutic to Bind and Clear Autoantibodies Via Erythrocyte (E) CR1," *Arthritis & Rheumatism* 37(9 Suppl.) p. S406, Abstract No. 1467.

Aharoni, A. et al., (1993) "Characterization of a multisubunit human protein which selectively binds single stranded $d(GA)_n$ and $d(GT)_n$ sequence repeats in DNA" *Nucl. Acid. Res.* 21(22):5221–5228.

McNeeley, P.A. (2001). "Pre–treatment affinity for LJP 394 influences pharmacodynamic response in lupus patients," *Lupus* 10:526–532.

Jones, D. et al. (May–Jun. 1999). "Multivalent thioether–peptide conjugates: B cell tolerance of an anti–peptide immune response" *Bioconjugate Chemistry* 10(3):480–488.

Jones, D. et al. (2000). "A Convenient Synthesis of N–(tert-butyloxycarbonyl) Aminooxy Ethers," *Tetrahedron Letters* 41: 1531–1533.

La Jolla Pharmaceutical Company Publication (Jan. 11, 2001) "La Jolla Pharmaceutical announces that in three clinical trials 90% of lupus patients have key antibodies", findings presented at JP Morgan H & Q Healthcare Conference, San Francisco, 3 pages.

U.S. Appl. No. 60/088,656, filed Jun. 9, 1998, Marquis et al.
U.S. Appl. No. 60/103,088, filed Oct. 5, 1998, Marquis et al.
U.S. Appl. No. 60/111,641, Dec. 9, 1998, Jones.
U.S. Appl. No. 60/138,260, filed Jun. 8, 1999, Jones et al.
U.S. Appl. No. 09/328,199, filed Jun. 8, 1999, Marquis et al.
U.S. Appl. No. 09/590,592, filed Jun. 8, 2000, Jones et al.
U.S. Appl. No. 09/877,387, filed Jun. 7, 2001, Jones.

Alarcon–Segovia, D. et al. (2000). SL1 Trial Shows Fewer Renal Flares in LJP 394–Treated Patients with High–Affinity Antibodies to LJP 394:90–05 Trial Results, *Arth. Rheumat.* 43(9 supplement):S272 (abstract 1231).

Furie, R.A. et al. (2001). "Treatment of Systemic Lupus Erythematosus with LJP 394," *J. Rheumatol.* 28:257–265.

Henderson, A.L. et al. (2002). "Concerted Clearance of Immune Complexes Bound to the Human Erythrocyte Complement Receptor: Development of a Heterologous Mouse Model," *J Immunol Methods.* 270(2):183–97.

Lindorfer, M.A. et al. (2001). "A Bispecific dsDNAxmonoclonal Antibody Construct for Clearance of Anti–dsDNA IgG in Systemic Lupus Erythematosus," *J. Immunol. Methods* 248(1–2):125–138.

Linnik, M.D. and Bagin, R.G. (2000), "Effect of LJP 394 on Patients with Greatest Impairment of Renal Function at Baseline in the 90–05 Trial," *Arth. Rheumat.* 43(9 supplement):S241 (abstract 1046).

Linnik, M.D. et al. (2000). "Affinity of Antibodies for LJP 394 Influences Pharmacodynamic Response to LJP 394 in SLE Patients with Positive dsDNA Antibody Titers," *Arth. Rheumat.* 43(9 supplement):S241 (abstract 1045).

Pistiner, M. et al. (1991). "Lupus Erythematosus in the 1980s: A Survey of 570 Patients," *Semin. Arthritis Rehum.* 21(1):55–64.

Strand, V. (2001). "Monoclonal Antibodies and Other Biologic Therapies," *Lupus* 10:216–221.

Wallace, D.J. (2001). "Clinical and Pharmacological Experience with LJP–394," *Expert Opinion of Investigational Drugs* 10(1):111–117.

Alarcó–Segovia, D. et al. (2003). "LJP 394 for the Prevention of Renal Flare in Patients with Systemic Lupus Erythematosus," *Arthritis & Rheumatism* 48(2):442–454.

Craig, M. L. et al. (2000). "Clearance of Anti–Double–Stranded DNA Antibodies," *Arthritis & Rheumatism* 43(10):2265–2275.

Ferguson, P. J. et al. (1995). "Antigen–Based Heteropolymers," *Arthritis & Rheumatism* 38(2):190–200.

Taylor, R. P and Ferguson, P. J. (1995). "Immune Complexes (IC) Bound to Erythrocyte (E) CR1 via Anti–CR1 Mabs are Cleared Simultaneously with Loss of E CR1 in a Concerted Reaction in a Rhesus Monkey Model," Abstract 1000, *Arthritis and Rheumatism* 38(6):S320.

Taylor, R. P. and Ferguson, P. J. (1995). "Primate Erythrocyte (E) Complement Receptor (CR1) as an Anchor Site for Bispecific–Based Therapies to Clear Pathogens or Autoantibodies Safely from the Circulation," *Journal of Hematotherapy* 4:357–362.

Wiseman, A. (Oct. 22, 2002). "La Jolla Pharmaceutical to Complete Enrollment of Phase III Lupus Clinical Trial." Press Release, two pages total.

Wiseman, A. (Feb. 18, 2003). "La Jolla Pharmaceutical Announces Results of Phase III Trial of Riquent™." Press Release, six pages total.

Alarcon–Segovia, D. et al. (2001). "SLE Trial Shows Fewer Renal Flares in LJP 394–Treated Patients with High–Affinity Antibodies to LJP 394:90–05 Trial Results," located at <http://www.ljpc.com/abstracts/abstract_2001_02.html> visited on Dec. 8, 2003. La Jolla Pharmaceutical Co. Abstracts. 1 page.

Alarcon–Segovia, D. et al. (2003). "LJP 394 for the Prevention of Renal Flare in Patients with Systemic Lupus Erythematosus: Results from a Randomized, Double–Blind, Placebo–Controlled Study," located at <http://www.ljpc.com/abstracts/abstract_2003_01.html> visited on Dec. 8, 2003. La Jolla Pharmaceutical Co. Abstracts. 2 pages.

Alarcon–Segovia, D. et al. (2003). "SLE Trial Shows Fewer Renal Flares in LJP 394–Treated Patients with High–Affinity Antibodies to JLP 394:90–05 Trial Results," located at <http://www.ljpc.com/abstracts/abstract_2000_sle_trial.html> visited on Dec. 8, 2003. La Jolla Pharmaceutical Co. Abstracts. 2 pages.

Alarcon–Segovia, D. et al. "SLE Trial Shows Fewer Renal Flares in LJP–394 Treated Patients with High–Affinity Antibodies to LJP–394: 90–05. Trial Results," *Lupus* 10 (Supplement 1):pS272: 1231.

Cardiel, M. (2003). "Randomized, Placebo Controlled, Double–Blind Phase III Clinical Trial for the Evaluation of LJP 394 (Abetimus Sodium) in the Treatment of Patients with SLE who are at Risk for Renal Flare," located at <http://www.ljpc.com/abstracts/abstract_2003_02.html> visited on Dec. 8, 2003. La Jolla Pharmaceutical Co. Abstracts. 2 pages.

Cardiel, M.H. et al. (2003). "Clinical Efficacy Results from a RCT of LJP 394 in SLE Patients with History of Renal Disease," *Arthritis and Rheumatism* 48(9):582–583.

Cardiel, M.H. et al. (2003). "Clinical Efficacy Results from a RCT of LJP 394 in SLE Patients with History of Renal Disease," located at <http://www.ljpc.com/abstracts/abstract_2003_07.html> visited on Dec. 8, 2003. La Jolla Pharmaceutical Co. Abstracts. 2 pages.

Furie, R.A. et al. (2000). "Treatment of Systemic Lupus Erythematosus with LJP 394," located at <http://www.ljpc.com/abstracts/abstract_2001_16.html> visited on Dec. 8, 2003. La Jolla Pharmaceutical Co. Abstracts. 1 page.

Iverson et al. (1998) "A Chemically Defined, Toleragen–Based Approach for Targeting Anti–$\beta_2$–glycoprotein I Antibodies" *Lupus* 7 (Suppl 2): S166–S169.

Iverson et al. (1998) "Anti–$\beta_2$ glycoprotein I ($\beta$2GPI) Autoantibodies Recognize an Epitope on the First Domain of $\beta$2GPI" *Proc Natl Acad Sci USA* 95:15542–15546.

Jones et al. (1998) "Synthesis of a Cyclic–Thioether Peptide which Binds Anti–Cardiolipin Antibodies" *Tetrahedron Letters* 39:6107–6110.

Jones, D. (1991). "Case Study: Lupus Nephritis," *American Nephrology Nurses' Association* 18(3):327–329.

Jones, D. (1994). "A New Oligonucleotide Conjugate for Suppression of Anti–Double Stranded DNA Antibodies," *Abstracts of Papers American Chemical Society* 207(1–2):pBIOT 113.

Kandiah et al. (1998) "Current Insights into the "Antiphospholipid" Syndrome: Clinical, Immunological, and Molecular Aspects" *Advances in Immunology* 70:507–563.

La Jolla Pharmaceutical Co. Press Release. (Mar. 31, 2003). "Results from Two Riquent™ Trials Show Lupus Patients with Sustained Reductions in Antibodies to dsDNA Have Fewer Renal Flares," San Diego, CA. 4 pages.

Linnik, M.D. et al. (2000). "Affinity of Antibodies for LJP 394 Influences Pharmacodynamic Response to LJP 394 in SLE Patients with Positive dsDNA Antibody Titers," *Arthritis and Rheumatism* 43(9):1045.

Linnik, M.D. et al. (2000). "Affinity of Antibodies for LJP 394 Influences Pharmacodynamic Response to LJP 394 in SLE Patients with Positive dsDNA Antibody Titers," located at <http://www.ljpc.com/abstracts/abstract_2000_affinity.html> visited on Dec. 8, 2003. La Jolla Pharmaceutical Co. Abstracts. 2 pages.

Linnik, M.D. et al. (2000). "Effect of LJP 394 on Patients with Greatest Impairment of Renal Function at Baseline in the 90–05 Trial," *Arthritis and Rheumatism* 43(9):1046.

Linnik, M.D. et al. (2000). "Effect of LJP 394 on Patients with Greatest Impairment of Renal Function at Baseline in the 90–05 Trial," located at <http://www.ljpc.com/abstracts/abstract_2000_effect.html> visited on Dec. 8, 2003. La Jolla Pharmaceutical Co. Abstracts. 1 page.

Linnik, M.D. et al. (2000). "Reduction in Anti–dsDNA Antibodies by LJP 394 in Lupus Patients is Influenced by Affinity for the LJP 394 dsDNA Eptiope," located at <http://www.ljpc.com/abstracts/abstract_2000_reduction.html> visited on Dec. 8, 2003. La Jolla Pharmaceutical Co. Abstracts. 2 pages.

Linnik, M.D. et al. (2001). "Affinity of Antibodies for LJP 394 Influences Pharmacodynamic Response to LJP 394 in SLE Patients," located at <http://www.ljpc.com/abstracts/abstract_2001_04.html> visited on Dec. 8, 2003. La Jolla Pharmaceutical Co. Abstracts. 1 page.

Linnik, M.D. et al. (2001). "Affinity of Antibodies for LJP 394 Influences Pharmacodynamic Response to LJP 394 in SLE Patients," *Lupus* 10(Supplement 1):pS52:30.

Linnik, M.D. et al. (2001). "Effect of LJP 394 on SLE Patients with Impaired Renal Function," located at <http://www.ljpc.com/abstracts/abstract_2001_03.html> visited on Dec. 8, 2003. La Jolla Pharmaceutical Co. Abstracts. 1 page.

Linnik, M.D. et al. (2001). "Effect of LJP 394 on SLE Patients with Impaired Renal Function," *Lupus* 10(Supplement 1):pS17:19.

Linnik, M.D. et al. (2001). "Effect of LJP 394 or High Dose Corticosteroids and Cyclophosphamide on Anti–dsDNA Antibodies in SLE Patients," located at <http://www.ljpc.com/abstracts/abstract_2001_09.html> visited on Dec. 8, 2003. La Jolla Pharmaceutical Co. Abstracts. 2 pages.

Linnik, M.D. et al. (2001). "Effect of LJP or High Dose Corticosteroids and Cyclophosphamide on Anti–dsDNA Antibodies in SLE Patients," *Arthritis and Rheumatism* 44(9):S282:1378.

Linnik, M.D. et al. (2002). "Workshop Report on Some New Ideas About the Treatment of Systemic Lupus Erythematosus" *Lupus* 11:793–796.

Linnik, M.D. et al. (2002). "Effect of LJP 394 or High Dose Corticosteroids and Cyclophosphamide on Anti–dsDNA Antibodies in SLE Patients," located at <http://www.ljpc.com/abstracts/abstract_2002_05.html> visited on Dec. 8, 2003. La Jolla Pharmaceutical Co. Abstracts. 2 pages.

Linnik, M.D. et al. (2002). "Effect of LJP 394, High Dose Corticosteroids and Cyclophosphamide (HDCC) on Anti–dsDNA Antibodies in SLE Patients," located at <http://www.ljpc.com/abstracts/abstract_2002_02.html> visited on Dec. 8, 2003. La Jolla Pharmaceutical Co. Abstracts. 1 page.

Linnik, M.D. et al. (2002). "Reduction in Antibodies to dsDNA Using LJP in Dose Ranging Trial in Lupus Patients," located at <http://www.ljpc.com/abstracts/abstract_2002_01.html> visited on Dec. 8, 2003. La Jolla Pharmaceutical Co. Abstracts. 1 page.

Linnik, M.D. et al. (2002). "Workshop Report on Some New Ideas about the Treatment of Systemic Lupus Erythematosus," located at <http://www.ljpc.com/abstracts/abstract_2002_10.html> visited on Dec. 8, 2003. La Jolla Pharmaceutical Co. Abstracts. 1 page.

Linnik, M.D. et al. (2003). "Reductions in Anti–DSDNA Antibodies and Reduced Risk of SLE Renal Flare and Major SLE Flare," located at <http://www.ljpc.com/abstracts/abstract_2003_09.html> visited on Dec. 8, 2003. La Jolla Pharmaceutical Co. Abstracts. 2 pages.

Linnik, M.D. et al. (2003). "SLE Patients with Sustained Reductions in Anti–DSDNA Antibodies Have a Reduced Risk of Renal Flare and Major SLE Flare," located at <http://www.ljpc.com/abstracts/abstract_2003_05.html> visited on Dec. 8, 2003. La Jolla Pharmaceutical Co. Abstracts. 2 pages.

McNeeley, P.A. et al. (2000). "Lupus Patient Pharmacodynamic Response to LJP 394 is Influenced by Pre–Treatment Antibody Affinity for LJP 394," located at <http://www.ljpc.com/abstracts/abstract_2000_pharmaco_response.html> visited on Dec. 8, 2003. La Jolla Pharmaceutical Co. Abstracts. 2 pages.

McNeeley, P.A. et al. (2001). "Pre–Treatment Affinity for LJP 394 Influences Pharmacodynamic Response in Lupus Patients," located at <http://www.ljpc.com/abstracts/abstract_2001_13.html> visited on Dec. 8, 2003. La Jolla Pharmaceutical Co. Abstracts. 1 page.

Morimoto, C. et al. (1982). "Correlation Between Clinical Activity of Systemic Lupus Erythematosus and the Amounts of DNA in DNA/Anti–DNA Antibody Immune Complexes," *J. Immunol*. 139(5):1960–1965.

Morimoti, C. et al. (1987). "A Defect of Immunoregulatory T Cell Subsets in Systematic Lupus Erythematosus Patients Demonstrated with Anti–2H4 Antibody," *J Clin Invest*. 79(3):762–768.

Saffran, D.C. et al. (2002). "Treatment of Antibody–Mediated SLE–Like Disease in Male BXSB Mice with a B–Cell Toleragen Specific for Anti–dsDNA Antibodies," located at <http://www.ljpc.com/abstracts/abstract_2002_04.html> visited on Dec. 8, 2003. La Jolla Pharmaceutical Co. Abstracts. 1 page.

Sem, D.S. et al. (1998). "Structural Characterization and Optimization of Anti–body Selected Phage Library Mimotopes of an Antigen Associated with Autoimmune Recurrent Thrombosis," *Biochemistry* 37(46):16069–16091.

Tumlin, J.A. et al. (2001). "The B–Cell Toleragen LJP–394 Reduces Renal Flares in Patients with Lupus Nephritis: A Prospective Double–Blinded, Placebo Controlled Trial," located at <http://www.ljpc.com/abstracts/abstract_2001_08.html> visited on Dec. 8, 2003. La Jolla Pharmaceutical Co. Abstracts. 2 pages.

Tumlin, J.A. et al. (2001). "The B–Cell Tolerogen LJP–394 Reduces Renal Flares in Patients with Lupus Nephritis: A Prospective, Double–Blinded, Placebo Controlled Trial," *Journal of the American Society of Nephrology* 12:p253A.

Tumlin, J.A. et al. (2003). "Efficacy Results from a RCT of LJP 394 in SLE Patients with History of Renal Disease," located at <http://www.ljpc.com/abstracts/abstract_2003_10.html> visited on Dec. 8, 2003. La Jolla Pharmaceutical Co. Abstracts. 2 pages.

Tumlin, J.A. et al. (2003). "Renal Flare in SLE Patients with Impaired Renal Function in a RCT of LJP 394," located at <http://www.ljpc.com/abstracts/abstract_2003_12.html> visited on Dec. 8, 2003. La Jolla Pharmaceutical Co. Abstracts. 2 pages.

Wallace, D.J. et al. (2003). "Safety Results from a Randomized Controlled Trial (RCT) of LJP 394 in Systemic Lupus Erythematosus (SLE) Patients with a History of Renal Disease," located at <http://www.ljpc.com/abstracts/abstract_2003_06.html> visited on Dec. 8, 2003. La Jolla Pharmaceutical Co. Abstracts. 2 pages.

Wallace, D.J. et al. (2003). "Safety Results from a RCT of LJP 394 in SLE Patients with a History of Renal Disease," located at <http://www.ljpc.com/abstracts/abstract_2003_11.html> visited on Dec. 8, 2003. La Jolla Pharmaceutical Co. Abstracts. 2 pages.

La Jolla Pharmaceutical Company Press Release. (Aug. 2, 2004). "La Jolla Pharmaceutical Reaches Agreement with Cardio–Renal Division of FDA Regarding Phase 4 Trial Design Under Special Protocol Assessment," San Diego, CA, 3 pages.

La Jolla Pharmaceutical Company Press Release. (Oct. 14, 2004). "La Jolla Pharmaceutical Company Receives Letter From FDA About Riquent Program," San Diego, CA, 3 pages.

La Jolla Pharmaceutical Company Press Release. (Nov. 23, 2004). "La Jolla Pharmaceutical Company Provides Update on Riquent Program," San Diego, CA, 3 pages.

La Jolla Pharmaceutical Company Press Release. (Mar. 14, 2005). "La Jolla Pharmaceutical Announes Outcome of Recent FDA Discussions," San Diego, CA, 2 pages.

La Jolla Pharmaceutical Company Press Release. (May 31, 2005). "La Jolla Pharmaceutical Company Provides Update on Riquent," San Diego, CA, 3 pages.

U.S. Appl. No. 09/457,875, filed Jul. 18, 2000, 7 pages.
U.S. Appl. No. 09/766,365, filed Oct. 5, 2001, 5 pages.
U.S. Appl. No. 10/144,391, filed Jan. 14, 2005, 11 pages.
U.S. Appl. No. 10/219,238, filed Feb. 22, 2005, 13 pages.
U.S. Appl. No. 10/846,079, filed May 13, 2004, Victoria et al.
U.S. Appl. No. 10/957,198, filed Oct. 1, 2004, Barsted et al.
U.S. Appl. No. 11/073,332, filed Mar. 4, 2005, Jones.
U.S. Appl. No. 11/073,332, filed Jun. 2, 2005, Engle et al.
U.S. Appl. No. 11/149,779, filed Jun. 10, 2005, Jones.

* cited by examiner

* analysis includes 69 of 114 patients treated with LPJ 394
* analysis includes 14 of 19 lupus flares from drug treated group

* data represents 15 of 19 LJP flares and 14 of 23 placebo flares

* HDCC = First incidence of high dose corticosteroids +/or cyclophosphamide

METHODS OF TREATING LUPUS BASED ON ANTIBODY AFFINITY AND SCREENING METHODS AND COMPOSITIONS FOR USE THEREOF

RELATED APPLICATIONS

This application claims the priority benefit of U.S. provisional application Ser. No. 60/167,716, filed Nov. 28, 1999, which is incorporated by reference in its entirety.

TECHNICAL FIELD

This invention relates to the field of antibody-mediated pathologies such as lupus. More particularly, the invention relates to methods of treating individuals (and selecting individuals for treatment) for lupus based on antibody affinity.

BACKGROUND ART

Systemic lupus erythematosus (SLE) is an autoimmune disease characterized by the production of antibodies to a number of nuclear antigens, including double-stranded DNA (dsDNA). Autoantibodies that react with DNA are believed to play a role in the pathology of SLE and are closely associated with lupus nephritis. See, for example, Morimoto et al. (1982) *J. Immunol.* 139:1960–1965; Foster et al. (1993) *Lab. Invest.* 69:494–507; ter Borg et al. (1990) *Arthritis Rheum.* 33:634–643; Bootsma et al. (1995) *Lancet* 345:1595–1599.

Synthetic double-stranded oligonucleotides (dsON) have been shown to cross-react with anti-dsDNA antibodies (U.S. Pat. No. 5,276,013). The use of dsON conjugated with non-immunogenic carriers, also referred to as platforms, has been proposed for a therapeutic approach for the treatment of SLE. For example, a tetrakis conjugate, LJP 249, composed of four dsON attached to a poly(ethylene glycol) valency platform was used to demonstrate tolerance in an immunized mouse model system (Jones et al. (1994) *Bioconjugate Chem.* 5:390–399).

LJP 394, a tetravalent conjugate composed of four dsON attached to a platform, was shown to delay progression of renal disease and extend survival in the BXSB experimental murine lupus nephritis model (Plunkett et al. (1995) *Lupus* 4:S99; Coutts et al. (1996) *Lupus* 5:158–159). LJP 394 has also been shown to lower anti-dsDNA antibodies in human patients with SLE (Weisman et al. (1997) *J. Rheumatol.* 24:314–318).

Other literature describes methods which may be used in the treatment of SLE, including methods of reducing levels of circulating antibodies by inducing B cell tolerance, including, but not limited to, U.S. Pat. Nos. 5,276,013; 5,391,785; 5,786,512; 5,726,329; 5,552,391; 5,268,454; 5,606,047; 5,633,395; 5,162,515; U.S. Ser. No. 08/118,055 (U.S. Pat. No. 6,060,056); U.S. Ser. Nos. 60/088,656 and 60/103,088 (U.S. Ser. No. 09/328,199 and PCT App. No. PCT/US99/13194).

Although overall patient prognosis in SLE has improved, treatment regimens are not ideal and lupus nephritis continues to be associated with relatively poor overall survival (Seleznick et al. (1991) *Semin. Arthritis Rheum.* 21:73–80).

What is needed are improved methods of treatment of SLE and improved methods of identifying patients who may particularly respond to a given treatment.

All references cited herein are hereby incorporated by reference in their entirety.

DISCLOSURE OF THE INVENTION

The invention provides methods relating to immunotolerance treatment of lupus based on assessment of initial affinity of antibody from the individual (i.e., antibody associated with lupus, namely, anti-ds DNA antibodies). The invention also provides methods of identifying individuals suitable (or unsuitable) for treatment based on assessing antibody affinity, as well as methods of treatment based on assessment of change of affinity (if any) upon receiving treatment.

Accordingly, in one aspect, the invention provides methods of treating SLE (including lupus nephritis) in an individual, comprising administering to the individual a conjugate comprising (a) a non-immunogenic valency platform molecule and (b) two or more double stranded DNA epitopes, preferably polynucleotides, which specifically bind to an antibody from the individual which specifically binds to double stranded DNA, wherein affinity of the epitope, preferably polynucleotide, for the antibody from the individual is used as a basis for selecting the individual to receive the treatment. In other embodiments, the invention provides methods of treating SLE in an individual, comprising administering to the individual a conjugate comprising (a) a non-immunogenic valency platform molecule and (b) two or more double stranded DNA epitopes, preferably polynucleotides which specifically bind to an antibody from the individual which specifically binds to double stranded DNA, wherein affinity of the epitope, preferably polynucleotide, for the antibody from the individual is used as a basis for selecting the individual to continue to receive the treatment.

As using affinity as a basis for selecting an individual suitable for treatment indicates, the treatment methods described herein generally entail measuring antibody affinity (of an individual's anti-double stranded DNA antibodies) for the dsDNA epitope.

In another aspect, the invention provides methods of treating systemic lupus erythematosus (SLE) in an individual, comprising administering to the individual a conjugate comprising (a) a non-immunogenic valency platform molecule and (b) two or more polynucleotides which specifically bind to an antibody from the individual which specifically binds to double stranded DNA, said polynucleotide preferably comprising, consisting essentially of or consisting of the double stranded DNA sequence 5'-GTGTGTGTGTGTGTGTGTGT-3' (SEQ D NO: 1), wherein the apparent equilibrium dissociation constant ($K_D'$), or its functional equivalent, for the polynucleotide with respect to the antibody from the individual before or upon initiation of treatment is less than about 1.0 mg IgG per ml, and wherein said $K_D'$ value (or its functional equivalent) is used as a basis for selecting the individual to receive the treatment.

In some embodiments, the treatment methods also include a selection step comprising assessing before initiation of treatment an apparent equilibrium dissociation constant ($K_D'$) (or its functional equivalent) for the epitope, preferably a polynucleotide, contained within the conjugate with respect to antibodies from the individual which specifically bind to double stranded DNA, said conjugate comprising (a) a non-immunogenic valency platform molecule and (b) two or more dsDNA epitopes which specifically bind to an antibody from the individual which specifically binds to double stranded DNA, wherein the individual is selected to receive the treatment if the $K_D'$ (or its functional equivalent) is less than about 1.0 mg IgG per ml. Other, lower $K_D'$ values are described herein which could apply to any of the dsDNA epitopes contemplated for use in treatment, as are percentile ranking with respect to a given patient population as described herein. Preferably, the dsDNA epitopes are polynucleotides, said polynucleotide preferably comprising, consisting essentially of or consisting of the double stranded DNA sequence 5'-GTGTGTGTGTGTGTGTGTGT-3' (SEQ ID NO: 1).

In another aspect, the invention provides methods of treating SLE in an individual comprising: (a) assessing affinity of an anti-double stranded DNA antibody from the individual with respect to a dsDNA epitope which is to be used in treatment, wherein the individual is selected for treatment based on said antibody affinity; and (b) administering to said selected individual a conjugate comprising (a) a non-immunogenic valency platform molecule and (b) two or more of the dsDNA epitopes.

In another aspect, the invention provides methods of treating lupus nephritis in an individual, comprising administering to the individual a conjugate comprising (a) a non-immunogenic valency platform molecule and (b) two or more polynucleotides which specifically bind to an antibody from the individual which specifically binds to double stranded DNA, said polynucleotide comprising, consisting essentially of, or consisting of the double stranded DNA sequence 5'-GTGTGTGTGTGTGTGTGTGT-3' (SEQ ID NO: 1), wherein the apparent equilibrium dissociation constant ($K_D'$) (or its functional equivalent) for the polynucleotide in the conjugate with respect to the antibody from the individual before or upon initiation of treatment is less than about 1.0 mg IgG per ml, and wherein said $K_D'$ value (or its functional equivalent) is used as a basis for selecting the individual to receive the treatment.

In another aspect, the invention provides methods of treating SLE in an individual, comprising: (a) assessing before or upon initiation of treatment an apparent equilibrium dissociation constant ($K_D'$) for a dsDNA epitope in or of a conjugate with respect to an antibody from the individual which specifically binds to double stranded DNA, said conjugate comprising (a) a non-immunogenic valency platform molecule and (b) two or more said epitopes which specifically bind to an antibody from the individual which specifically binds to double stranded DNA and (b) administering to the individual the conjugate in an amount sufficient to increase the $K_D'$, wherein treatment is continued if $K_D'$ is increased at least about 20% compared to $K_D'$ before or upon initiation of treatment. In other embodiments, treatment methods comprise administering any of the conjugate(s) described herein in an amount sufficient to reduce the affinity as reflected by an affinity measurement (as, for example, reflected by increased $K_D'$), preferably by at least about 20%, although greater changes may be desirable.

In another aspect, the invention provides methods of treating lupus nephritis in an individual comprising administering to the individual a conjugate comprising (a) a non-immunogenic valency platform molecule and (b) two or more dsDNA epitopes which specifically bind to an antibody from the individual which specifically binds to double stranded DNA. In some embodiments, antibody affinity is assessed as described herein. In some embodiments, conjugate is administered in an amount sufficient to reduce antibody affinity.

In another aspect, the invention provides methods of identifying an individual who may be suitable for treatment for SLE, said treatment comprising administration of a conjugate comprising (a) a non-immunogenic valency platform molecule and (b) two or more polynucleotides which specifically bind to an antibody from the individual which specifically binds to double stranded DNA, said polynucleotide comprising, consisting essentially of, or consisting of the dsDNA sequence 5'-GTGTGTGTGTGTGTGTGTGT-3' (SEQ ID NO:1), said method comprising measuring the apparent equilibrium dissociation constant ($K_D'$) or its functional equivalent for the polynucleotide used in the conjugate and anti-double stranded DNA antibodies from the individual before or upon initiation of treatment, wherein an individual is identified by $K_D'$ of less than about 1.0 mg IgG per ml or a functional equivalent thereof.

In another aspect, the invention provides methods of identifying an individual who may be unsuitable for treatment for SLE, said treatment comprising administration of a conjugate comprising (a) a non-immunogenic valency platform molecule and (b) two or more polynucleotides which specifically bind to an antibody from the individual which specifically binds to double stranded DNA, said polynucleotide comprising, consisting essentially of, or consisting of the dsDNA sequence 5'-GTGTGTGTGTGTGTGTGTGT-3' (SEQ ID NO: 1), said method comprising measuring the apparent equilibrium dissociation constant ($K_D'$) or its functional equivalent for the polynucleotide of the conjugate and anti-double stranded DNA antibodies from the individual before or upon initiation of treatment, wherein an individual is identified by $K_D'$ of more than about 1.0 mg IgG per ml or a functional equivalent thereof.

In another aspect, the invention provides methods of monitoring treatment for SLE in an individual, said treatment comprising administration of a conjugate comprising (a) a non-immunogenic valency platform molecule and (b) two or more dsDNA epitopes, preferably polynucleotides, which specifically bind to an antibody from the individual which specifically binds to double stranded DNA, said method comprising measuring the affinity for the dsDNA epitopes, preferably polynucleotide(s) of the conjugate and anti-ds DNA antibodies from the individual. In some aspects, the apparent equilibrium dissociation constant ($K_D'$) is measured.

In another aspect, the invention provides kits comprising a molecule, such as a polynucleotide, comprising an epitope which binds to an anti-double stranded DNA antibody in suitable packaging, preferably further comprising instructions as to measuring affinity of anti-ds DNA antibodies from an individual for the epitope.

In another aspect, the invention provides kits comprising (1) a conjugate comprising (a) a non-immunogenic valency platform molecule and (b) two or more polynucleotides which specifically bind to an antibody from an individual which specifically binds to double stranded DNA; and (2) instructions for using the conjugate to detect affinity of the conjugate for anti-ds DNA antibodies from an individual.

MODES FOR CARRYING OUT THE INVENTION

Figure 1A:
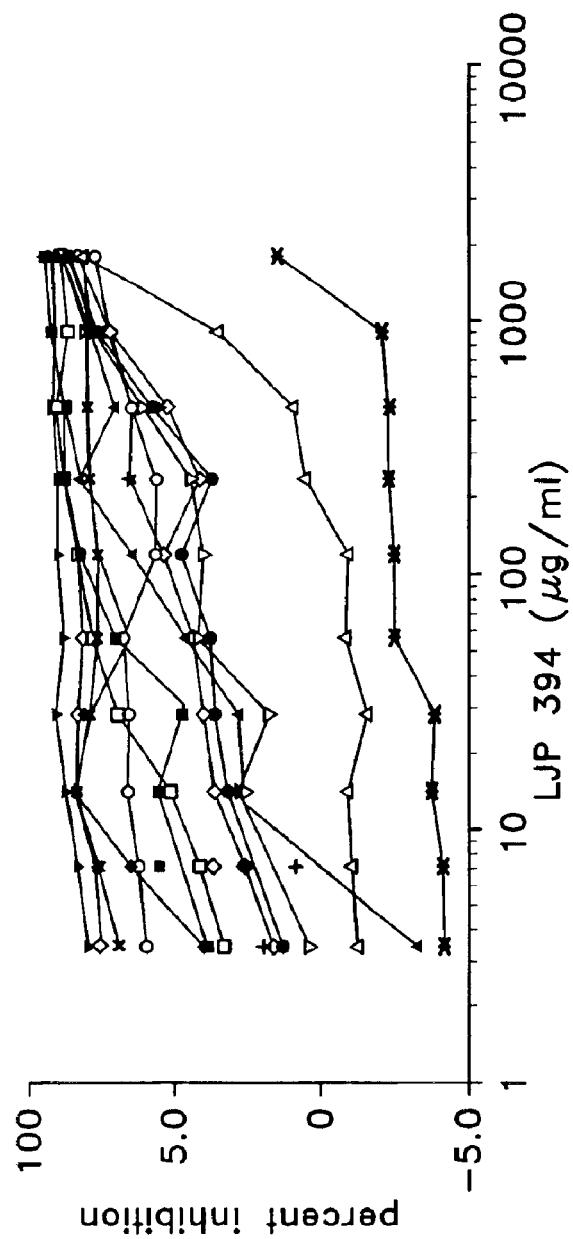
FIGS. 1A–C are graphs depicting competitive inhibition by LJP 394 of antibodies from groups of SLE patients' sera binding to $^{125}$I-labeled dsDNA.

We have discovered that average affinity of anti-dsDNA antibody from an individual suffering from lupus to an epitope that will be or is used as a basis for treatment is predictive of efficacy of treatment designed to induce immunotolerance by administering a conjugate containing at least two molecules comprising the epitope. Based on our evaluation of clinical data pertaining to such treatment in lupus patients, we have discovered the following: (a) initial antibody affinity for the DNA epitope used in treatment can predict the degree of responsiveness to treatment, in terms of reduction of antibody affinity as well as reduction of symptoms and reduction of amount (titer) of anti-ds DNA antibody, with patients with higher affinity antibodies being better responders to treatment; (b) initial antibody affinity for the DNA epitope used in treatment can predict the degree of efficacy, in terms of reduction of symptoms, with patients with higher affinity antibodies displaying reduction of symptoms compared to patients with lower affinity antibodies (or patients with high affinity antibodies receiving no treatment); (c) change in antibody affinity for the DNA epitope used in the treatment can predict the degree of efficacy in terms of reduction of symptoms, with patients displaying a requisite change (reduction) of affinity displaying reduction of symptoms compared to patients failing to display the requisite change. In contrast, previous reports disclosed measuring titer of anti-ds DNA antibodies upon administration of a conjugate described herein (LJP 394) (i.e., levels of anti-ds DNA antibodies as indicated by binding to ds DNA), as opposed to reporting affinity of a patient's anti-ds DNA antibodies for the polynucleotide epitope of the conjugate. In view of our analysis, neither these initial reported titers or changes in titers were predictive of clinical outcome.

Accordingly, the invention provides methods of treatment and methods of identifying individuals suitable for the treatments described herein which entail assessment of affinity of antibody from an individual for an epitope that is, has been, and/or will be, the basis of immunotolerance treatment as described herein.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Animal Cell Culture* (R. I. Freshney), ed., 1987); *Methods in Enzymology* (Academic Press, Inc.); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991) and *Short Protocols in Molecular Biology* (Wiley and Sons, 1999).

Definitions

"Affinity" of an antibody from an individual for an epitope to be used, or used, in treatment(s) described herein is a term well understood in the art and means the extent, or strength, of binding of antibody to epitope. Affinity may be measured and/or expressed in a number of ways known in the art, including, but not limited to, equilibrium dissociation constant ($K_D$ or $K_d$), apparent equilibrium dissociation constant ($K_D'$ or $K_d'$), and $IC_{50}$ (amount needed to effect 50% inhibition in a competition assay; used interchangeably herein with "$I_{50}$"). It is understood that, for purposes of this invention, an affinity is an average affinity for a given population of antibodies which bind to an epitope. Values of $K_D'$ reported herein in terms of mg IgG per ml or mg/ml indicate mg Ig per ml of serum, although plasma can be used.

When antibody affinity "is used as a basis" for administration of the treatment methods described herein, or selection for the treatment methods described herein, antibody affinity is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits. As would be well understood by one in the art, measurement of antibody affinity in a clinical setting is a clear indication that this parameter was used as a basis for initiating, continuing, adjusting and/or ceasing administration of the treatments described herein.

An antibody affinity measured "before or upon initiation of treatment" is antibody affinity measured in an individual before the individual receives the first administration of a treatment modality described herein and/or within at least about 4 weeks, preferably within at least about 2 weeks, preferably within at least about 1 week, preferably within at least about 5 days, preferably within at least about 3 days, preferably within at least about 2 days, preferably within at least about 1 day upon receiving the first administration of a treatment modality described herein.

A "population" is a group of individuals with an antibody-mediated pathology. For a given population (which may vary in terms of number of members, depending on the context) antibody affinities vary over a range (i.e., maximum and minimum affinities).

An individual who "may be suitable", which includes an individual who is "suitable" for treatment(s) described herein, is an individual who is more likely than not to benefit from administration of said treatments. Conversely, an individual who "may not be suitable" or "may be unsuitable", which includes an individual who is "unsuitable" for treatment(s) described herein, is an individual who is more likely than not to fail to benefit from administration of said treatments.

As used herein, "treatment" is an approach for obtaining beneficial or desired results including and preferably clinical results. For purposes of this invention, beneficial or desired clinical results include, but are not limited to, one or more of the following: alleviation of symptoms, diminishment of extent of disease, stabilized (i.e., not worsening) state of disease, preventing spread (i.e., metastasis) of disease, preventing occurrence or recurrence of disease, delay or slowing of disease progression, amelioration of the disease state, remission (whether partial or total), reduction of incidence of disease and/or symptoms. Treatment of lupus includes any aspect of lupus, including, but not limited to, lupus nephritis, which is a chronic inflammatory kidney disease. During lupus nephritis, "flares" may occur. "Flares" refer to an increase in activity, generally inflammatory activity. If the activity is in the kidneys, then the flare is referred to as a "renal flare". "Renal flares" can be identified by evaluating factors including, but not limited to, proteinuria levels, hematuria levels, and serum creatinine levels. The "treatment" of lupus nephritis may be administered when no symptoms of lupus nephritis are present, and such treatment (as the definition of "treatment" indicates) reduces the incidence of flares. Also encompassed by "treatment" is a reduction of pathological consequences of any aspect of lupus, such as lupus nephritis.

"SLE flares" are used herein to refer to flares (i.e. acute clinical events) which occur in patients with SLE. The SLE flares may be in various major organs, including but not limited to, kidney, brain, lung, heart, liver, and skin. SLE flares include renal flares.

"High dose corticosteroid and/or cyclophosphamide" or "HDCC" as used herein refers to intervention with an increased dosage of corticosteroid alone or with cyclophosphamide. High dose generally refers to corticosteroids. Such intervention generally occurs upon a flare, or acute episode. Generally, for example, the increase dosage is at least a 15 mg/day and can be greater than 20 mg/day. HDCC may be administered using standard clinical protocols. A clinician may monitor a patient and determine when HDCC treatment is needed by evaluating factors including, but not limited to, proteinuria levels, hematuria levels, and serum creatinine levels. In general, patients who experience renal flares are given HDCC treatment, although this treatment is used for other aspects of lupus.

An "equivalent" or "functional equivalent" of $K_D'$ or a numerical value for $K_D'$ is a parameter or value for a parameter which also reflects affinity. For example, an equivalent of $K_D'$ is $IC_{50}$. As another example, an equivalent value of $K_D'$ of 0.5 could be an $IC_{50}$ of 200, if they reflect the same, or about the same, affinity. Determining such equivalents is well within the skill of the art and such equivalents and their determination are encompassed by this invention. Generally, reference to $K_D'$ includes reference to functional equivalents of $K_D'$.

As used herein, the singular form "a", "an", and "the" includes plural references unless indicated otherwise. For example, "an" antibody includes one or more antibodies.

An "epitope" is a term well-understood in the art and means any chemical moiety which exhibits specific binding to an antibody. An "epitope" can also comprise an antigen, which is a moiety or molecule that contains an epitope, and, as such, also specifically binds to antibody.

A "double-stranded DNA epitope" or "dsDNA epitope" is any chemical moiety which exhibits specific binding to an anti-double-stranded DNA antibody and as such includes molecules which comprise such epitope(s). Further discussion of double-stranded DNA epitopes suitable for the conjugates of the invention are described below. The term "epitope" also includes mimetics of double-stranded DNA itself, which are described below.

An epitope that "specifically binds" to an antibody is a term well understood in the art, and methods to determine such specific binding are also well known in the art. A molecule is said to exhibit "specific binding" if it reacts or associates more frequently, more rapidly, with greater duration and/or with greater affinity with a particular cell or substance than it does with alternative cells or substances. An antibody "specifically binds" to a target if it binds with greater affinity, avidity, more readily, and/or with greater duration than it binds to other substances.

An "anti-double-stranded DNA antibody" or "anti-dsDNA antibody" or "double-stranded DNA antibody", used interchangeably herein, is any antibody which specifically binds to double-stranded DNA (dsDNA). Any antibody includes an antibody of any class, such as IgG, IgA, or IgM, and the antibody need not be of any particular class. As clearly indicated in the definition of "antibody" provided herein, a "anti-double-stranded DNA antibody" encompasses any fragment(s) that exhibits this requisite functional (i.e., specific binding to dsDNA) property, such as fragments that contain the variable region, such as Fab fragments. As discussed below, it is understood that specific binding to any anti-double-stranded DNA antibody (or functional fragment) is sufficient.

The term "circulating anti-double-stranded DNA antibody", as used herein, intends an anti-double-stranded DNA antibody which is not bound to a double-stranded DNA epitope on and/or in a biological sample, i.e., free antibody.

An "antibody" (interchangeably used in plural form) is an immunoglobulin molecule capable of specific binding to a target, such as a carbohydrate, polynucleotide or polypeptide, through at least one antigen recognition site, located in the variable region of the immunoglobulin molecule. As used herein, the term encompasses not only intact antibodies, but also fragments thereof (such as Fab, Fab', F(ab')$_2$, Fv), single chain (ScFv), mutants thereof, fusion proteins comprising an antibody portion, humanized antibodies, and any other modified configuration of the immunoglobulin molecule that comprises an antigen recognition site of the required specificity.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. For purposes of this invention, unless otherwise indicated, sequences presented herein denote double stranded sequences. For example, the polynucleotide comprising, consisting essentially of, or consisting of the double stranded sequence 5'-GTGTGTGTGTGTGTGTGTGT-3'(SEQ ID NO:1) includes the complementary polynucleotide sequence, particularly the sequence 3'-CACACACACACACACACACA-5' (SEQ ID NO:2). It is understood that the double stranded polynucleotide sequences described herein also include the modifications described herein. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. A phosphorothioate linkage can be used in place of a phosphodiester linkage. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. For purposes of this invention, a polynucleotide is generally an isolated polynucleotide of less than about 1 kb, preferably less than about 500 base pairs (bp), preferably less than about 250 bp, preferably less than about 100 bp, preferably less than about 50 bp. However, it is understood that a polynucleotide of any size or configuration could be used as long as it exhibits the requisite binding to anti ds DNA antibody from an individual. It is further understood that a different polynucleotide (for example, in terms of size and/or sequence) other than the one that is to be, was, or will be used in treatment, as long as both polynucleotides exhibit equivalent (or convertible) binding affinities to anti-ds DNA antibodies from an individual. In other words, non-identical polynucleotides may be employed with respect to affinity determination and treatment.

Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

"Naturally occurring" refers to an endogenous chemical moiety, such as a carbohydrate, polynucleotide or polypeptide sequence, i.e., one found in nature. Processing of naturally occurring moieties can occur in one or more steps, and these terms encompass all stages of processing. Conversely, a "non-naturally occurring" moiety refers to all other moieties, i.e., ones which do not occur in nature, such as recombinant polynucleotide sequences and non-naturally occurring carbohydrates.

As used herein, the term "immunogen" means a chemical entity that elicits a humoral immune response when injected into an animal. Immunogens have both B cell epitopes and T cell epitopes.

As used herein, the term "analog" (also termed an "mimetic") of an immunogen means a biological or chemical compound which specifically binds to an antibody to which the immunogen specifically binds. As such a "double-stranded DNA epitope" includes mimetics of naturally-occurring double-stranded DNA. An "analog" or "mimetic" shares an epitope, or binding specificity, with double-stranded DNA. An analog may be any chemical substance which exhibits the requisite binding properties, and thus may be, for example, a simple or complex organic or inorganic molecule; a polypeptide; a polynucleotide; a carbohydrate; a lipid; a lipopolysaccharide; a lipoprotein, or any combination of the above, including, but not limited to, a polynucleotide-containing polypeptide; a glycosylated polypeptide; and a glycolipid. The term "analog" encompasses the term "mimotope", which is a term well known in the art.

An "individual" is a vertebrate, preferably a mammal, more preferably a human. Mammals include, but are not limited to, farm animals, sport animals, pets, primates, mice and rats.

A "T cell epitope" means a component or portion thereof for which a T cell has an antigen-specific specific binding site, the result of binding to which activates the T cell. Where an embodiment of the invention is described as "lacking" a T cell epitope, this is taken to mean that a T cell epitope is not detectable using standard assays in the art. For purposes of this invention, an epitope that "lacks" a T cell epitope means that the epitope lacks a T cell epitope which causes T cell activation in the individual(s) to be treated (i.e., who is to receive an epitope-presenting valency platform molecule). It is likely that, for example, an epitope may lack a T cell epitope(s) with respect to an individual, or a group of individuals, while possessing a T cell epitope(s) with respect to other individual(s). Methods for detecting the presence of a T cell epitope are known in the art and include assays which detect T cell proliferation (such as thymidine incorporation). Immunogens that fail to induce statistically significant incorporation of thymidine above background (i.e., generally p less than 0.05 using standard statistically methods) are generally considered to lack T cell epitopes, although it will be appreciated that the quantitative amount of thymidine incorporation may vary, depending on the immunogen being tested. Generally, a stimulation index below about 2–3, more preferably less than about 1, indicates lack of T cell epitopes. The presence of T cell epitopes can also be determined by measuring secretion of T cell-derived lymphokines according to standard methods. Location and content of T cell epitopes, if present, can be determined empirically. It is understood that, over time, more sensitive assays may be developed to detect the presence of T cell epitopes, and that specifying the lack of T cell epitopes is dependent on the type of detection system used.

"Inducing tolerance" or "inducing immunotolerance" means a reduction and/or stabilization of the extent of an immune response to an immunogen. An "immune response" may be humoral and/or cellular, and may be measured using standard assays known in the art. For purposes of this invention, the immune response is generally reflected by the presence of, and/or the levels of, anti-double-stranded DNA antibodies. Quantitatively the reduction (as measured by reduction in antibody production and/or levels) is at least about 15%, preferably at least about 25%, more preferably at least about 50%, more preferably at least about 75%, more preferably at least about 90%, even more preferably at least about 95%, and most preferably 100%. It is understood that the tolerance is antigen-specific, and applies for purposes of the invention to those individuals having anti-double-stranded DNA antibodies. "Inducing tolerance" also includes slowing and/or delaying the rate of increase of antibody level.

As used herein, the term "B cell anergy" intends unresponsiveness of those B cells requiring T cell help to produce and secrete antibody and includes, without limitation, clonal deletion of immature and/or mature B cells and/or the inability of B cells to produce antibody. "Unresponsiveness" means a therapeutically effective reduction in the humoral response to an immunogen. Quantitatively the reduction (as measured by reduction in antibody production) is at least 50%, preferably at least 75% and most preferably 100%.

An "effective amount" (when used in the lupus context, or in the antibody-mediated pathology context) is an amount sufficient to effect beneficial or desired results including clinical results. An effective amount can be administered in one or more administrations. For purposes of this invention, an effective amount of conjugate described herein (or a composition comprising a conjugate) an amount sufficient to reduce circulating levels of anti-double-stranded DNA antibodies, preferably by inducing tolerance, particularly with respect to anti-double-stranded DNA antibodies. In terms of treatment, an "effective amount" of conjugate described herein (or a composition comprising a conjugate) is an amount sufficient to palliate, ameliorate, stabilize, reverse, slow or delay progression of or prevent systemic lupus erythematosus (SLE), including the progressive inflammatory degeneration of the kidneys that results from SLE (i.e., lupus nephritis).

A "stable complex" formed between any two or more components in a biochemical reaction, refers to a duplex or complex that is sufficiently long-lasting to persist between formation of the duplex or complex and subsequent detection, including any optional washing steps or other manipulation that may take place in the interim.

An "isolated" or "purified" polypeptide or polynucleotide is one that is substantially free of the materials with which it is associated in nature. By substantially free is meant at least 50%, preferably at least 70%, more preferably at least 80%, even more preferably at least 90% free of the materials with which it is associated in nature.

As used herein "valency platform molecule" means a nonimmunogenic molecule containing sites which allow the attachment of a discrete number of epitopes and/or mimetic(s) of epitopes. A "valency" of a conjugate or valency platform molecule indicates the number of attachment sites per molecule for a double-stranded DNA epitope(s). Alternatively, the valency of a conjugate is the ratio (whether absolute or average) of double-stranded DNA epitope to valency platform molecule.

"Nonimmunogenic", when used to describe the valency platform molecule, means that the valency platform molecule fails to elicit an immune response (i.e., T cell and/or B cell response), and/or fails to elicit a sufficient immune response, when it is administered by itself to an individual. The degree of acceptable immune response depends on the context in which the valency platform molecule is used, and may be empirically determined.

An epitope which is "conjugated" to a valency platform molecule is one that is attached to the valency platform molecule, either by covalent and/or non-covalent interactions.

An "epitope-presenting valency platform molecule" is a valency platform molecule which contains attached, or bound, epitopes, at least some of which (at least two of which) are able to bind an antibody of interest.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

"In conjunction with" refers to administration of one treatment modality in addition to another treatment modality, such as administration of a conjugate described herein in addition to administration of corticosteroid cyclophosphamide immunosuppressants (or other immunosuppressant therapy) to the same individual. As such, "in conjunction with" refers to administration of one treatment modality before, during or after delivery of the other treatment modality to the individual.

An "antibody-mediated pathology" is an immune response disorder which is associated with inappropriate production of antibodies, generally directed to self-antigens. Antibody-mediated pathologies include, but are not limited to, lupus; antibody-mediated thrombosis and thrombocytopenia; anti-phospholipid syndrome; myasthenia gravis. Because an immune response disorder is context dependent, for purposes of this invention, an "antibody-mediated pathology" can also encompass transplantation rejection (especially xenotransplantation), in which an immune response is inappropriate with respect to attempting to maintain the foreign transplanted tissue, and Rh-based rejection in pregnancy.

"Receiving treatment" includes initial treatment and/or continuing treatment.

"Comprising" means including.

Methods of treatment of lupus and methods of identifying individuals suitable for treatment of lupus based on assessment of antibody affinity The methods described herein entail assessing antibody affinity from an individual, wherein said individual has, or is suspected of having, systemic lupus erythematosus (SLE). For purposes of this invention, (a) the affinity in question is with respect to an individual's antibodies, that is, antibodies obtained from that individual; (b) the antibody for which affinity is measured is an antibody associated with, and/or implicated in, an antibody-mediated pathology, namely systemic lupus erythematosus (SLE); and (c) the binding of interest is binding of antibody to an epitope which binds to the antibody(ies), with the epitope to be used in the proposed treatment, as described herein (i.e., a dsDNA epitope).

The invention provides (a) methods of treating individuals based on assessment of initial antibody affinity (i.e., antibody affinity before or upon initiation of treatment); (b) methods of treating individuals based on assessment of change in antibody affinity, if any (i.e., comparison of (i) antibody affinity before or upon initiation of treatment with (ii) antibody affinity after a period treatment sufficient to elicit a change in affinity, if any); (c) methods of screening individuals who may be suitable for receiving the treatment(s) described herein (or, alternatively, individuals who may be unsuitable to receive the treatment(s) described herein) based on assessment of initial antibody affinity; (d) methods of screening individuals who may be suitable for receiving treatment(s) described herein (or, alternatively, individuals who may be unsuitable to receive treatment(s) described herein) based on assessment of the change in antibody affinity, if any, (e) methods of monitoring the treatment(s) described herein based on assessment of antibody affinity.

With respect to the methods described herein, the screening methods (i.e., methods of identifying individuals as suitable or unsuitable for treatment) may be practiced independently of the treatment methods, and as such are distinct from treatment methods. The screening methods described herein may be practiced by a skilled technician other than a medical doctor, using equipment and/or techniques of the art.

For all embodiments of the invention which use or are directed to $K_D'$, whether screening, treatment, monitoring, or any other methods directed to assessing affinity, it is understood that other, equivalent values can be measured and used, and are encompassed by this invention. For example, as discussed below, there are a number of methods known in the art which can measure (and express) affinity of antibodies from an individual for an epitope to be used for treatment (in the context of this invention, a double stranded DNA epitope). $K_D'$ is one of these parameters, and equivalent parameters can be measured and used in this invention. Further, with respect to $K_D'$ cut-off values reported herein, the basis of this finding was administering about 100 mg of LJP 394 conjugate about once a week.

Methods of Treatment

Accordingly, the invention provides methods of treating SLE in an individual, comprising administering to the individual a conjugate comprising (a) a non-immunogenic valency platform molecule and (b) two or more dsDNA epitopes (such as two or more molecules comprising a dsDNA epitope), preferably polynucleotides, which specifically bind to an antibody from the individual which specifically binds to double stranded DNA, wherein affinity of the epitope, preferably polynucleotide (of the conjugate) for the antibody from the individual is used as a basis for selecting the individual to receive the treatment. In other embodiments, the invention provides methods of treating SLE in an individual, comprising administering to the individual a conjugate comprising (a) a non-immunogenic valency platform molecule and (b) two or more dsDNA epitopes, preferably polynucleotides, which specifically bind to an antibody from the individual which specifically binds to double stranded DNA, wherein affinity of the epitope, preferably polynucleotide (of the conjugate) for the antibody from the individual is used as a basis for selecting the individual to continue to receive the treatment. Methods of determining affinities are known in the art and described below.

Measurement of affinity, either represented by measuring $K_D'$ or by some other method, either before or during treatment is strong, if not conclusive, indication that this parameter was a basis for selecting the individual to receive (and/or continue to receive) treatment. Accordingly, with respect to all treatment methods described herein, and as the definition for "is used as a basis" states, other embodiments include (1) assessing, or measuring, the affinity as described herein (and preferably selecting an individual suitable for receiving (including continuing to receive) treatment); and (2) administering the treatment(s) as described herein. As described herein, in some embodiments, more than one measurement is made, when change (if any) in affinity is assessed.

dsDNA epitopes for use in the treatment methods are described herein. In some embodiments, the dsDNA epitope is a polynucleotide, such as 5'-GTGTGTGTGTGTGTGTGTGT-3' (SEQ ID NO:1). Affinity may be measured using the epitope (or a molecule or moiety comprising the epitope) used in the conjugate; alternatively, a similar, non-identical epitope may be used, as long as its affinity may be at least correlated to the affinity of the epitope used in the conjugate, so that a meaningful measurement of affinity may be obtained.

The invention provides methods of treating SLE in an individual, comprising administering to the individual a conjugate comprising (a) a non-immunogenic valency platform molecule and (b) two or more polynucleotides which specifically bind to an antibody from the individual which specifically binds to double stranded DNA, said polynucleotide comprising, consisting essentially of, or consisting of the double stranded sequence 5'-GTGTGTGTGTGTGTGTGTGT-3' (SEQ ID NO:1), wherein the apparent equilibrium dissociation constant ($K_D'$) for the polynucleotide in the conjugate with respect to the antibody from the individual before or upon initiation of treatment is less than about 1.0 mg IgG per ml, and wherein said $K_D'$ value is used as a basis for selecting the individual to receive the treatment. In other embodiments, the $K_D'$ is less than about any of the following: 0.8; 0.7; 0.6; 0.5; 0.4; 0.3; 0.2; 0.1; 0.09; 0.08; 0.07; 0.06; 0.05; 0.025. These values for $K_D'$ apply to all methods in which $K_D'$ is assessed (including treatment and/or screening), such as those in which treatment based on 5'-GTGTGTGTGTGTGTGTGTGT-3' (SEQ ID NO: 1) is contemplated. In some embodiments, $K_D'$ is less than about 0.8 mg IgG per ml. In some embodiments, $K_D'$ is less than about 0.5 mg IgG per ml. In some embodiments, $K_D'$ is less than about 0.1 mg IgG per ml. Methods of measuring $K_D'$ are described below. Measurement of affinity, either represented by measuring $K_D'$ or by some other method, either before or during treatment is strong, if not conclusive, indication that this parameter was a basis for selecting the individual to receive treatment.

In some embodiments, the invention provides methods of treating SLE in an individual, comprising: (a) assessing before or upon initiation of treatment an apparent equilibrium dissociation constant ($K_D'$) for a dsDNA epitope (including a molecule comprising a dsDNA epitope), preferably a polynucleotide in or of a conjugate with respect to antibodies from the individual which specifically bind to double stranded DNA, said conjugate comprising (a) a non-immunogenic valency platform molecule and b) two or more DNA epitopes, preferably polynucleotides, which specifically bind to an antibody from the individual which specifically binds to double stranded DNA, said polynucleotide (if that is the dsDNA epitope used) preferably comprising, consisting essentially of or consisting of the (double stranded, or ds) sequence 5'-GTGTGTGTGTGTGTGTGTGT-3' (SEQ ID NO: 1), wherein the individual is selected to receive the treatment if the $K_D'$ is less than about 1.0 mg IgG per ml; and (b) administering to the individual the conjugate, preferably in an amount sufficient to increase the $K_D'$. In other embodiments, the $K_D'$ is less than about any of the following: 0.8; 0.7; 0.6; 0.5; 0.4; 0.3; 0.2; 0.1; 0.09; 0.08; 0.07; 0.06; 0.05.; 0.025. Methods of measuring $K_D'$ are described below.

In other embodiments, the invention provides methods of treating SLE in an individual, comprising: (a) assessing before or upon initiation of treatment an apparent equilibrium dissociation constant ($K_D'$) for a dsDNA epitope, preferably a polynucleotide in or of a conjugate with respect to antibodies from the individual which specifically bind to double stranded DNA, said conjugate comprising (a) a non-immunogenic valency platform molecule and (b) two or more such epitopes, preferably polynucleotides, which specifically bind to an antibody from the individual which specifically binds to double stranded DNA, said polynucleotide (if used) comprising, consisting essentially of or consisting of the (ds) sequence 5'-GTGTGTGTGTGTGTGTGTGT-3' (SEQ ID NO:1); and (b) administering to the individual the conjugate in an amount sufficient to increase the $K_D'$, wherein treatment is continued if $K_D'$ is increased at least about 20% compared to $K_D'$ before or upon initiation of treatment. For these embodiments, a $K_D'$ measured after initiation of treatment (for comparison to $K_D'$ before or upon initiation of treatment) is measured at least about 4 weeks, preferably at least about 6 weeks, more preferably at least about 10 weeks, more preferably at least about 12 weeks, after initiation of treatment. We observed a large range of change in antibody affinity upon treatment over a treatment population (FIG. 5). Accordingly, in other embodiments, treatment is continued if $K_D'$ is increased at least about any of the following (as compared to $K_D'$ before or upon initiation of treatment): 40%, 50%, 75%, 100%, 200%, 500%. Methods of measuring $K_D'$ are described below.

In some embodiments, a conjugate is administered in an amount sufficient to reduce incidence of, or likelihood of, renal flares (lupus nephritis). Based on our observations, the amount sufficient for this reduction for LJP 394 is about 100 mg, given once per week. Patients receiving this amount of conjugate, who had an initial $K_D'$ of less than about 0.8, displayed more than about two-fold lower hospitalizations due to this disorder. For an individual patient, an effective amount of conjugate may be related to and/or a function of, that individual's antibody affinity, with patients with higher affinity able to respond to a lower dose. Conversely, a patient with lower affinity antibodies may respond if given a sufficiently high(er) dose.

Accordingly, the invention provides methods of treating lupus nephritis in an individual, comprising administering to the individual a conjugate comprising (a) a non-immunogenic valency platform molecule and (b) two or more polynucleotides which specifically bind to an antibody from the individual which specifically binds to double stranded DNA, said polynucleotide comprising, consisting essentially of, or consisting of the (ds) sequence 5'-GTGTGTGTGTGTGTGTGTGT-3' (SEQ ID NO: 1), wherein the apparent equilibrium dissociation constant ($K_D$') for the polynucleotide in the conjugate with respect to the antibody from the individual before or upon initiation of treatment is less than about 1.0 mg IgG per ml, and wherein said $K_D$' value is used as a basis for selecting the individual to receive the treatment. In other embodiments, the $K_D$' is less than about any of the following: 0.8; 0.7; 0.6; 0.5; 0.4; 0.3; 0.2; 0.1; 0.09; 0.08; 0.07; 0.06 0.05; 0.025. Methods of measuring $K_D$' are described below. Measurement of affinity, either represented by measuring $K_D$' or by some other method, either before or during treatment is strong, if not conclusive, indication that this parameter was a basis for selecting the individual to receive treatment.

In some embodiments, a conjugate as described herein is administered in an amount sufficient to reduce the dosage of corticosteroid and/or cyclophosphamide immunosuppressive therapy that would otherwise be administered in the absence of administering the conjugate. This is significant, as this type of immunotherapy is toxic. Accordingly, the invention provides methods of treating lupus nephritis wherein a conjugate as described herein (such as LJP 394) is administered in an amount sufficient to reduce the amount of corticosteroid or cyclophosphamide administered to the individual as compared to using corticosteroid or cyclophosphamide without administering the conjugate. In some embodiments, the incidence of renal flares are reduced in the individual and the conjugate is administered in an amount sufficient to effect this reduction. The invention also provides methods of treating SLE, preferably lupus nephritis, comprising administering a (any) conjugate described herein in conjunction with corticosteroid and/or cyclophosphamide. The conjugate is administered in an amount effective to reduce antibody affinity for the epitope in the conjugate. Preferably, the conjugate is LJP 394. Methods of administering corticosteroid and/or cyclophosphamide are known in the art. Reducing the dosage of corticosteroid and/or cyclophosphamide therapy (which reduces the dependence on administration of these drugs and in effect delays administration of these drugs) can be assessed by, for example, comparing to known and/or established averages of dosage (in terms of amount and/or intervals) generally given over time which are known in the art.

Methods of Screening

The invention also provides methods of identifying individuals who may be suitable to receive (and/or to continue to receive) the treatments described herein, or, in alternative embodiments, methods of identifying individuals who may be unsuitable to receive (and/or to continue to receive) the treatments described herein, based on antibody affinities.

Accordingly, in some embodiments, the invention provides methods of identifying an individual who may be suitable for treatment for SLE, said treatment comprising administration of a conjugate comprising (a) a non-immunogenic valency platform molecule and (b) two or more dsDNA epitopes, preferably polynucleotides which specifically bind to an antibody from the individual which specifically binds to double stranded DNA, said polynucleotide (if a polynucleotide is used) comprising, consisting essentially of or consisting of the (ds) sequence 5'-GTGTGTGTGTGTGTGTGTGT-3' (SEQ ID NO:1), said method comprising measuring the apparent equilibrium dissociation constant ($K_D$') for the polynucleotide in (or of) conjugate before or upon initiation of treatment and anti-double stranded DNA antibodies from the individual, wherein an individual is identified by $K_D$' (or its functional equivalent) of less than about 1.0 mg IgG per ml. In other embodiments, the $K_D$' is less than about any of the following: 0.8; 0.7; 0.6; 0.5; 0.4; 0.3; 0.2; 0.1; 0.09; 0.08; 0.07; 0.06 0.05; 0.025. The invention thus provides screening based on any of a number of dsDNA epitopes contemplated for use in treatment. Generally, a higher affinity "cut-off" (for example, as indicated by a lower $K_D$' value) would provide a higher degree of certainty with respect to likely success of treatment.

In other embodiments, the invention provides methods of identifying an individual who may be unsuitable for treatment for SLE, said treatment comprising administration of a conjugate comprising (a) a non-immunogenic valency platform molecule and (b) two or more dsDNA epitopes, preferably polynucleotides which specifically bind to an antibody from the individual which specifically binds to double stranded DNA, said polynucleotide (if used) comprising, consisting essentially of or consisting of the (ds) sequence 5'-GTGTGTGTGTGTGTGTGTGT-3' (SEQ ID NO:1), said method comprising measuring the apparent equilibrium dissociation constant ($K_D$') for the polynucleotide in (or of) conjugate and anti-double stranded DNA antibodies from the individual before or upon initiation of treatment, wherein an individual is identified by $K_D$' of more than about 1.0 mg IgG per ml. In other embodiments, the individual is identified by a $K_D$' of more than about 0.8 mg IgG per ml. If expressed as a range, the upper limit may be any number, including, but not limited to, about 2.0, about 3.0, about 5.0, about 10, about 15, about 20.

The invention also provides methods of monitoring treatment for SLE in an individual, said treatment comprising administration of a conjugate comprising (a) a non-immunogenic valency platform molecule and (b) two or more dsDNA epitopes, preferably polynucleotides which specifically bind to an antibody from the individual which specifically binds to double stranded DNA, said method comprising measuring the affinity (for example, the apparent equilibrium dissociation constant ($K_D$')) of the conjugate or dsDNA epitope (such as polynucleotide) and anti-double stranded DNA antibodies from the individual. For these methods, a change in $K_D$' (compared to initial $K_D$') generally indicates that the treatment may be continued (i.e., that the treatment will be efficacious). The change in $K_D$' may be at least about any of the changes described herein (generally from at least about 20% to at least about 500%), with measurement(s) generally, but not necessarily, at least two to six weeks apart. A change over any two given measurements (whether or not sequential) may be used. For example, if measurement at two weeks shows no change, but comparison of the measurement at four weeks shows a change, continuation of treatment may be indicated. Treatment could also be continued if $K_D$' does not change or even changes indicating an increase in affinity, as such developments (including no change) could be temporary. Alternatively, a change in affinity (such as $K_D'$) need not be tested for or observed. For example, affinity could be measured and compared to that from a general population (e.g., an average affinity). Thus, with respect embodiments directed to methods of monitoring treatment, a particular result need not be observed for these methods to be practiced, although certain results (or ranges of results) may be desirable and can be used.

In some embodiments, an individual is selected for treatment based on a percentile ranking of affinity compared to a population. For example, there is a range of antibody affinities over a given patient population, and individuals suitable for treatment (or, conversely, individuals likely to be unsuitable) can be identified based on a percentile ranking of antibody affinity with respect to this population. Accordingly, in some embodiments, an individual is included in treatment, or identified as suitable to receive treatment, if the antibody affinity for that individual is in about the top 80% of affinities for that population (conversely, individuals are generally not suitable to receive treatment if they are in about the bottom 20% of affinities for that population). In other embodiments, an individual is included in treatment, or identified as suitable to receive treatment, if the antibody for that individual is in about the top 50% of affinities for that population (conversely, individuals are generally not suitable to receive treatment if they are in about the bottom 50% of affinities for that population). In some embodiments, the antibody in that individual is in about any of the top percentages: 30%; 25%; 20%; 10%; 5%. A population may be about, or alternatively at least about any of the following, in terms of number of individuals measured: 10, 15, 20, 25, 30, 50, 60, 75, 100, 125, 150, 175, 200, 225, 250, 300, 400, 500. Preferably, a sufficient number of individuals are measured to provide a statistically significant population, which can be determined by methods known in the art. An upper limit of a population may be any number, including those listed.

Generally, an individual is suitable to receive the treatments (or to continue to receive the treatments) described herein if, after administering the conjugate(s) in an amount sufficient and for a time sufficient to elicit a response in terms of reducing antibody affinity, the individual's antibody affinity decreases at least about any 20% with respect to antibody affinity before administration of conjugate. For example, a 20% reduction in antibody affinity is reflected in a change of an initial $K_D'$ of 0.4 to a $K_D'$ of 0.5. In other embodiments, the individual's antibody affinity decreases by at least about 50%. In other embodiments, the individual's antibody affinity decreases by at least about 75%. Based on our observations in the context of lupus treatments, at least about 8 weeks, preferably at least about 10 weeks, more preferably at least about 12 weeks, should be a sufficient time to observe a measurable response. Lack of a measurable change in affinity over this time period indicates that the individual receiving the treatment is unlikely to benefit from such treatment, in terms of reduction of symptoms.

Generally, a response is indicated (and therefore continuation of treatment is indicated) if there is a statistically significant change (reduction) compared to the initial affinity (i.e., affinity measured before or upon initiation of treatment). A statistically significant change depends upon the particular assay used, and this value is generally readily obtainable. For an assay using surface plasmon resonance, a reduction in affinity of at least about 15%, preferably at least about 20%, more preferably at least about 25%, more preferably at least about 40%, more preferably at least about 50% indicates responsiveness and that continuation treatment is indicated. For a competitive Farr assay, the same reductions in affinity generally apply. For other assays, the change can be at least about any of the above percentages, and further can be at least about any of the following percentages: 75%, 100%, 150%, 200%, 250%, 300%, 350%, 400%, 450%, 500%.

The invention also provides methods of identifying antibody affinity (as reflected by $K_D'$ and/or its equivalent) which may be a suitable "cut-off" value for selection of an individual to receive a treatment(s) described herein. As is evident from the experimental data provided herein, a population of individuals may be assessed for initial affinity compared to affinity after initiation of treatment (given a sufficient amount of conjugate and sufficient time to produce a response, if any, as indicated by reduction (if any) in affinity). Initial affinity value(s) which indicate a response (in terms of reduction of affinity and/or palliation of disease) is then determined and can be used as an indicator for selection of an individual to receive treatment (as described herein).

Accordingly, the invention provides a method of identifying an antibody affinity which may indicate applicability (or use) of a treatment for an antibody-mediated pathology, said method comprising (a) measuring affinity of antibodies implicated in the antibody-mediated pathology from a plurality of individuals (preferably measuring the affinity for each individual), said individuals having an antibody-mediated pathology, said affinity being between said antibodies and an analog of an immunogen implicated in the antibody-mediated pathology; (b) administering to the plurality of individuals the molecule comprising the analog; (c) correlating the extent of the antibody-mediated pathology with the initial affinity. Generally, a positive correlation between an affinity and a reduction of symptoms (or some other suitable clinical endpoint) indicates that the antibody affinity is predictive of suitability of that treatment. Conversely, a negative correlation indicates that individuals having that affinity (or lower) may be unsuitable for the treatment. For these methods, the molecule comprising an analog may be any platform described herein. In some embodiments, the analog lacks cell epitopes capable of activating T cells in an individual. In some embodiments, the correlation is between the extent of change in antibody affinity with extent of disease, and, accordingly, clinically significant initial antibody affinity and/or change in antibody affinity is identified.

Measuring Antibody Affinity

Antibody affinity may be measured using methods known in the art which assess degree of binding of DNA epitope to antibody. Generally, these methods comprise competition assays and non-competition assays. With respect to polynucleotide epitopes (which will be used in a conjugate to be administered), affinity may be measured using polynucleotide alone or polynucleotide-containing conjugates (as long as the polynucleotide and conjugate give equivalent, or at least convertible, values).

In a competition assay, varying concentrations of antibody or epitope are reacted with epitope or antibody, and results may be expressed in terms of amount of antibody (generally in terms of concentration) required to reach half-maximal binding, generally designated as $IC_{50}$.

Another convenient way to express affinity is apparent equilibrium dissociation constant, or $K_D'$, which reflects the titer-weighted average affinity of the antibody for the antibody-binding epitope on the conjugate. Antibody is generally obtained from whole blood and measured, by plasma, serum, or as an IgG fraction, and the affinity of this fraction for the conjugate is measured. Methods of obtaining IgG fractions are known in the art and are described herein. One preferred way to measure affinity is to measure $K_D'$ based on a surface plasmon resonance assay as described in the Examples.

Another way to measure affinity is by kinetic (i.e., non-equilibrium) analysis, methods of which are known in the art. Preferably, rate of dissociation (i.e., off rate) of antibody from epitope is measured.

Treatment Modalities

For purposes of this invention, the treatment methods used entail a conjugate comprising an non-immunogenic valency platform molecule and at least two (i.e., two or more) dsDNA epitopes, preferably polynucleotides which bind to anti-dsDNA antibody from the individual. Preferably, the polynucleotide is double stranded DNA, preferably the sequence 5'-GTGTGTGTGTGTGTGTGTGT-3' (SEQ ID NO: 1). In some embodiments, the polynucleotide comprises this sequence $((GT)_{10})$, or consists essentially of this sequence.

For the methods of treatment, a conjugate is administered in an amount sufficient to effect a decrease in antibody affinity, preferably in an amount sufficient to effect reduction of one or more symptoms associated with lupus (especially lupus nephritis). For LJP 394, the conjugate is generally administered at least about 50 mg, preferably at least about 100 mg, once a week, although, as discussed above, dosage could vary depending on affinity of antibody from an individual.

dsDNA Epitope

Double-stranded DNA (dsDNA) epitopes for use in the conjugates of the present invention may be any chemical moiety which specifically binds to a dsDNA antibody. In particular, epitopes of interest include those that bind the anti-polynucleotide (particularly anti-double stranded DNA) antibodies that occur in systemic lupus erythematosis. Generally, but not necessarily, the dsDNA epitopes used are polynucleotides, preferably DNA (including DNA analogs).

Examples of suitable epitopes include, but are not limited to, those that bind to lupus anti-DNA antibodies (see U.S. Pat. Nos. 5,162,515; 5,391,785; 5,276,013; 5,786,512; 5,726,329; 5,552,391; 5,268,454; 5,633,395; 5,606,047).

The suitability of particular epitopes for binding antibodies according to this invention can be identified and/or confirmed using techniques known in the art and described herein. For example, to select the optimum epitope from a library of small drug molecules believed to mimic the dsDNA epitope for SLE, a family of platforms can be constructed in which each of the candidates is alternatively displayed on a similar platform molecule. The composition is then tested for efficacy. For example, for in vivo use, an animal model is used in which there are circulating antibodies of the undesired type, such as, for example, the BXSB mouse model system. The animals can be immunized with an appropriate epitope to initiate the antibody response, if necessary. Test candidates assembled onto a platform are then used to treat separate animals, either by administration, or by ex vivo use, according to the intended purpose. The animals are bled before and after treatment, and the antibody levels in plasma are determined by standard immunoassay as appropriate for the specific antibody. Efficacy of the candidates is then assessed according to antibody affinity assays designed to indicate antibodies specific for the epitope being tested. Appropriate affinity assays are described herein.

Polynucleotides may be screened for binding activity with antisera containing the antibodies of interest, for example, SLE antisera, by the assays described in the examples and known in the art. Examples of such assays include competitive affinity assays, for example, a competitive Farr assay and/or a competitive ELISA assay, and/or non-competitive, equilibrium affinity assay, such as the surface plasmon resonance (for example, using BIACORE®) based assay described herein.

A competitive Farr assay in which binding activity may be expressed as $IC_{50}$ (the polynucleotide concentration in molar nucleotides resulting in half-maximal inhibition) is an exemplary assay. Polynucleotide duplexes having an $IC_{50}$ of less than about 500 nM, preferably less than 50 nM, are deemed to have significant binding activity and are, therefore, useful for making the conjugates of this invention.

Another appropriate assay is the non-competitive, equilibrium affinity assay described herein, in which a titer-weighted affinity is determined.

It is understood that, for purposes of this invention, more than one type of dsDNA epitope(s) may be used in preparing a conjugate. Alternatively, one type (i.e., one chemical species) of an dsDNA epitope may be used. If a polynucleotide (such as ds DNA) is used, generally the length is greater than about 10 base pairs (bp), more preferably greater than about 15 bp, more preferably greater than or equal to about 20 bp. Generally, but not necessarily, the length is less than about 1 kb, preferably less than about 500 bp, preferably less than about 100 bp.

Valency Platform Molecules

Any of a variety of non-immunogenic valency platform molecules (also called "platforms") may be used in the conjugates of the invention. Many have been described in the art, such as polymers, and need not be described herein. Preferably, the conjugates comprise a chemically defined valency platform molecule in which a precise valency (as opposed to an average) is provided. Accordingly, a defined valency platform is a platform with defined structure, thus a defined number of attachment points and a defined valency. Certain classes of chemically defined valency platforms, methods for their preparation, conjugates comprising them and methods for the preparation of such conjugates suitable for use within the present invention include, but are not limited to, those described in the U.S. Pat. Nos. 5,162,515; 5,391,785; 5,276,013; 5,786,512; 5,726,329; 5,268,454; 5,552,391; 5,606,047; and 5,663,395 and in commonly-owned U.S. Ser. Nos. 60/111,641 (U.S. Ser. No. 09/457,607 and PCT App. No. PCT/US99/29339) and 60/138,260 (U.S. Ser. No. 09/590,592 and PCT App. No. PCT/US00/15968), all of which are hereby incorporated by reference.

A platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159–168; Dumas et al. (1995) *Arch. Dematol. Res.* 287:123–128; Borel et al. (1995) *Int. Arch. Allergy Immunol.* 107:264–267; Borel et al. (1996) *Ann. N. Y. Acad. Sci.* 778:80–87.

The valency of a chemically-defined valency platform molecule within the present invention can be predetermined by the number of branching groups added to the platform molecule. Suitable branching groups are typically derived from diamino acids, triamines, and amino diacids.

Preferred valency platform molecules are biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 200,000, preferably about 200 to about 50,000 (or less, such as 30,000). Examples of valency platform molecules within the present invention are polymers (or are comprised of polymers) such as polyethylene glycol (PEG), poly-D-lysine, polyvinyl alcohol, polyvinylpyrrollidone, D-glutamic acid and D-lysine (in a ratio of 3:2). Preferred polymers are based on polyethylene glycols (PEGs) having a molecular weight of about 200 to about 8,000. Other suitable platform molecules for use in the conjugates of the invention are albumin and IgG.

Preferred valency platform molecules suitable for use within the present invention are the chemically-defined, non-polymeric valency platform molecules disclosed in co-owned U.S. Pat. No. 5,552,391, hereby incorporated by reference. Particularly preferred homogeneous chemically-defined valency platform molecules suitable for use within the present invention are derivatized 2,2'-ethylenedioxydiethylamine (EDDA) and triethylene glycol (TEG). The AHAB-TEG platform used for LJP 394 is described below.

Preferred platforms for dsDNA epitopes are tetrabromoacetyl compounds, and other tetravalent and octavalent valency platform molecules, such as those described in Jones et al. (1995) *J. Med Chem.* 38:2138–2144; and U.S. Patent references provided above.

Additional suitable valency platform molecules include, but are not limited to, tetraaminobenzene, heptaaminobetacyclodextrin, tetraaminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

For purposes of this invention, the valency platform molecules have a minimum valency of at least two, preferably at least four, preferably at least six, more preferably at least eight, preferably at least 10, preferably at least 12. As an upper limit, valency is generally less than 128, preferably less than 64, preferably less than 35, preferably less than 30, preferably less than 25, preferably less than 24, preferably less than 20, although the upper limit may exceed 128. Conjugates may also have valency of ranges of any of the lower limits of 2, 4, 6, 8, 10, 12, 16, with any of the upper limits of 128, 64, 35, 30, 25, 24, 20.

In some embodiments, the valency platform molecule comprises a carbamate linkage, i.e., —O—C(=O)—N<). Such platforms are described in a co-owned patent application entitled "Valency Platform Molecules Comprising Carbamate Linkages" U.S. Ser. No. 60/111,641 (U.S. Ser. No. 09/457,607 and PCT App. No. PCT/US99/29339), hereby incorporated by reference.

In other embodiments, valency platforms may be used which, when conjugated, provide an average valency (i.e., these platforms are not precisely chemically defined in terms of their valency). Examples of such platforms are polymers such as linear PEG; branched PEG; star PEG; polyamino acids; polylysine; proteins; amino-functionalized soluble polymers.

Conjugation of dsDNA Epitope(s) with Valency Platform Molecules

Conjugation of a biological or synthetic molecule to the chemically-defined platform molecule may be effected in any number of ways, typically involving one or more crosslinking agents and functional groups on the biological or synthetic molecule and valency platform molecule. Examples of standard chemistry which may be used for conjugation include, but are not limited to: 1) thiol substitution; 2) thiol Michael addition; 3) amino alkyation; 4) disulfide bond formation.

The synthetic polynucleotide duplexes that are coupled to the valency platform molecule are composed of at least about 20 bp and preferably 20–50 bp. Polynucleotides described herein are deoxyribonucleotides unless otherwise indicated and are set forth in 5' to 3' orientation. Preferably the duplexes are substantially homogeneous in length; that is, the variation in length in the population will not normally exceed about ±20%, preferably ±10%, of the average duplex length in base pairs. They are also preferably substantially homogeneous in nucleotide composition; that is, their base composition and sequence will not vary from duplex to duplex more than about 10%. Most preferably they are entirely homogeneous in nucleotide composition from duplex to duplex.

Based on circular dichroic (CD) spectra interpretation, duplexes that are useful in the invention assume a B-DNA type helical structure. It should be understood that it is not intended that the invention be limited by this belief and that the duplexes may, upon more conclusive analysis assume Z-DNA and/or A-DNA type helical structures.

These polynucleotide duplexes may be synthesized from native DNA or synthesized by chemical or recombinant techniques. Naturally occurring or recombinantly produced dsDNA of longer length may be digested (e.g., enzymatically, chemically and/or by mechanical shearing) and fractionated (e.g., by agarose gel or Sephadex™ column) to obtain polynucleotides of the desired length.

Alternatively, pairs of complementary single-stranded polynucleotide chains up to about 70 bases in length are readily prepared using commercially available DNA synthesizers and then annealed to form duplexes by conventional procedures. Synthetic dsDNA of longer length may be obtained by enzymatic extension (5'-phosphorylation followed by ligation) of the chemically produced shorter chains.

The polynucleotides may also be made by molecular cloning. For instance, polynucleotides of desired length and sequence are synthesized as above. These polynucleotides may be designed to have appropriate termini for ligation into specific restriction sites. Multiple iterations of these oligomers may be ligated in tandem to provide for multicopy replication. The resulting construct is inserted into a standard cloning vector and the vector is introduced into a suitable microorganism/cell by transformation. Transformants are identified by standard markers and are grown under conditions that favor DNA replication. The polynucleotides may be isolated from the other DNA of the cell/microorganism by treatment with restriction enzymes and conventional size fractionation (e.g., agarose gel, Sephadex™ column).

Alternatively, the polynucleotides may be replicated by the polymerase chain reaction (PCR) technology. Saiki et al (1985) *Science* 230:1350–1354; Saiki et al. (1988) *Science* 239:487–491; Sambrook et al. (1989) p 14.1–14.35.

The polynucleotides are conjugated to the chemically-defined valency platform molecule in a manner that preserves their antibody binding activity. This is done, for example, by conjugating the polynucleotide to the valency platform molecule at a predetermined site on the polynucleotide chain such that the polynucleotide forms a pendant chain of at least about 20 base pairs measured from the conjugating site to the free (unattached) end of the chain.

In one embodiment, the polynucleotide duplexes are substantially homogenous in length and one strand of the duplex is conjugated to the valency platform molecule either directly or via a linker molecule. Synthetic polynucleotides may be coupled to a linker molecule before being conjugated to a valency platform molecule. Usually the linker containing strand of the duplex is coupled at or proximate (i.e., within about 5 base pairs) to one of its ends such that each strand forms a pendant chain of at least about 20 base pairs measured from the site of attachment of the strand to the linker molecule. The second strand is then annealed to the first strand to form a duplex. Thus, a conjugate within the present invention may be generally described by the following formula:

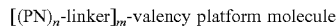

[(PN)$_n$-linker]$_m$-valency platform molecule wherein PN=a double-stranded polynucleotide with "n" nucleotides, wherein n=at least about 20 and m=2–8.

In one embodiment, the polynucleotides of the conjugates are coupled to a linker molecule at or proximate one of their ends. The linker molecule is then coupled to the chemically-defined valency platform molecule. As described in U.S. Pat. No. 5,552,391 and incorporated herein by reference, exemplary of suitable linker molecules within the present invention are 6 carbon thiols such as HAD, a thio-6 carbon chain phosphate, and HAD$_p$ S, a thio-6 carbon chain phosphorothioate. Chemically-defined valency platform molecules within the present invention are formed, for example, by reacting amino modified-PEG with 3,5-bis-(iodoacetamido) benzoyl chloride (hereinafter "IA-DABA"); 3-carboxypropionamide-N,N-bis-[(6'-N'-carbobenzyloxyaminohexyl)acetamide] 4"-nitrophenyl ester (hereinafter "BAHA"); 3-carboxypropionamide-N,N-bis-[(8'-N'-carbobenzyloxyamino-3',6'-dioxaoctyl)acetamide] 4"-nitrophenyl ester (hereinafter "BAHA$_{ox}$"); or by reacting PEG-bis-chloroformate with N,N-di(2-[6'-N'-carbobenzyloxyaminohexanoamido]ethyl)amine (hereinafter "AHAB") to form chemically-defined valency platform molecules.

For example, a defined double-stranded polynucleotide (PN) can be conjugated to a valency platform molecule by first providing a single chain consisting of approximately 20 alternating cytosine (C) and adenosine (A) nucleotides. Four CA chains may then be covalently conjugated through linkers such as HAD to four reactive sites on a derivatized platform molecule such as triethylene glycol. The valency platform molecule is synthesized to include groups such as bromoacetyl. During the conjugation, a leaving group is displaced by sulfur. A second single nucleotide chain consisting of approximately 20 alternating thymidine (T) and guanosine (G) nucleotides can then be annealed to the CA strand to form a double-stranded PN conjugate of the formula, [(PN)$_{20}$-linker]$_4$ -valency platform molecule.

Alternatively, in another embodiment, the polynucleotide may be coupled to the derivatized valency platform molecule at the 3' end of the polynucleotide via a morpholino bridge formed by condensing an oxidized 3' terminal ribose on one of the strands of the polynucleotide with a free amino group on the derivatized platform molecule and then subjecting the adduct to reducing conditions to form the morpholino linkage, as described in U.S. Pat. No. 5,553,391. Such coupling requires the derivatized platform molecule to have at least an equal number of amino groups as the number of polynucleotide duplexes to be bound to the platform molecule. The synthesis of such a conjugate is carried out in two steps. The first step is coupling one strand of the polynucleotide duplex to the derivatized platform molecule via a condensation/reduction reaction. The oxidized 3' terminal ribose is formed on the single polynucleotide strand by treating the strand with periodate to convert the 3' terminal ribose group to an oxidized ribose group. The single-stranded polynucleotide is then added slowly to an aqueous solution of the derivatized platform molecule with a pH of about 6.0 to 8.0 at 2–8° C.

The molar ratio of polynucleotide to platform molecule in all the conjugation strategies will normally be in the range of about 2:1 to about 30:1, usually about 2:1 to about 8:1 and preferably about 4:1 to 6:1. In this regard, it is preferable that the conjugate not have an excessively large molecular weight as large molecules, particularly those with repeating units, of m.w. >200,000 may be T-independent immunogens. See Dintzis et al. (1983) *J. Immunol.* 131:2196 and Dintzis et al. (1989) *J. Immunol.* 143:1239. During or after the condensation reaction (normally a reaction time of 24 to 48 hr), a strong reducing agent, such as sodium cyanoborohydride, is added to form the morpholino group. The complementary strand of the duplex is then added to the conjugate and the mixture is heated and slowly cooled to cause the strands to anneal. The conjugate may be purified by gel permeation chromatography.

An alternative to the ribose strategy is forming aldehyde functionalities on the polynucleotides and using those functionalities to couple the polynucleotide to the platform molecule via reactive functional groups thereon. Advantage may be taken of the fact that gem vicinal diols, attached to the 3' or 5' end of the polynucleotide, may be oxidized with sodium periodate to yield aldehydes which can condense with functional amino groups of the platform molecule. When the diols are in a ring system, e.g., a five-membered ring, the resulting condensation product is a heterocyclic ring containing nitrogen, e.g., a six-membered morpholino or piperidino ring. The imino-condensation product is stabilized by reduction with a suitable reducing agent; e.g., sodium borohydride or sodium cyanoborohydride. When the diol is acyclic, the resulting oxidation product contains just one aldehyde and the condensation product is a secondary amine.

Another procedure involves introducing alkylamino or alkylsulfhydryl moieties into either the 3' or 5' ends of the polynucleotide by appropriate nucleotide chemistry, e.g., phosphoramidite chemistry. The nucleophilic groups may then be used to react with a large excess of homobifunctional cross-linking reagent, e.g., dimethyl suberimidate, in the case of alkylamine derivatives, or an excess of heterobifunctional cross-linking reagent, e.g., m-maleimidobenzoyl-N-hydroxysuccinimide ester (MBS) or succinimidyl (4-iodoacetyl) aminobenzoate (SIAB), for the alkylsulfhydryl derivatives. Once excess cross-linker is removed, the polynucleotide derivatives are reacted with amino groups on the platform molecule. Alternatively, the sulfhydryl group may be reacted with an electrophilic center on the platform, such as a maleimide or α-haloacetyl group or other appropriate Michael acceptor.

Still another strategy employs modified nucleosides. Suitable deoxynucleoside derivatives can be incorporated, by standard DNA synthetic chemistry, at desired positions in the polynucleotide, preferably on the 5' or 3' ends. These nucleoside derivatives may then react specifically and directly with alkylamino groups on the platform molecule. Alternatively, side reactions seen with the above-described dialdehyde chemistry, such as amine catalyzed beta-elimination, can be circumvented by employing appropriate nucleoside derivatives as the 3' terminus of the chain to be attached. An example of this is 5' methylene extension of ribose; i.e., a 5' (2-hydroxyethyl)-group instead of a 5' hydroxymethyl group. An alternative would be to use a phosphonate or phosphinate linkage for the 3' terminal dinucleotide of the polynucleotide to be attached to the platform molecule.

A description of the synthesis of the conjugate LJP 394, a tetravalent conjugate, is described in Jones et al. (1995) and in U.S. Pat. No. 5,552,391, which are hereby incorporated by reference. LJP 394 comprises four 20-mer oligonucleotides consisting of alternating C and A nucleotides, $(CA)_{10}$, attached to a platform and annealed with complementary 20-mer oligonucleotides consisting of alternating G and T nucleotides, $(GT)_{10}$, oligonucleotide. The valency platform molecule used in LJP 394 is shown immediately below.

weight, preferably about 150 μg to about 5 mg/kg body weight, preferably about 250 μg to about 1 mg conjugate/kg body weight. Empirical considerations, such as the half life, generally will contribute to determination of the dosage. Other dosages, such as about 50 to 100 mg per week, are also described herein. If used as a toleragen, conjugate may be administered daily, for example, in order to effect antibody clearance (pheresis), followed by less frequent administrations, such as two times per week, once a week, or even less frequently. Frequency of administration may be determined and adjusted over the course of therapy, and is based on maintaining tolerance (i.e., reduced or lack of immune response to dsDNA). Other appropriate dosing schedules may be as frequent as continuous infusion to daily or 3 doses per week, or one dose per week, or one dose every two to four weeks, or one dose on a monthly or less frequent schedule depending on the individual or the disease state. Repetitive administrations, normally timed according to B cell turnover rates, may be required to achieve and/or maintain a state of humoral anergy. Such repetitive administrations generally involve treatments of about 1 μg to about

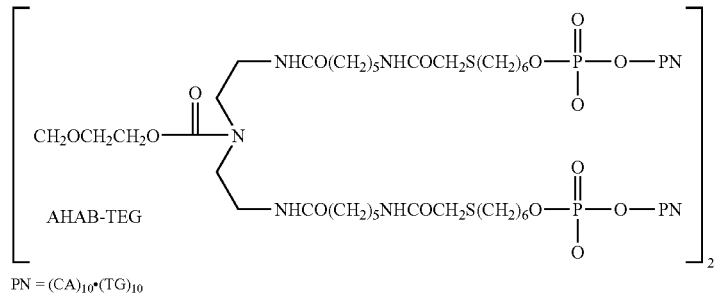

$PN = (CA)_{10}\cdot(TG)_{10}$

Administration of Conjugates

Various formulations of epitope-presenting conjugate(s) may be used for administration. In some embodiments, the epitope-presenting conjugate(s) may be administered neat. In some embodiments, the compositions comprise a conjugate(s) and a pharmaceutically acceptable excipient, and may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington's Pharmaceutical Sciences* 19th Ed. Mack Publishing (1995).

Generally, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like. Generally, the conjugate will normally constitute about 0.01% to 10% by weight of the formulation due to practical, empirical considerations such as solubility and osmolarity. The particular dosage regimen, i.e., dose, timing and repetition, will depend on the particular individual and that individual's medical history. Generally, a dose of about 1 μg to about 100 mg conjugate/kg body weight, preferably about 100 μg to about 10 mg/kg body 10 mg/kg body weight or higher every 30 to 60 days, or sooner, if an increase in anti-dsDNA antibody level is detected. Alternatively, sustained continuous release formulations of the compositions may be appropriate. Various formulations and devices for achieving sustained release are known in the art.

Other formulations include those suitable for oral administration, which may be suitable if the conjugate is able to cross the mucosa. Similarly, an aerosol formulation may be suitable.

Other formulations include suitable delivery forms known in the art including, but not limited to, carriers such as liposomes. Mahato et al. (1997) *Pharm. Res.* 14:853–859. Liposomal preparations include, but are not limited to, cytofectins, multilamellar vesicles and unilamellar vesicles.

In some embodiments, more than one conjugate may be present in a composition. Such compositions may contain at least one, at least two, at least three, at least four, at least five different conjugates. Such "cocktails", as they are often denoted in the art, may be particularly useful in treating a broader range of population of individuals. They may also be useful in being more effective than using only one (or fewer than are contained in the cocktail) conjugate(s).

The compositions may be administered alone or in conjunction with other forms of agents that serve to enhance and/or complement the effectiveness of a conjugate of the invention, including, but not limited to, anti-helper T cell treatments. Such treatments usually employ agents that suppress T cells such as steroids or cyclosporin. Another agents are corticosteroid and/or cyclophosphamide immunosuppressive therapy.

Detection and measurement of indicators of efficacy are generally based on measurement of anti-double-stranded DNA antibody and/or clinical symptoms associated with SLE, which are known in the art.

Lupus nephritis (kidney glomerulonephritis or kidney inflammation) is characterized by a progressive loss of kidney function culminating in renal failure. Lupus nephritis is characterized by hematuria, decreased urine output, elevated blood urea nitrogen levels, elevated serum creatinine levels, hypertension, and proteinuria. Accordingly, these parameters can be monitored as a means of monitoring kidney degeneration.

Compositions of the Invention

Kits comprising epitopes which bind to anti-ds DNA antibodies

The invention also provides kits for measuring antibody affinities for use in the methods described herein, particularly affinity for an epitope which binds to anti-ds DNA antibodies. Accordingly, the invention includes kits containing (i.e., comprising) one or more dsDNA epitopes, preferably polynucleotides (preferably, double stranded (ds) DNA molecules) comprising an epitope which binds to an anti-ds DNA antibody from an individual (and the epitope-containing polynucleotide binds to an anti-ds DNA antibody from an individual). Accordingly, the kits comprise a molecule or moiety comprising a ds DNA epitope, such as any described herein. In one embodiment, the kit comprises a polynucleotide with (comprising) the sequence (or, alternatively, consisting essentially of or consisting of the sequence) 5'-GTGTGTGTGTGTGTGTGTGT-3' (SEQ ID NO: 1). Kits comprising a polynucleotide(s) or any other suitable ds DNA epitope may further include instructions for using the polynucleotide to detect affinity of an individual's anti-ds DNA antibody(ies) for the polynucleotide (or ds DNA epitope). In other embodiments, the kits comprise the conjugates described herein, with instructions for using the conjugate to detect affinity of an individual's anti-ds DNA antibodies for the conjugate. Preferably, the conjugate is LJP 394.

The kits may be used, for example, to test an individual to determine if the individual is suitable or unsuitable for treatment with the conjugate(s), as well as for monitoring purposes. The kits may also be used in determining affinity cut-off values (i.e., affinity values which correlate with clinical results). The kits of this invention are in suitable packaging, and may optionally provide additional components such as, buffers and instructions for determining affinity or binding to anti-dsDNA antibody, such as capture reagents, developing reagents, labels, reacting surfaces, means for detection, control samples, and interpretive information. The instructions may be for any measurement of antibody affinity, including, but not limited to, those assays described herein. Accordingly, in some embodiments, the instructions are for determining affinity using surface plasmon resonance. In other embodiments, the instruction are for determining affinity using direct binding assays and/or Farr assays. In some embodiments, reagents described above are supplied such that multiple measurements may be made, such as allowing for measurements in the same individual over time or multiple individuals.

Generally, the dsDNA epitope(s) of the kit, preferably a polynucleotide(s) of the kit (whether in free form or attached to a conjugate or other matrix), contains, or alternatively consists of, the epitope that will be or is used in treatment, or has been demonstrated to have about the same affinity for an individual's anti-ds DNA antibodies as the epitope(s) that will be used in treatment. In other embodiments, the kits comprising a ds DNA epitope whose affinity for anti-dsDNA antibodies mimics or alternatively can be correlated to that of the dsDNA epitope to be used in treatment, such as 5'-GTGTGTGTGTGTGTGTGTGT-3' (SEQ ID NO: 1). These dsDNA epitopes can be used as "proxies" for the ds DNA epitope to be used in treatment, such as LJP 394, in assessing antibody affinity for the methods described herein.

Any appropriate means for detecting binding of the antibodies may be employed (and provided in the kits) such as a labeled anti-human antibody, when the presence of human anti-dsDNA antibodies is tested, wherein the label may be an enzyme, fluorophore, chemiluminescent material radioisotope or coenzyme. Generally, the label used will be an enzyme. Accordingly, in some embodiments, the kit(s) of the invention further comprises a label. In some embodiments, the polynucleotide in the kit(s) is conjugated to biotin. In a preferred embodiment, the dsDNA epitope (such as a polynucleotide, for example, double stranded DNA) is biotinylated. Biotinylation may also be accomplished using commercially available reagents (i.e., Pharmacia; Uppsala, Sweden). In another preferred embodiment, the biotinylated dsDNA epitope comprises, consists essentially or, or consists of is 5'-GTGTGTGTGTGTGTGTGTGT-3' (SEQ ID NO:1).

In other embodiments, the invention provides a kit comprising (a) a conjugate as described herein, such as LJP 394; and (b) a polynucleotide (or other ds DNA epitope) used in the conjugate, or, alternatively, a polynucleotide comprising the polynucleotide used in the conjugate (or a molecule or moiety comprising the epitope to be used in the conjugate). When used for affinity measurements, the conjugate and/or polynucleotide may be biotinylated. In some embodiments, the kit contains instructions for administering the conjugate to an individual as well as instructions for using the conjugate and/or the polynucleotide (including a polynucleotide comprising the polynucleotide used in the conjugate) for detecting affinity for an antibody in an individual which binds to ds DNA as described herein. As discussed herein, a combination of a conjugate to be used for treatment and a molecule comprising a ds DNA epitope, the binding activity or affinity of which mimics, or can be correlated with, the epitope of the conjugates is used in the kits.

In other embodiments, the invention provides a kit comprising an analog which binds to an antibody implicated in an antibody mediated pathology. In some embodiments, the invention provides a kit comprising a molecule comprising an epitope which binds to an antibody implicated in an antibody-mediated pathology. These kits, also useful for making affinity determinations, are in suitable packaging and optionally include instructions for using the analog or molecule in the kit to determine affinity of an antibody implicated in an antibody-mediated pathology with the analog or epitope-containing molecule. Peptide analogs which bind to antibodies implicated in antiphospholipid syndome (APS) and lupus are disclosed in WO 96/40197 and WO 97/46251. Polypeptides which bind to antibodies implicated in antibody-mediated pathology having specificity for domain 1 of $\beta_2$GPI are disclosed in commonly owned U.S. Ser. No. 09/328,199 (PCT/US99/13194). Other analogs and epitope-containing molecules are known in the art. In another embodiment, the kit comprises D-galactopyranoside, or, alternatively, a molecule which exhibits specific binding to an anti-αGal (galactose α1,3 galactosyl) antibody and instructions and/or reagents for determining antibody affinity.

The following Examples are provided to illustrate but not limit the invention.

EXAMPLES

Example 1

Inhibition of Binding of Anti-dsDNA Antibodies to DNA by LJP 394

After determining the presence of anti-ds DNA antibodies in patients using a Farr assay, a competitive Farr assay was used to measure the affinity of anti-dsDNA antibodies found in sera from patients with SLE to LJP 394. In addition, the assay was used to measure the affinity of anti-dsDNA antibodies found in sera from three animals models of SLE (BXSB mice, NZB×NZW $F_1$ mice, and MRL/1pr mice).

The Farr assay used $^{125}$I-labeled recombinant dsDNA (Diagnostic Products Corporation, Los Angeles, Calif.) that was combined with the anti-dsDNA antibodies found in sera from patients with SLE or from the mouse models of SLE. Anti-dsDNA antibodies were obtained from serum samples of donors with SLE collected through a volunteer donor program. Blood samples were drawn, serum harvested, aliquots made, labeled, and stored frozen at −70° C until used. In this assay, 25 µl of patient's serum was added to 75 µl of Tris buffer (50 mM Tris, 150 mM NaCl pH 7.5, 10% normal rabbit serum), then 100 µl of $^{125}$I-labeled recombinant dsDNA was added, mixed and incubated at 37° C for one hour. Similar samples containing known amounts of anti-dsDNA antibodies (calibrators) were prepared and incubated at the same time. 500 µl of 70% saturated ammonium sulfate was added to each tube, mixed, and then centrifuged at 800×g for 15 minutes to precipitate the antibodies in solution. The supernatant was decanted and the amount of radioactivity in the precipitated product was determined by counting the radioactivity in a gamma counter. The amount of radioactivity in the precipitant is proportional to the amount of anti-dsDNA antibodies that bound to $^{125}$I-labeled recombinant dsDNA. Calibrators with known amounts of anti-dsDNA antibodies were used to generate a standard curve from which the amount of dsDNA binding by anti-dsDNA antibodies could be calculated.

Serum samples from 58 patients were assayed for the presence of antibodies to dsDNA using the Farr assay described above. Forty-two of these samples had sufficient levels of antibody ($\geq$20% binding) to use in the LJP 394 inhibition assay.

LJP 394 was tested for its ability to inhibit binding of anti-dsDNA antibodies to $^{125}$I-labeled recombinant dsDNA by a competitive Farr assay. Calf thymus DNA (ctDNA) was also used in the inhibition assay as another source of dsDNA. Calf thymus dsDNA was prepared by dissolving calf thymus DNA in nuclease-S1 buffer (0.2 M NaCl, 50 mM sodium acetate pH 4.5, 1 mM $ZnSO_4$ and 0.5% glycerol) and 100,000 units of S-1 nuclease and incubating for one hour at 37° C. The dsDNA was extracted from this mixture by adding an equal volume of phenol-chloroform, mixing, centrifuging, and harvesting the aqueous layer. The dsDNA was then precipitated by adding 2 volumes of EtOH, mixing, and centrifuging. The pellet was harvested, dried under vacuum and dissolved in water to approximately 10 mg/ml. The final concentration of the ct DNA preparation was determined spectrophotometrically assuming an extinction coefficient of 33 µg per 1 OD unit at 260 nM.

Each serum sample that gave $\geq$20% binding was tested in the inhibition assay. Briefly, 25 µl of patient's serum was added to 75 µl of Tris buffer (50 mM Tris, 150 mM NaCl pH 7.0, 10% normal rabbit serum) containing various concentrations of inhibitor (either calf thymus dsDNA or LJP 394), then 100 µl of $^{125}$I-labeled recombinant dsDNA was added, mixed and incubated at 37° C for one hour. 500 µl of 70% saturated ammonium sulfate was added to each tube, mixed and then centrifuged at 800×g for 15 minutes. The supernatant was decanted and the amount of radioactivity in the precipitated product was determined by counting the radioactivity in a gamma counter. Extent of inhibition was calculated by the following formula: {[(cpm patient's serum without inhibitor—cpm without patient's serum, no inhibitor)—(cpm patient's serum with inhibitor—cpm without patient's serum, no inhibitor)] divided by (cpm patient's serum without inhibitor—cpm without patient's serum, no inhibitor)} all times 100.

Figure 1B:
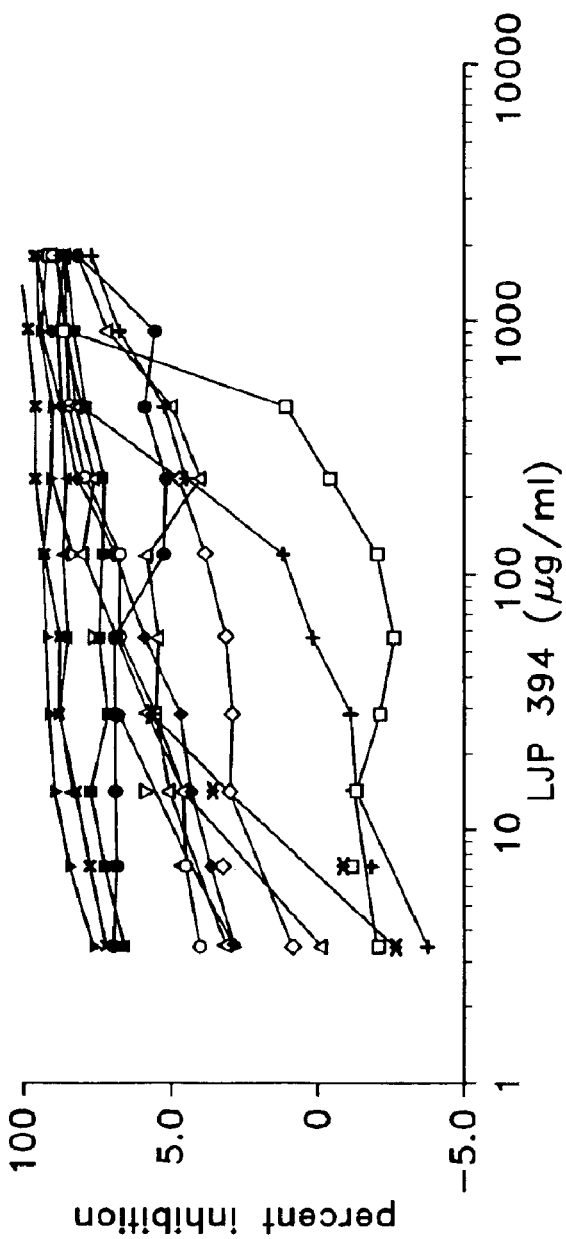
Figure 1C:
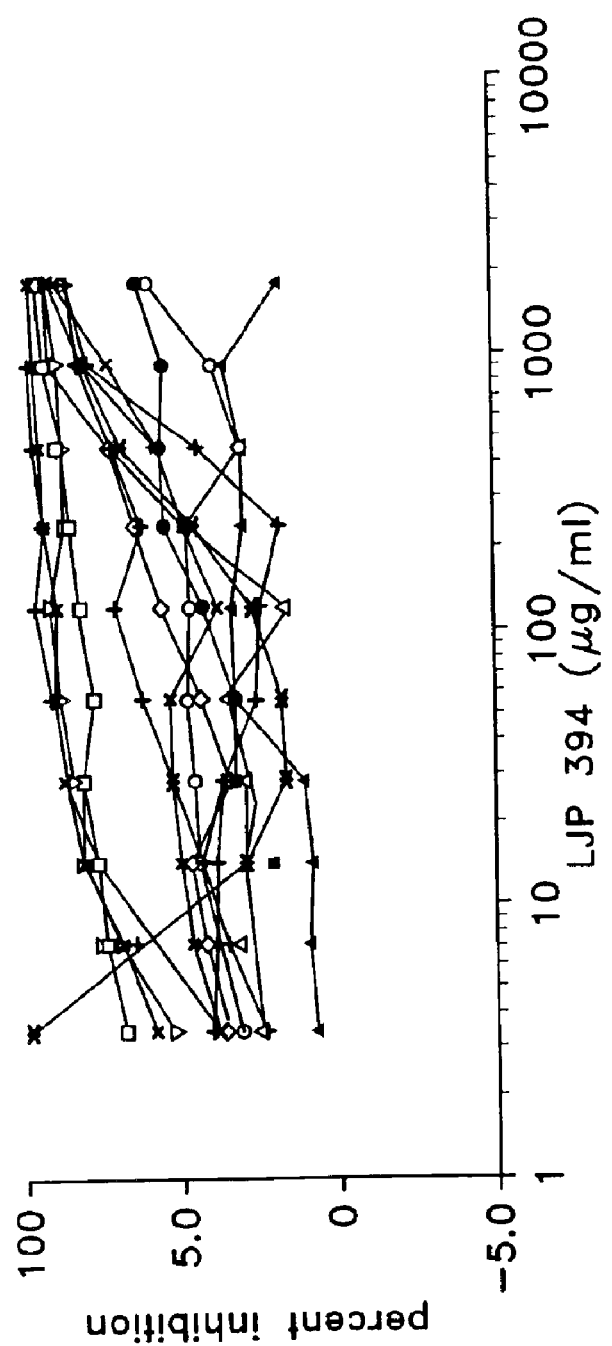

FIGS. 1 A–C illustrate the ability of LJP 394 to inhibit the binding of autoantibodies from a representative populations of patients with SLE. Overall, LJP 394 was capable of inhibiting binding of the autoantibodies to dsDNA in 42 out of 42 patients with SLE. The inhibition curves for LJP 394 and calf thymus dsDNA were parallel, suggesting that the antigenic determinants being recognized by the SLE sera were identical on both the calf thymus dsDNA and LJP 394.

The ability of LJP 394 to inhibit the binding of anti-DNA antibodies in a mouse models of SLE was also tested. Competitive inhibition assays with calf thymus dsDNA and LJP 394 were performed as described above and the results are shown in Table 1. The 50% inhibition ratios ($IC_{50}$ LJP 394/$IC_{50}$ ctDNA) were lowest for human anti-dsDNA antibodies (from SLE sera), compared to the mouse antibodies. LJP 394 showed high affinity for human antibodies and the NZBxNZW F1 mouse strain.

TABLE 1

Competitive Inhibition of Binding of Anti-ds DNA Antibodies by ctDNA and LJP 394

| No. of sera | Source of sera | $IC_{50}$, µg/ml (mean ± SD) | | $IC_{50}$ LJP 394/ctDNA ratio |
|---|---|---|---|---|
| | | ctDNA | LJP 394 | |
| 3 | MRL (lpr/lpr)(mouse) | 0.356 ± 0.455 | 200 ± 42 | 562 |
| 3 | NZBxNZWF$_1$ (mouse) | 0.021 ± 0.011 | 5.5 ± 0.7 | 258 |
| 5 | BXSB (mouse) | 0.028 ± 0.000 | 215 ± 144 | 7679 |
| 42 | Human SLE | 1.88 ± 0.920 | 46 ± 16 | 24 |

Example 2

Identifying SLE Patients by Affinity Assay

Figure 2:
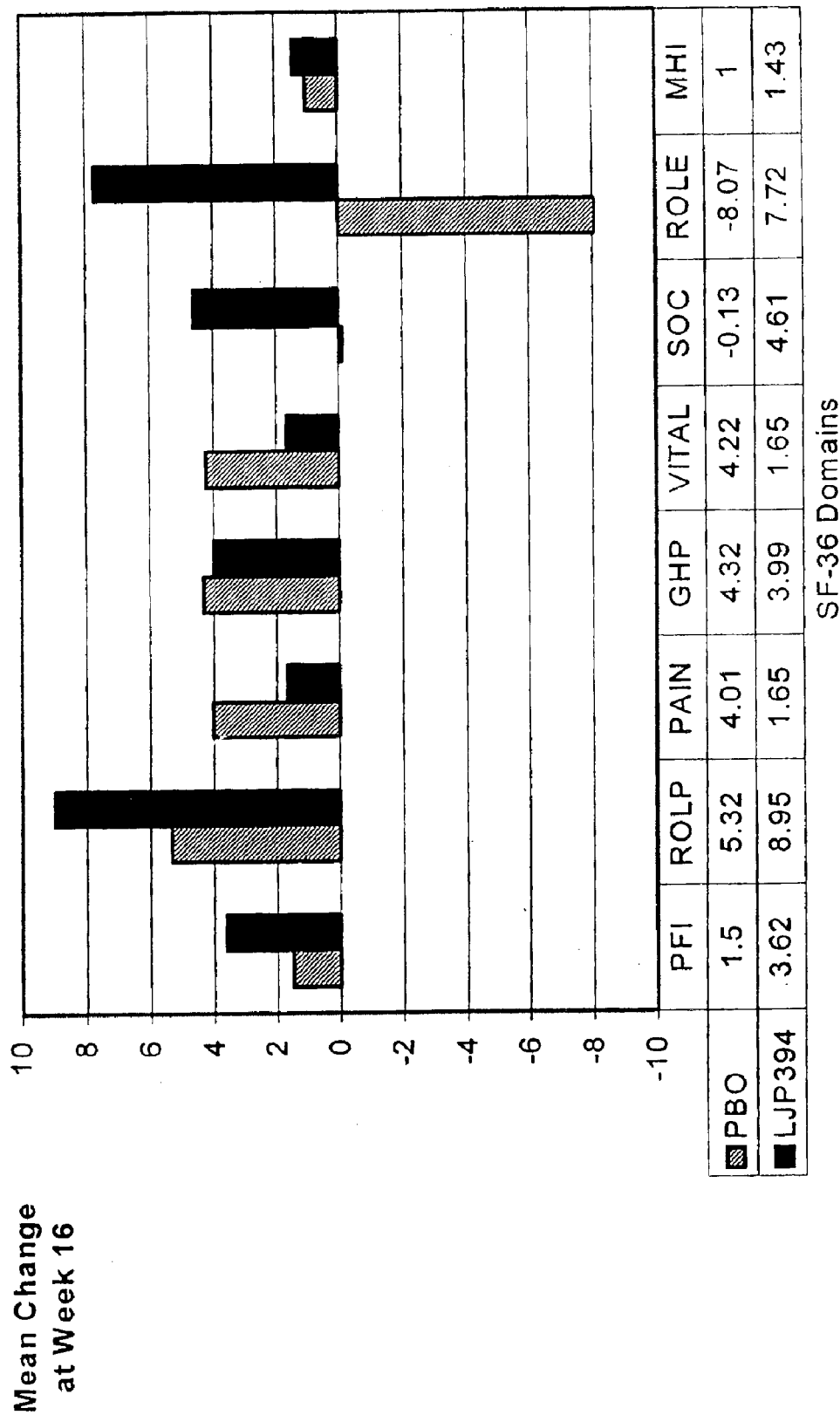
FIG. 2 is a graph depicting the binding of sera from SLE patients and normal patients by non-competitive affinity assay. IgG fraction from 10 SLE serum samples and 10 normal serum samples was evaluated for binding to the LJP 394 dsDNA epitope.

SLE patients were readily identified by measuring the binding affinity of sera from SLE patients to LJP 394 dsDNA epitope using the surface plasmon resonance assay described below. IgG fractions from 10 SLE patients serum samples and 10 normal patient serum samples were evaluated for binding to LJP 394 ds DNA epitope with a non-competitive direct affinity assay (BIACORE®; Piscataway, N.J.), as disclosed herein. FIG. 2 illustrates that the SLE samples all showed saturable binding to the epitope while normal samples showed low binding to the LJP 394 epitope and low specific binding.

Example 3

Determination of Titer-Weighted Average Affinity of Antibodies for Conjugate and Response to Treatment with Conjugate An assay using surface plasmon resonance was developed to directly measure a titer-weighted average affinity of antibodies from SLE patients for the conjugate LJP 394. Surface plasmon resonance is used to quantify the fractional saturation of antigen with antibody. This assay was adapted so that it measured the average affinity of the IgG population of LJP 394.

Materials and Methods

Reagents. Streptavidin CM5 chips, HBS buffer (0.01 M HEPES pH 7.4, 0.15 M NaCl, 3 mM EDTA and 0.005% (v/v) surfactant P20) were obtained from BIACORE AB (Piscataway, N.J.).

LJP 394 is composed of four 20-mer dsDNA epitopes that are covalently attached to a triethyleneglycol-based platform by a thiol linkage. The DNA epitope was composed of 5'-$(CA)_{10}$-3' strands annealed to complementary GT strands, with biotin attached at the free 5' ends of the GT strand. Biotin was incorporated by using Biodite biotin amidite (Pharmacia; Uppsala, Sweden) in the final coupling of the $(GT)_{10}$ strand. LJP 394 was prepared essentially as described in Jones et al. (1995) except that this biotin-modified $(GT)_{10}$ strand was used in the annealing step. In some experiments, only the dsDNA epitope was used for immobilization on the streptavidin chip. The epitope was prepared by annealing 5'-$(CA)_{10}$-3' to 5'-biotin-$(TG)_{10}$-3' and purifying the dsDNA by HPLC.

Plasma samples from SLE patients were collected at visit 2, prior to start of study drug administration and at visit 11, after 4 months of weekly drug administration.

Total IgG fraction was isolated from plasma by combining 100 μl of plasma with 100 μl of IgG binding buffer (Pierce Chemical Co.; Rockford, Ill.) and mixing with Immunopure Plus® protein G agarose beads (Pierce Chemical Co.) according to manufacturer recommendations. Elution of IgG from the beads was accomplished by following the acid elution/neutralization protocol of Pierce Chemical Co., and 300 μl of acid eluted IgG was neutralized with 100 μl of 1 M $NaPO_4$, pH 7.5. These purified IgG samples were then used in the titration experiments. Total IgG concentrations were determined with the Bradford assay (Biorad; Hercules, Calif.).

Surface Plasmon Resonance. All experiments were performed using a BIACORE® 2000 instrument at 25° C with a flow rate of 10 μl/minute. LJP 394 was attached to the streptavidin CM5 chip through its 5' biotin group by flowing a 50 μg/ml solution of LJP 394 in HBS+0.3 M NaCl over the chip for 20 minutes at 5 μl/minute. The chip was preconditioned prior to titration with 3×1 minute pulses of regeneration buffer (1M NaCl and 50 M NaOH). When the dsDNA epitope of LJP 394 was used for immobilization, the biotinylated epitope was flowed over the chip at a concentration of 10 μg/ml using similar conditions as employed for the biotinylated LJP 394 epitope.

Antibody titrations of the dsDNA (LJP 394) chip were performed with serial 1:2 dilutions of purified IgG in HBS. Sample was injected for 5 minutes, which is adequate association time for a significant approach to the response plateau, and was followed by a 4 minute dissociation period where HBS is flowed over the chip, then a 30 second regeneration was performed with 1 M NaCl, 50 mM NaOH.

Analysis. Response plateau values ($R_{eq}$) were obtained by a nonlinear least squares fit of the association curves to equation 1, after subtraction of a background curve for an empty flow cell, to account for bulk response/buffer effect, and using the manufacturers software (BiaEvaluation version 2.2, Uppsala, Sweden)

$$R_t = R_{eq}(1 - e^{-k_s(t-t_0)}) + R_0 \quad \text{(equation 1)}$$

where $R_t$ is the measured response at time t, $R_{eq}$ is the equilibrium plateau response, t is time, $t_0$ is initial time, $k_s$ is an apparent association constant ($k_s = k_a C + k_{dis}$, where $k_a$ is the association constant, C is the analyte concentration and $k_{dis}$ is the dissociation constant), and $R_0$ is a response offset. These response plateaus were plotted versus the concentration of total IgG, and fitted to equation 2 to obtain values for $R_{max}$ and $K_d^*$.

$$R_{eq} = \frac{R_{max} A_T}{K_d^* + A_T} \quad \text{(equation 2)}$$

where $A_T$ is the total antibody (IgG) concentration, $R_{max}$ is the maximum response plateau and $K_d^*$ is an apparent dissociation constant. $K_d^*$ is the same as $<K_d'>$ in equation 3 (below), the titer-weighted-average (TWA) dissociation constant. The derivation of $K_d'$ was performed as described in Sem et al. (1999) and provides insight into the physical meaning of the $K_d^*$ constant in equation 2. This analysis pertains to the case of a polyclonal pool of n different antibody subpopulations, where B=LJP 394 and $A_i$=antibody subpopulation i.

$$<K_d'> = \frac{A_T}{\sum_{i=1}^{n}(A_i/K_i)} = \frac{1}{\sum_{i=1}^{n}(r_i/K_i)} \quad \text{(equation 3)}$$

where $r_i$ (relative titer) is the fraction of total antibody present as form i, defined as $r_i = A_i/A_T$. Thus, equation 3 is the general equation describing the observed dissociation constant for a polyclonal population of n different antibody subpopulations of relative titer (fractional presence) $r_i$ and dissociation constant $K_i$. This $<K_d'>$ is the apparent $K_d$ of eq 2, $K_d^*$.

The measured apparent dissociation constant $K_d'$ reflects both inherent affinity of antibody subpopulation i for antigen, and relative titer of antibody subpopulation i ($r_i$). In general, $0 < r_i < 1$, so $K_d' > K_i$. That is, the factors that can cause $K_d'$ to decrease are an increase in affinity ($K_i$ decreases) and/or an increase in relative titer of antibody subpopulation i ($r_i$ increases). In practice, in a polyclonal population of antibodies, there will be many different antibody subpopulations that bind, each with slightly different affinity.

The above analysis, and that further described in Sem et al. (1999), produces an apparent dissociation constant that is a reflection of the various affinities and titers of clonally related subpopulations of antibodies within a polyclonal pool. The apparent dissociation constant obtained as described is the titer-weighted-average (TWA) dissociation constant derived in equation 3, $<K_d'>$. The value of $<K_d'>$ is dominated by antibody subpopulations that have the largest $r_i$ (highest relative titer) and smallest $K_i$ (highest affinity) in combination. Any change in relative titers of subpopulations with a given affinity will change the apparent dissociation constant according to equation 3.

Results

Study 1

Equilibrium binding values from 4 dilutions of plasma IgG from SLE patients were evaluated with the surface plasmon resonance-based affinity assay to determine the concentration of IgG required to reach half-maximal binding. This value, the apparent equilibrium dissociation constant ($K_d'$ in mg/ml of IgG) reflects the titer-weighted average affinity of the IgG population for LJP 394, as outlined above and by Sem et al. (1999).

Table 2 contains a comparison of the Kd' from the initial IgG affinity for LJP 394 in naive patients (visit 2) and the affinity after 4 months of weekly study drug administration (visit 11). Data from this first patient population indicated that patients who entered the trial with high affinity antibodies for LJP 394 (low numeric $K_d'$=high affinity) were more likely to respond to drug treatment (higher numeric $K_d'$=decrease in TWA).

TABLE 2

Comparison of $K_D'$ values

| Patient ID | $K_d'$ @ visit 2 (mg/ml) | $K_d'$ @ visit 11 (mg/ml) | % change in $K_d'$ |
|---|---|---|---|
| 02-19 | 0.05 | 0.32 | 540 |
| 08-76 | 0.15 | 0.34 | 127 |
| 04-37 | 0.41 | 0.77 | 87 |
| 02-13 | 0.51 | 0.88 | 73 |

The data in Table 2 suggested that the initial IgG affinity ($K_d'$) may predict the response of the patients to LJP 394. When IgG affinities of the same samples were measured using the (non-competitive) Farr assay as described in Example 1, the initial Farr values were not predictive of patient response, as shown in Table 3.

TABLE 3

Comparison of Farr values

| Patient ID | Farr @ visit 2 (IU/ml) | Farr @ visit 11 (IU/ml) | % change in Farr |
|---|---|---|---|
| 02-19 | 35 | 14 | −60 |
| 08-76 | 60 | 27 | −55 |
| 04-37 | 23 | 18 | −22 |
| 02-13 | 75 | 72 | −4 |

Figure 3A:
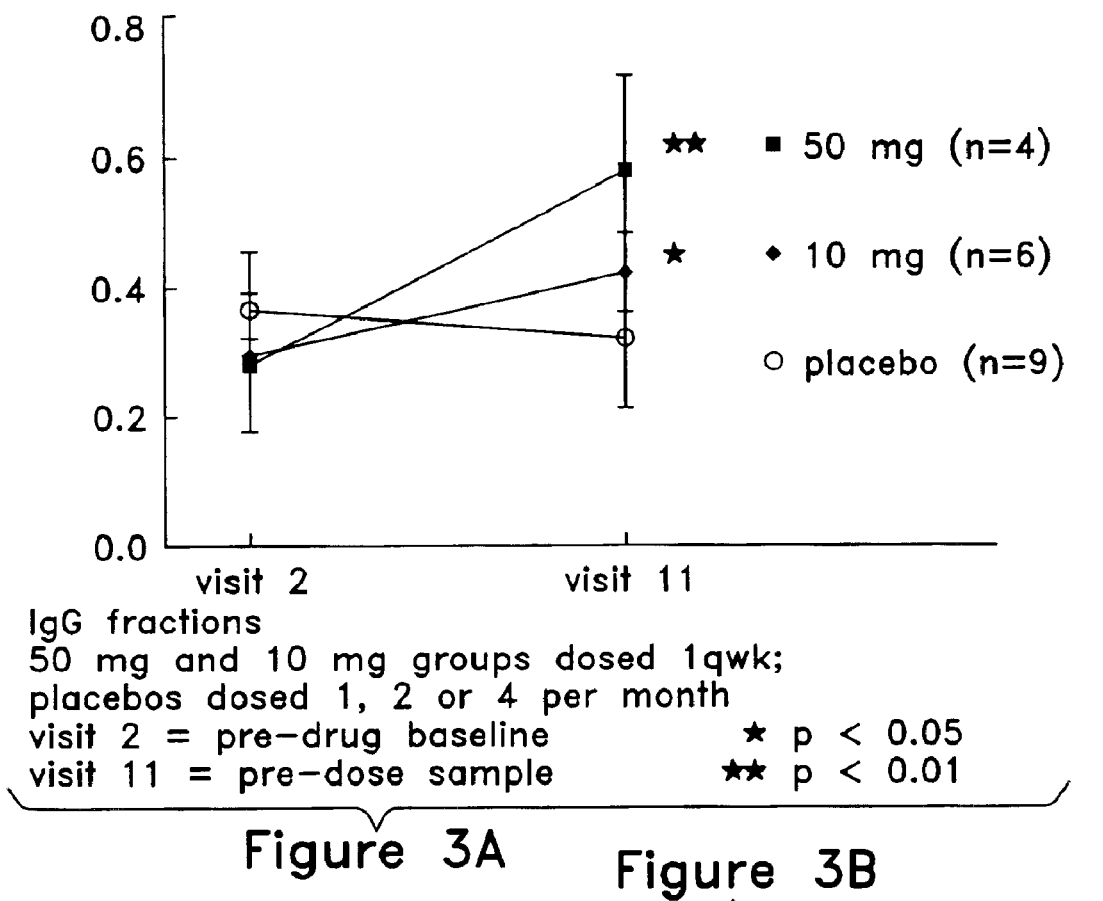
FIG. 3A is a graph depicting an apparent dose-dependent decrease in antibody affinity (as indicated by an increase in $K_D'$) in patients receiving 10 mg (solid circle) versus 50 mg (solid square) of conjugate LJP 394. Placebo is depicted as open circle. Visit 2 is pre-drug baseline; visit 11 occurred after 4 months of weekly drug administration. $K_D'$ values (Y-axis) are in mg/ml of IgG.
Figure 3B:
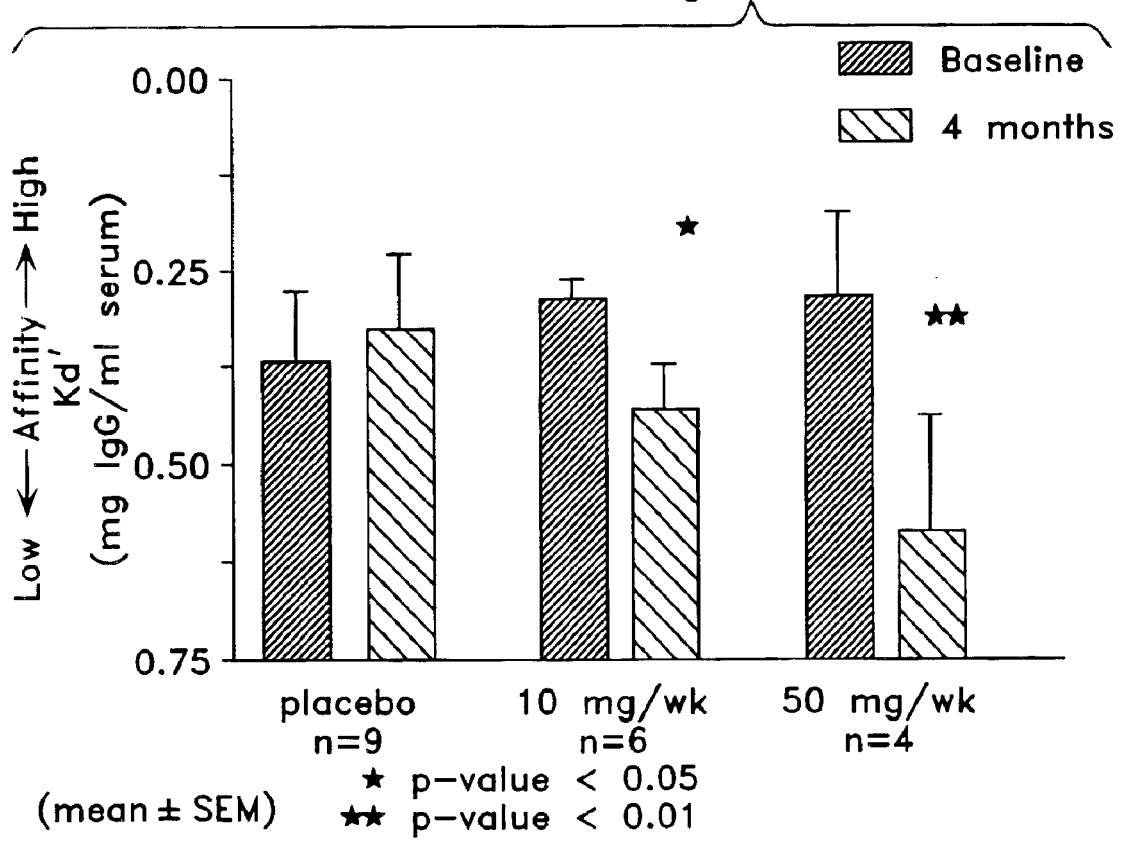
FIG. 3B is the same data depicted in the form of a bar graph.

FIG. 3A depicts the dose dependent decrease in anti-dsDNA antibody burden ($K_d'$) in SLE patients from treatment with LJP 394. FIG. 3B depicts the same data in the form of a bar graph. These results demonstrate the dose dependent effect of LJP 394 at 50 mg/wk provided a better response than 10 mg/wk and both groups were different than placebo.

Study 2

For the second SLE patient population studied, the first plasma sample was obtained at visit 2 or 3, prior to start of study drug administration, and the second sample was collected immediately following 4 months of study drug administration at 100 mg/wk (visit 18 or 19). These 2 samples were then used to determine the initial affinity in naive patients and the affinity after 4 months of study drug administration. There was no known bias to the selection of samples except that they included all the patients available for those sample times. The results are shown in Table 4 (number of available samples indicates number of samples available for analysis; total number of flares represents only those flares attributable to lupus). Table 5 includes all the samples in Table 4 in addition to more patient samples.

TABLE 4

Samples for Study 2

|  | # available samples/ total # patients | # of flares represented/ total # of flares |
|---|---|---|
| LJP 394 | 71/114 | 16/19 |
| Placebo | 70/115 | 16/23 |

TABLE 5

Samples for Study 2

|  | # available samples/ total # patients | # of flares represented/ total # of flares |
|---|---|---|
| LJP 394 | 104/114 | 18/19 |
| Placebo | 106/115 | 23/23 |

Figure 4A:
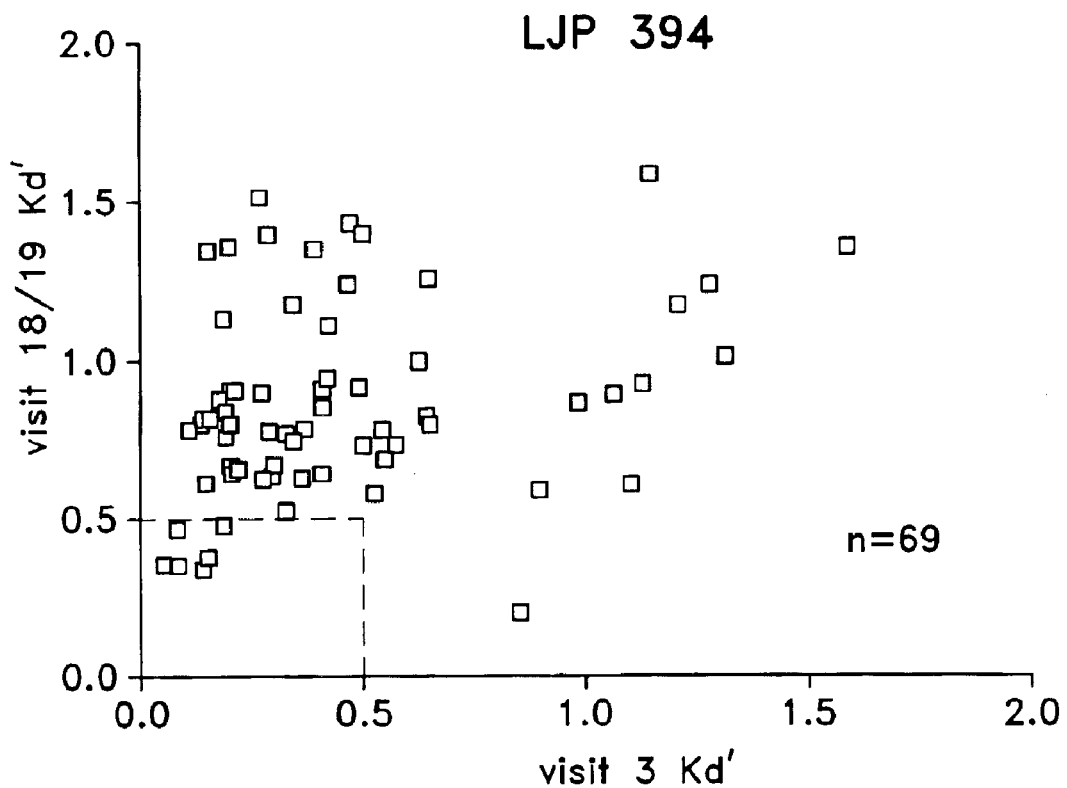
FIGS. 4A and 4B are graphs depicting the $K_D'$ before LJP 394 treatment or placebo (X-axis) versus the $K_D'$ after four months of LJP 394 treatment or placebo (Y-axis). Graph A represents patients receiving treatment with LJP 394 conjugate and graph B represents patients receiving placebo (i.e., not receiving treatment).
Figure 4B:
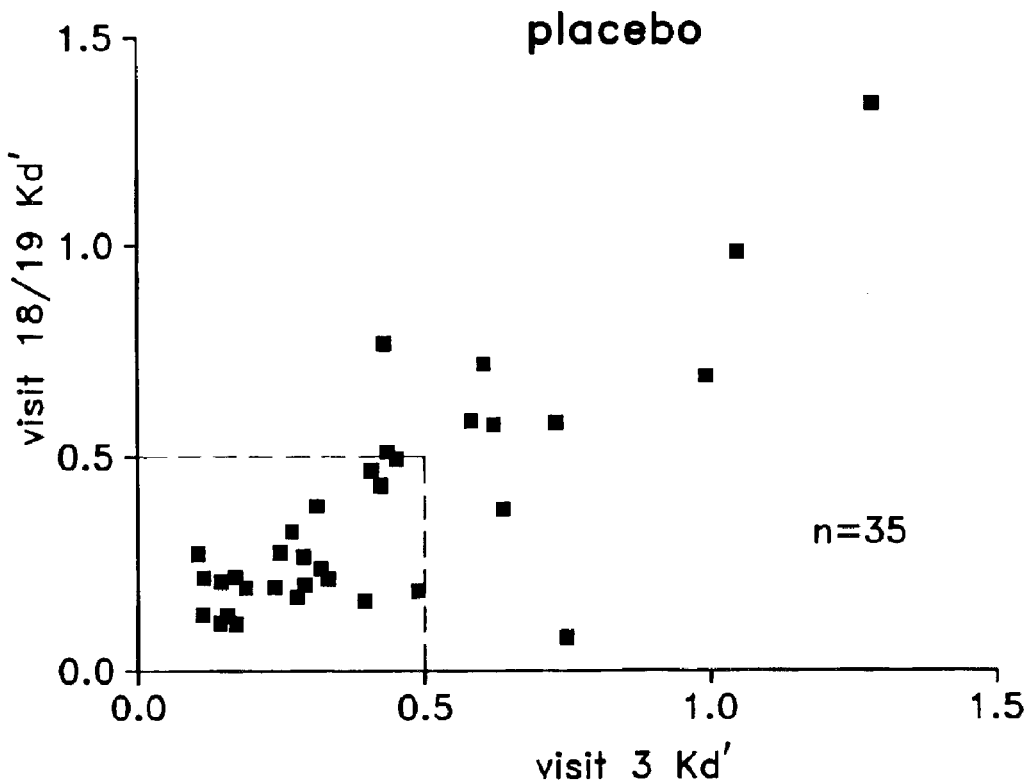
Figure 4C:
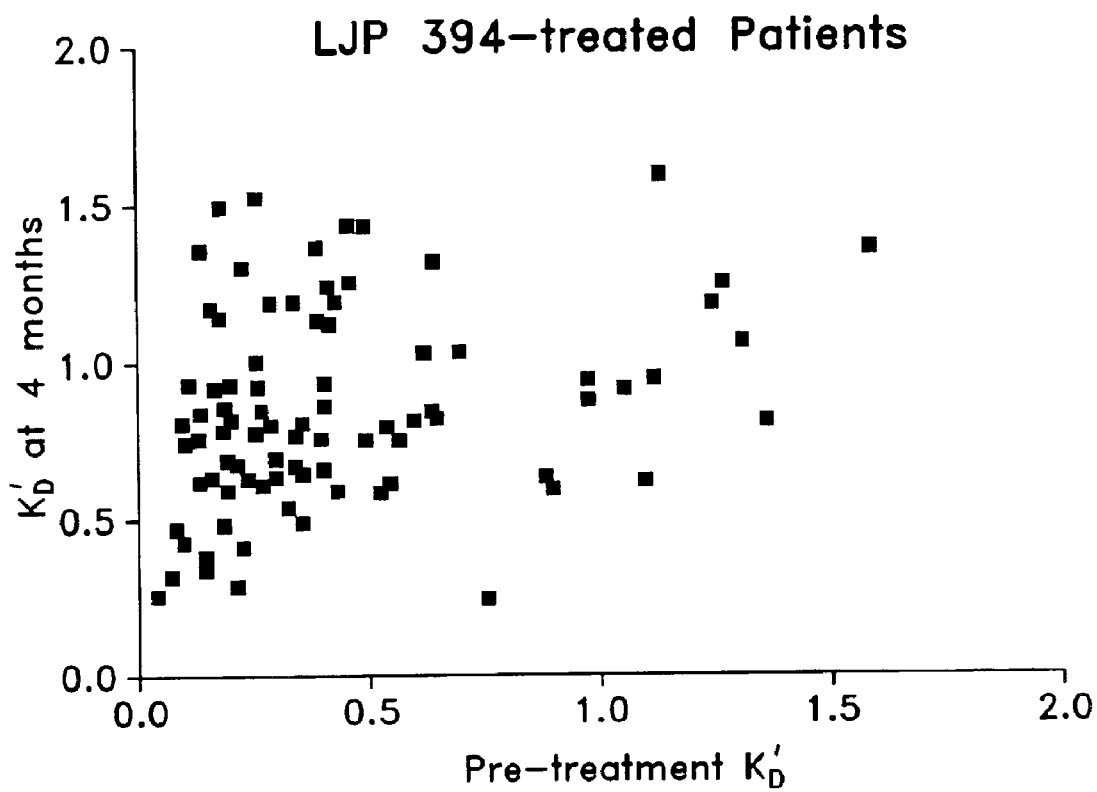
FIGS. 4C and 4D are graphs depicting the same data presented in FIGS. 4A and 4B with the addition of data from additional patients.
Figure 4D:
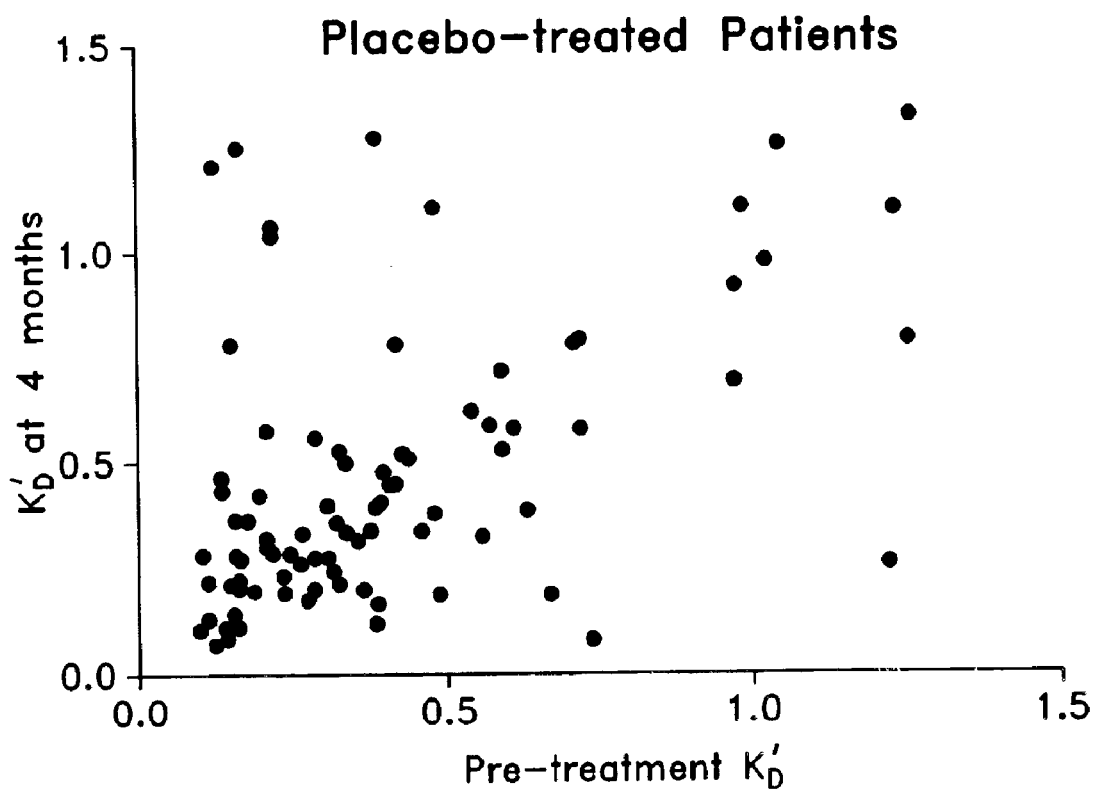
Figure 5A:
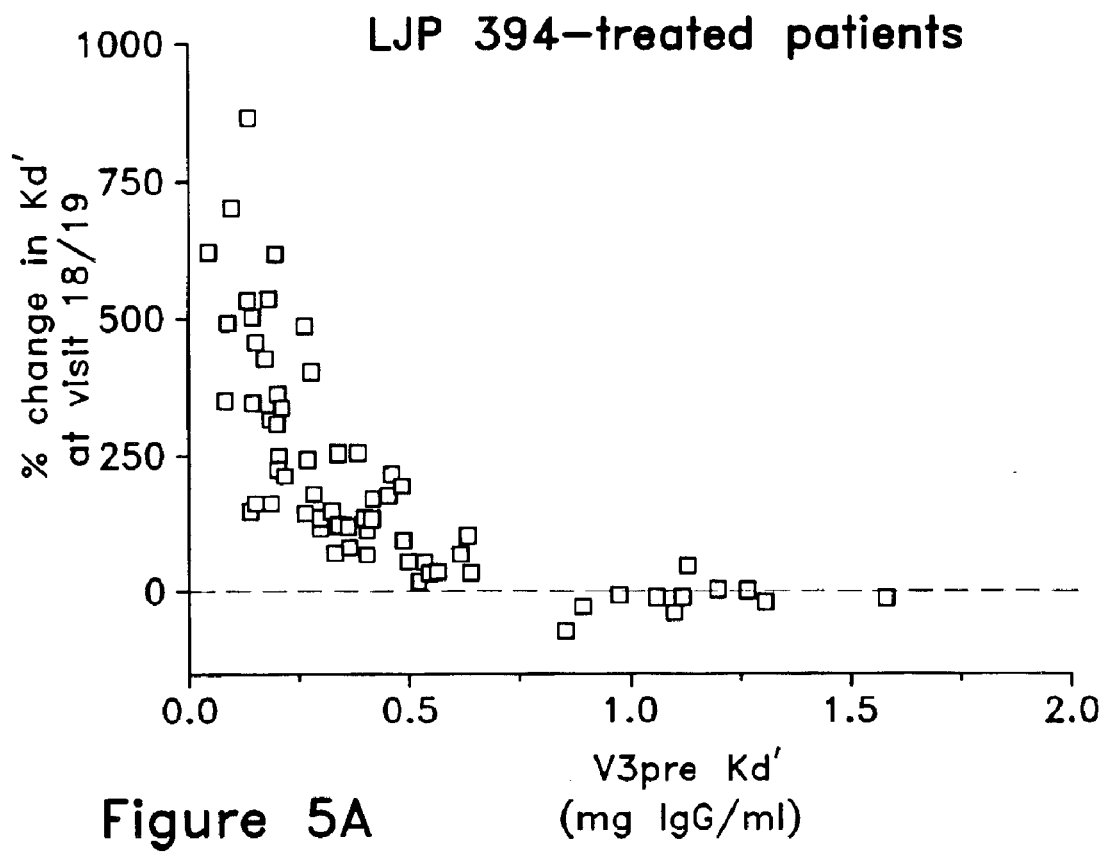
FIGS. 5A and 5B are graphs depicting change in $K_D'$ in patients receiving conjugate LJP 394 (A, open squares) and in patients receiving placebo (B, solid squares). Each square represents a patient. X-axis is the $K_D'$ before receiving treatment (or placebo); Y-axis is the percentage change in $K_D'$ after 4 months of treatment (or placebo).
Figure 5B:
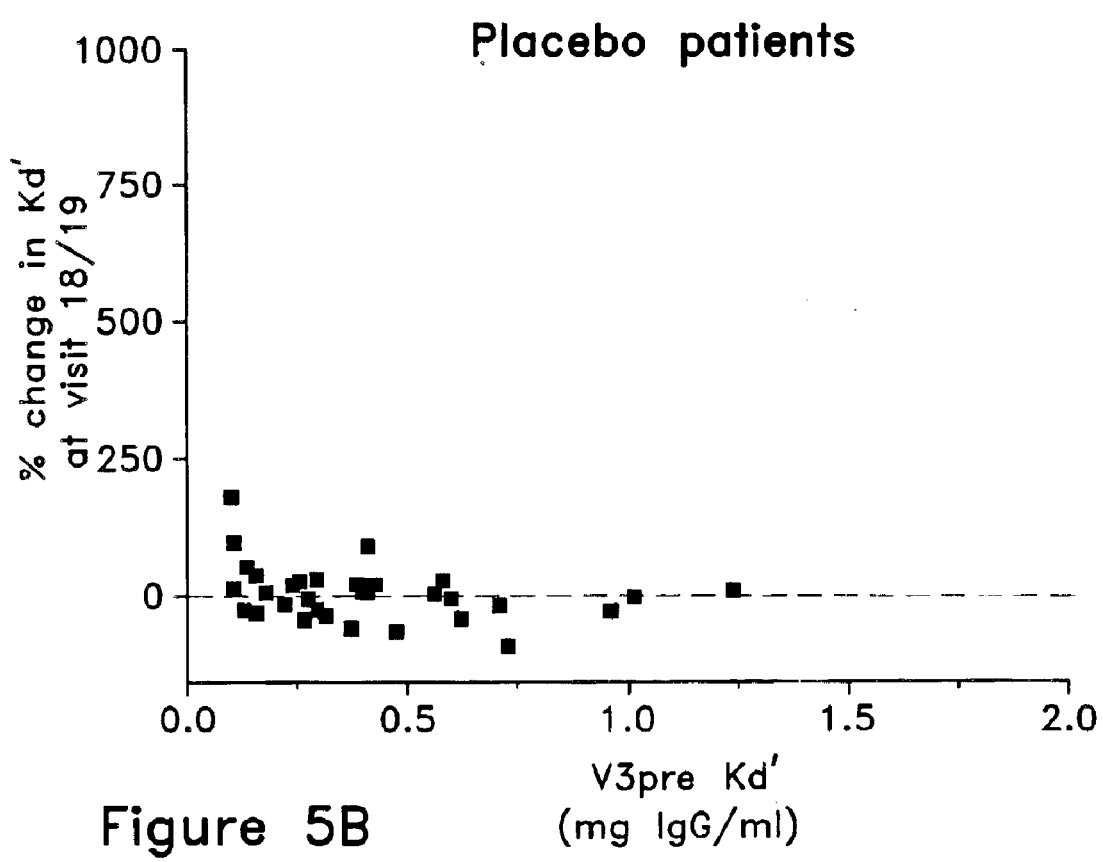
Figure 6A:
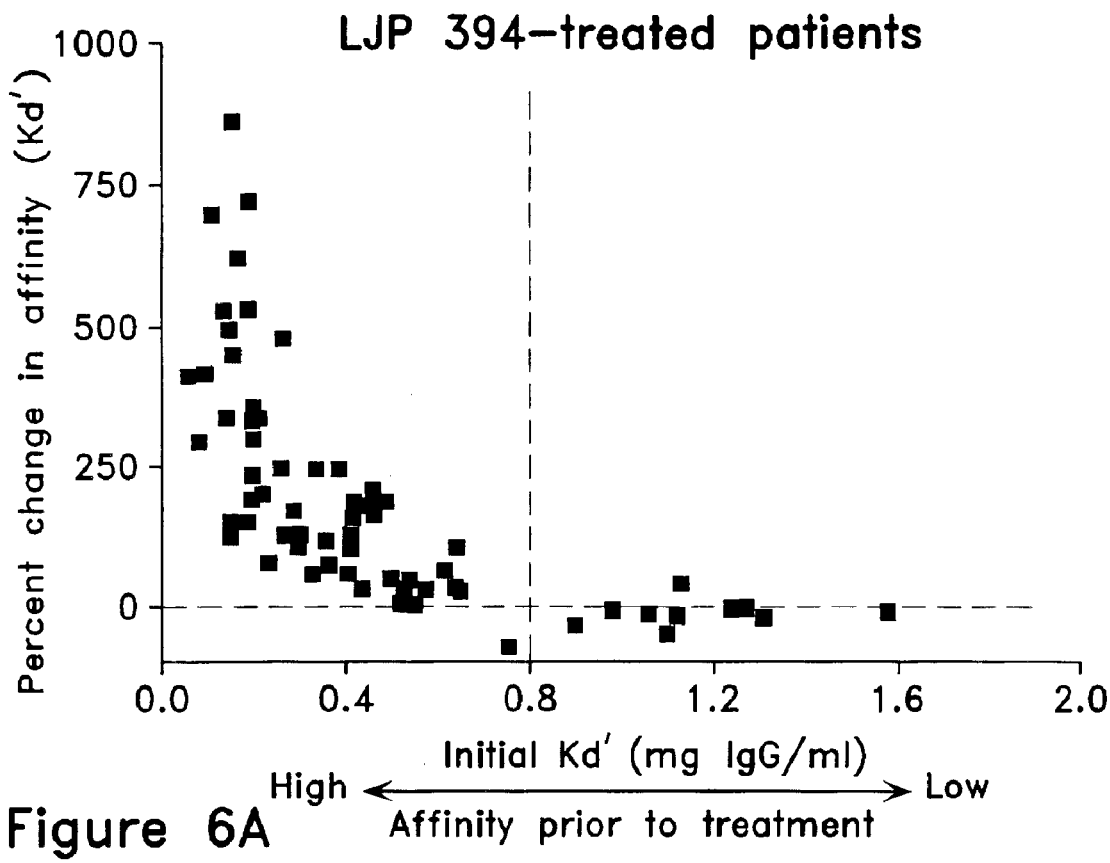
FIGS. 6A and 6B are graphs which depict data the same data as that shown in FIGS. 5A and 5B with the addition of data from additional patients. The two panels depict the change in Kd' in patients receiving conjugates LJP 394 (left panel) or placebo (right panel). Each square represents an individual patient. X-axis is the Kd' before receiving treatment (or placebo); Y-axis is the percentage change in $K_D'$ after 4 months of treatment with 100 mg LJP 394 (or placebo) i.v. weekly.
Figure 6B:
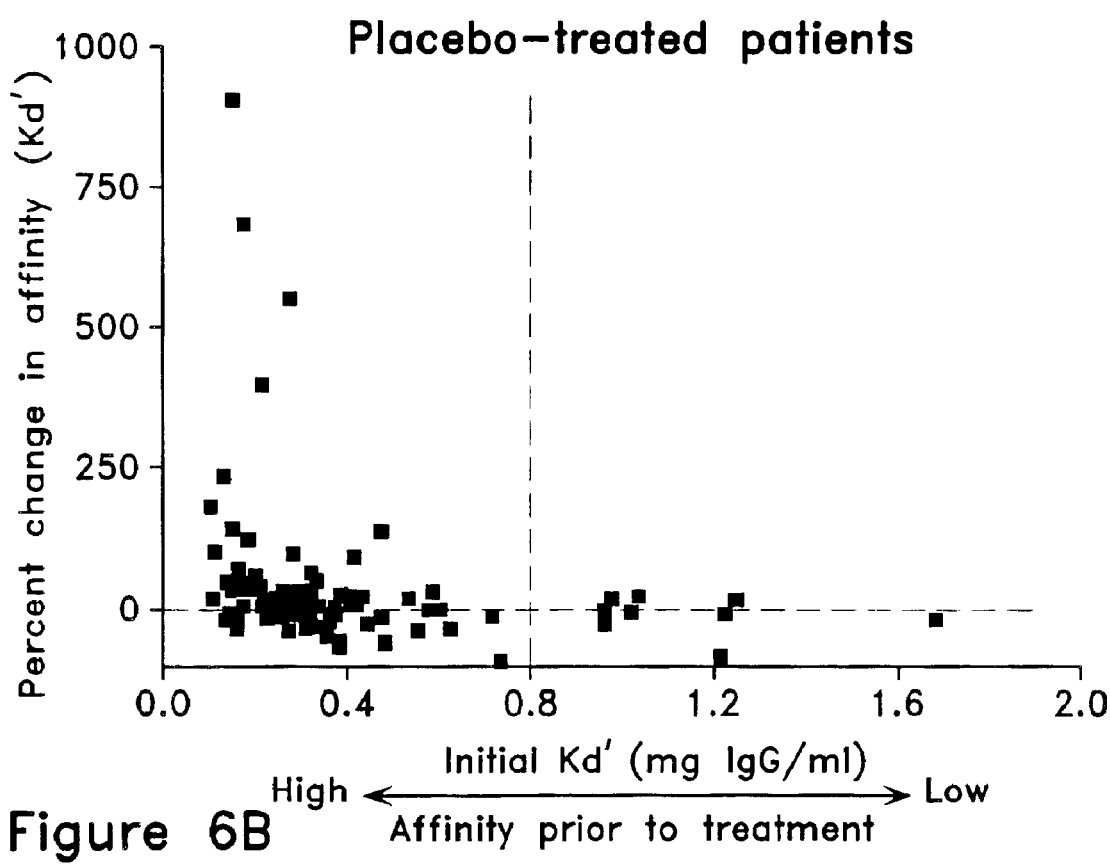

Change in antibody affinity. Results for the drug treatment group and from the placebo group are shown in FIGS. 4 and 5. Each square represents data from a single patient. FIGS. 4A and 4B reflect the patient pool summarized in Table 4. FIGS. 4C and 4D reflect the patient pool summarized in Table 5. FIGS. 5A and 5B display the data shown in FIGS. 4A and 4B in terms of percent change in Kd'. V3pre $K_d'$ represents the $K_d'$ for patients just prior to the start of study drug administration. In FIGS. 4A–D, the Y axis represents the $K_D'$ values after 4 months of drug treatment or placebo. In FIGS. 5A and 5B, the Y axis represents percent change in affinity ($K_D'$ values) over 4 months of drug treatment or placebo. FIGS. 6A and 6B reflect similar data analysis as shown in FIG. 5 but with an expanded patient population, as summarized in Table 5.

Figure 7:
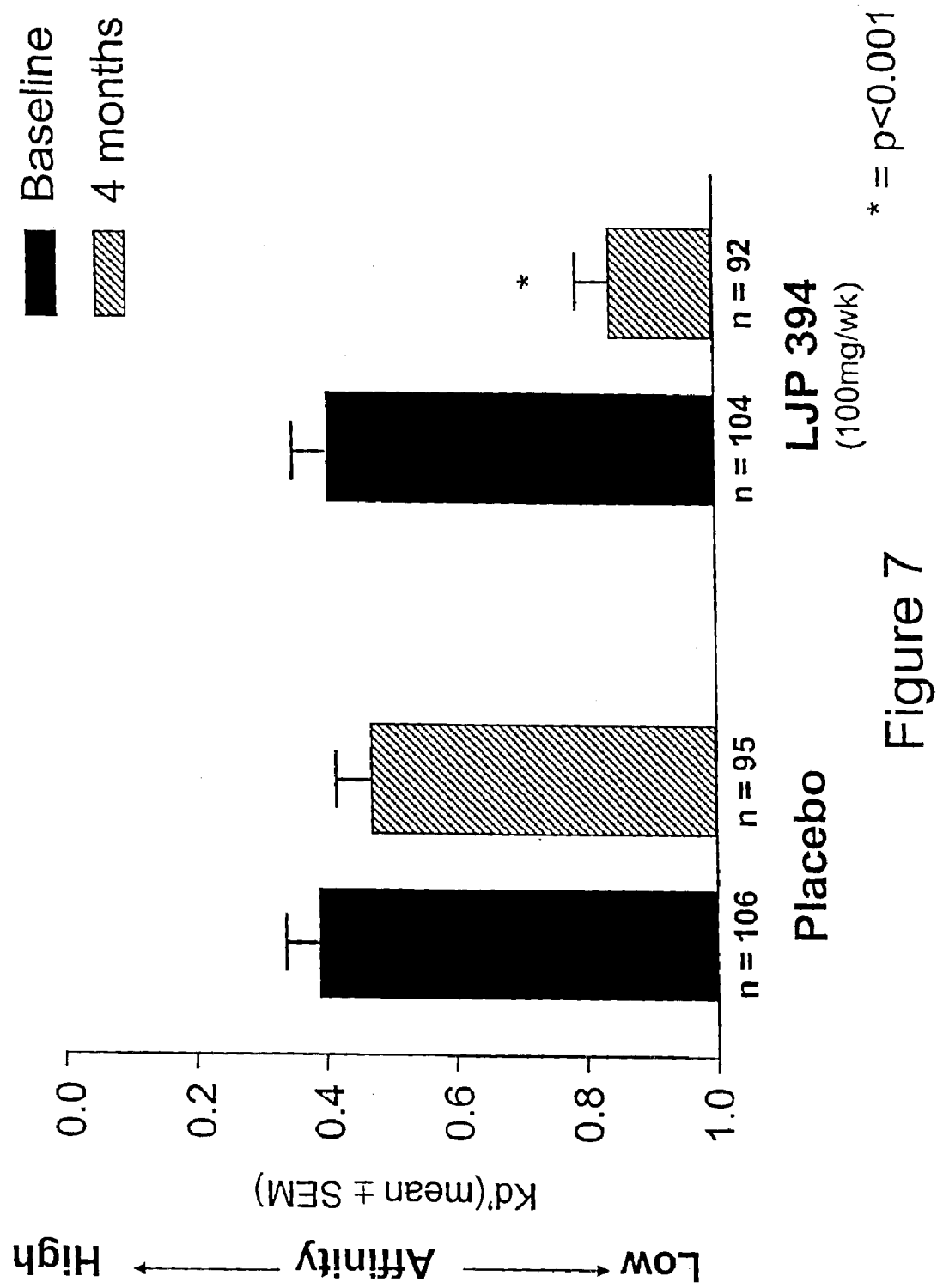
FIG. 7 is a graph depicting a summary of the effects of drug treatment on the affinity of patient sera for LJP 394 in the second study. The data are mean ± SEM for all patients in each group. The graph compares the Kd' before (solid bars) and after (slashed bars) 4 months of treatment with either 100 mg LJP 394 i.v. or placebo weekly.
Figure 8:
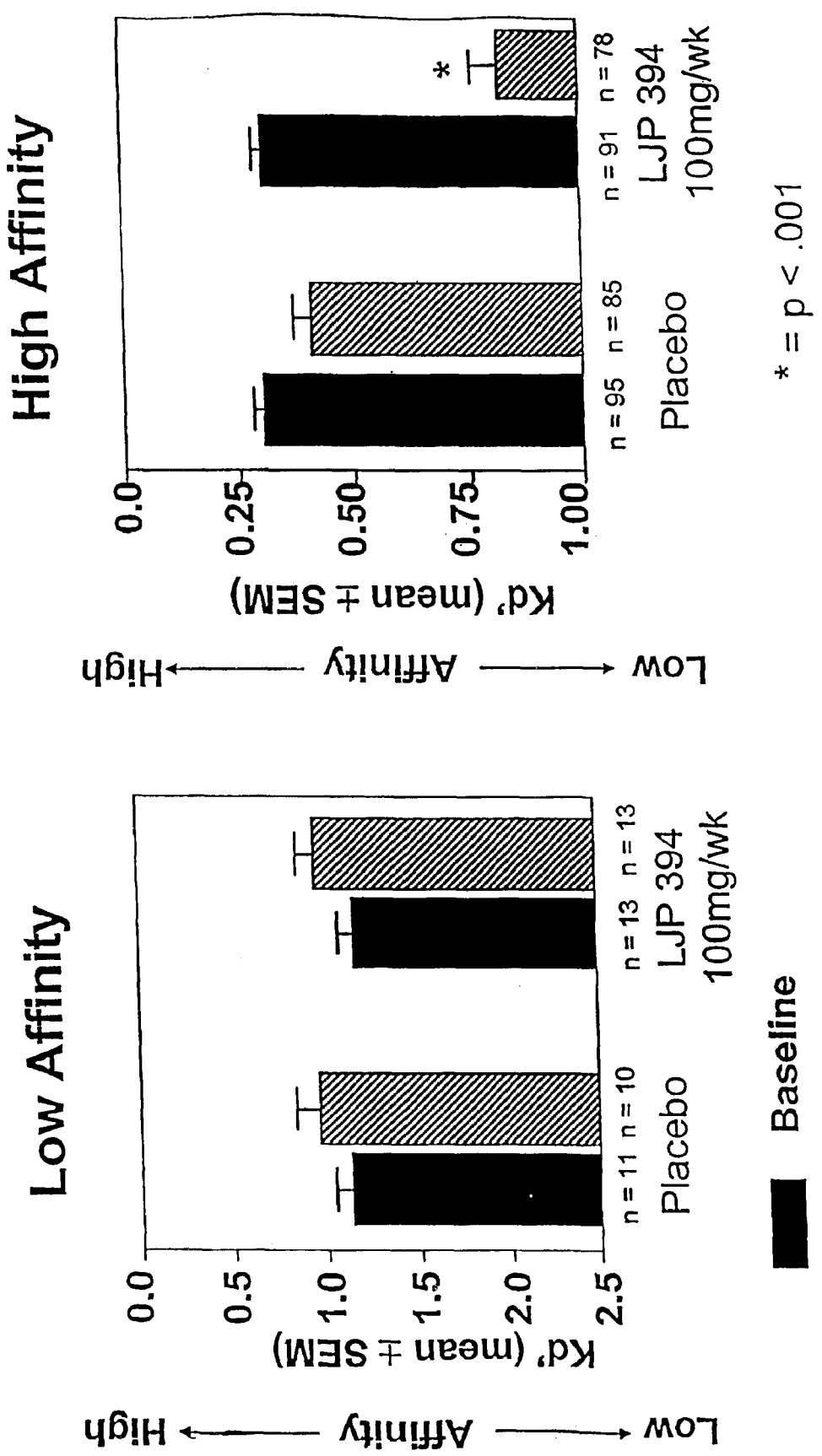
FIG. 8 is a graph which depicts the patient population from FIG. 7 divided into two groups, low affinity group (greater than Kd' of 0.8 IgG/ml serum) and high affinity group (less than Kd' of 0.8 IgG/mL serum). Data are mean ± SEM for all patients in each group. The graph compares the Kd' before (solid bars) and after (slashed bars) 4 months of treatment with either 100 mg LJP 394 i.v. or placebo weekly.

The data for the expanded patient population are summarized in FIG. 7 (100 mg/week LJP 394). When results from FIG. 7 are broken down into high affinity (Kd'<0.8 mg/ml) and low affinity groups (Kd'>0.8 mg/ml) as shown in FIG. 8, the high affinity group shows change in affinity over a 4 month period whereas the low affinity group does not show any significant change in affinity.

Figure 9:
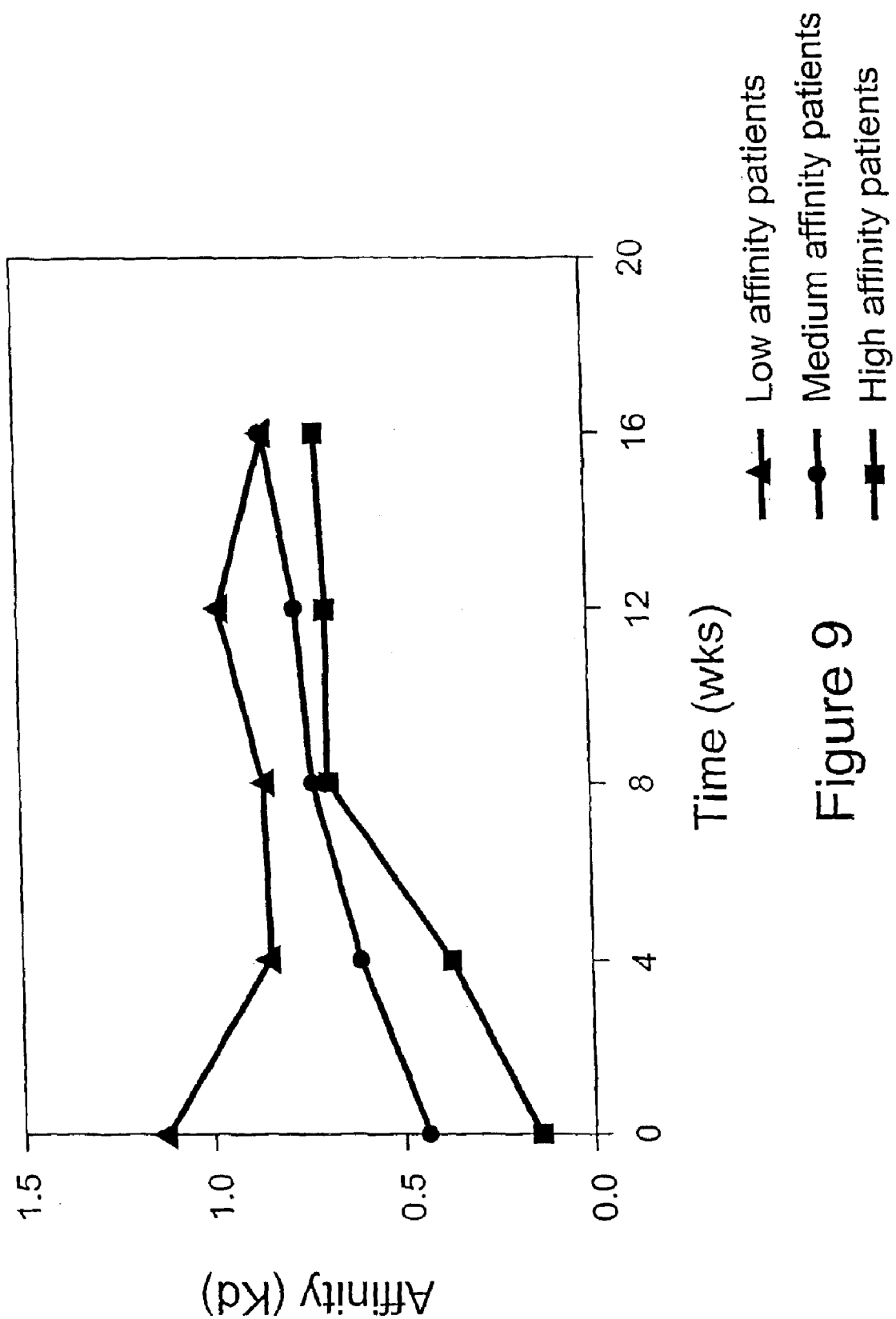
FIG. 9 is a graph which depicts the change in affinity of patient sera for LJP 394 epitope over time. The affinities are determined once a month for the induction period of the trial (first 4 months of dosing at 100 mg/wk). The x-axis is time elapsed in weeks; y-axis is Kd'. The samples were selected based on the initial (pre-treatment affinity) and segregated into three groups of relative affinity: high, medium, and low affinities. The affinity values are the mean of 3 patients. The solid triangles represent "low affinity patients" (Kd' mean about 1.13 mg/ml); the solid circles represent "medium affinity" patients (Kd' mean about 0.44 mg/ml); and the solid squares represent "high affinity" patients (Kd' mean about 0.14 mg/ml).

The change in antibody affinity is also depicted in FIG. 9. The samples were selected based on the initial (pre-treatment affinity) and segregated into three groups of relative affinity: high, medium, and low affinities. The affinity values are the mean of 3 patients. The solid triangles represent "low affinity patients" (Kd' mean about 1.13 mg/ml); the solid circles represent "medium affinity" patients (Kd' mean about 0.44 mg/ml); and the solid squares represent "high affinity" patients (Kd' mean about 0.14 mg/ml).

These data demonstrate that patients with high initial affinity for the LJP 394 epitope (low numeric $K_d'$=high affinity) exhibited greater response to the drug over 4 months when compared patients with lower initial affinity antibodies. They also suggest that one could preselect patients most likely to have a positive serological response to LJP 394.

Figure 10:
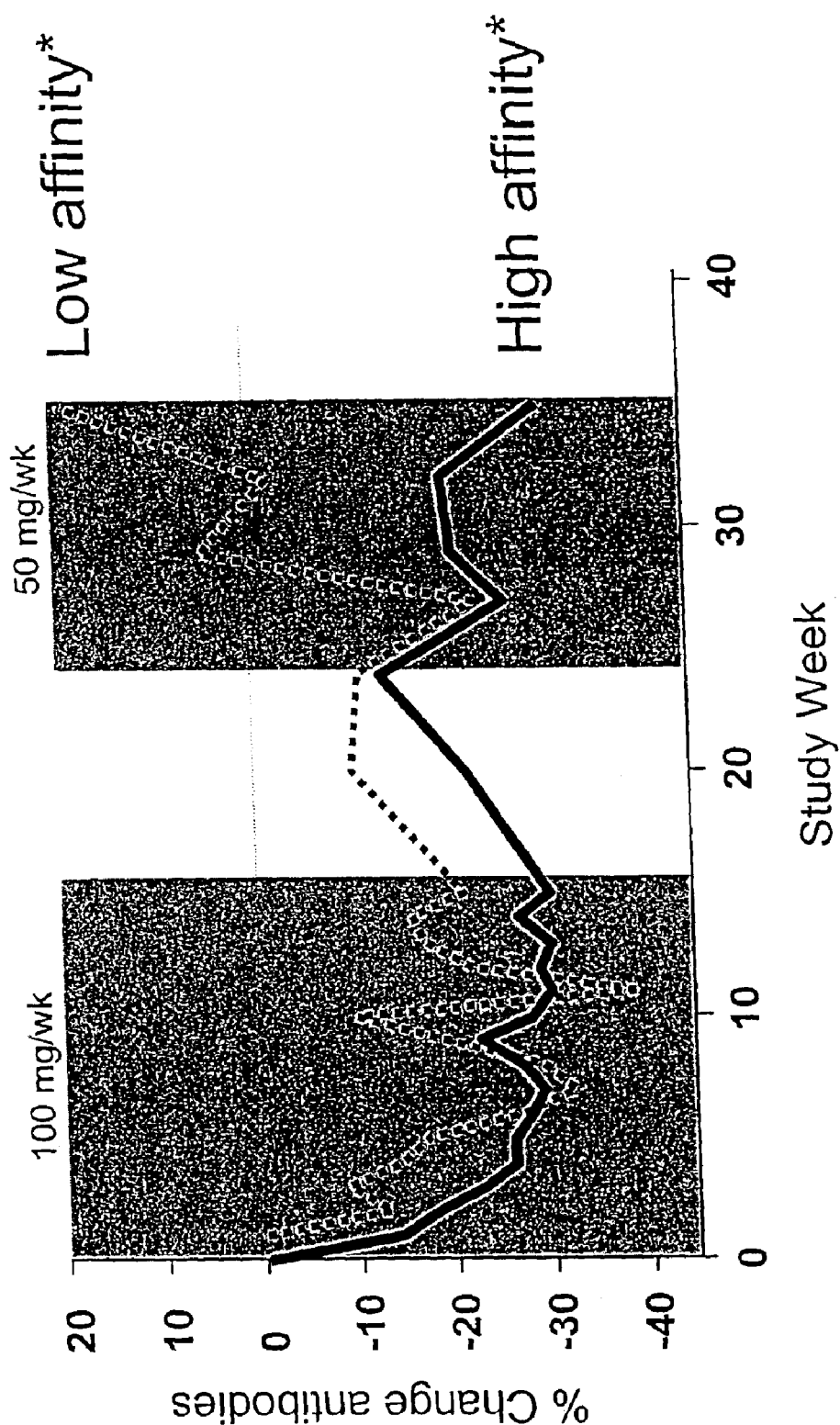
FIG. 10 is a graph which depicts the percent change in anti-ds DNA antibodies over time for high and low affinity patient groups treated with LJP 394, as assessed by a Farr assay. Data collected after high dose corticosteroid and/or cyclophosphamide treatment was excluded. The patients were stratified into low affinity (Kd'>0.8 mg/ml) and high affinity (Kd'≦0.8 mg/ml) subgroups. The low affinity patients are indicated by the dotted line while the high affinity patients are indicated by the solid line. The data are means of all patients studied. The x-axis is time from start of trial in weeks and the y-axis is the percent change in anti-dsDNA antibody levels from the start of the trial. The gray regions mark the dosing periods, the first period is the induction period with 100 mg/wk LJP 394 (or placebo) and the second dosing period is with 50 mg/wk LJP 394 (or placebo). There is an "off period", indicated by the white area of the graph, where no LJP 394 (or placebo) is administered.

The change over time in anti-ds DNA antibody levels, as assessed by non-competitive Farr assay in the LJP 394-treated patients was analyzed by stratifying the patients into 2 groups, low affinity ($K_D'$>0.8 mg/ml) and high affinity ($K_D'\leq 8$ mg/ml). FIG. 10 depicts a comparison of the two groups. Data collected after high dose corticosteroid and/or cyclophosphamide treatment was excluded. The low affinity group is depicted with a dotted line while the high affinity group is depicted with a solid line. The areas with gray, shaded background show the dosing periods. The first dosing period, indicated by the first block of gray background, is the induction period during which patients were given 100 mg/week of LJP 394 or placebo. The white, non-shaded area is the non-dosing period when no LJP 394 or placebo was administered. The second dosing period, indicated by the second block of gray background, was a period during which patients were given 50 mg/week of LJP 394 or placebo. As shown in FIG. 10, anti-dsDNA antibody levels are reduced in the high affinity group by the administration of 100 mg/wk and 50 mg/week of LJP 394. The anti-dsDNA antibody levels of the low affinity group was reduced somewhat with the administration of 100 mg/week of LJP 394 and not reduced with the administration of 50 mg/week LJP 394. As shown in FIG. 10, there is a significant reduction of anti-ds DNA antibodies in the high affinity group.

Figure 11A:
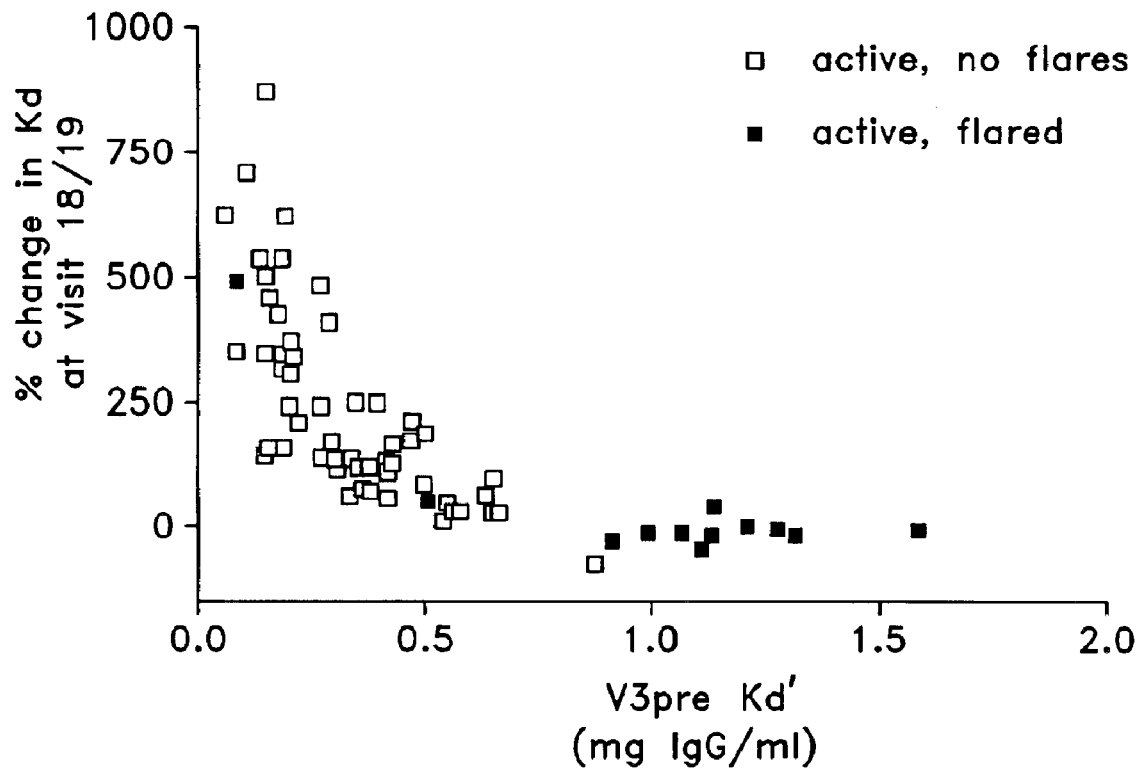
FIG. 11A is the same graph as FIG. 5A, except that incidence of active renal flares in a patient are indicated by solid squares.
Figure 11B:
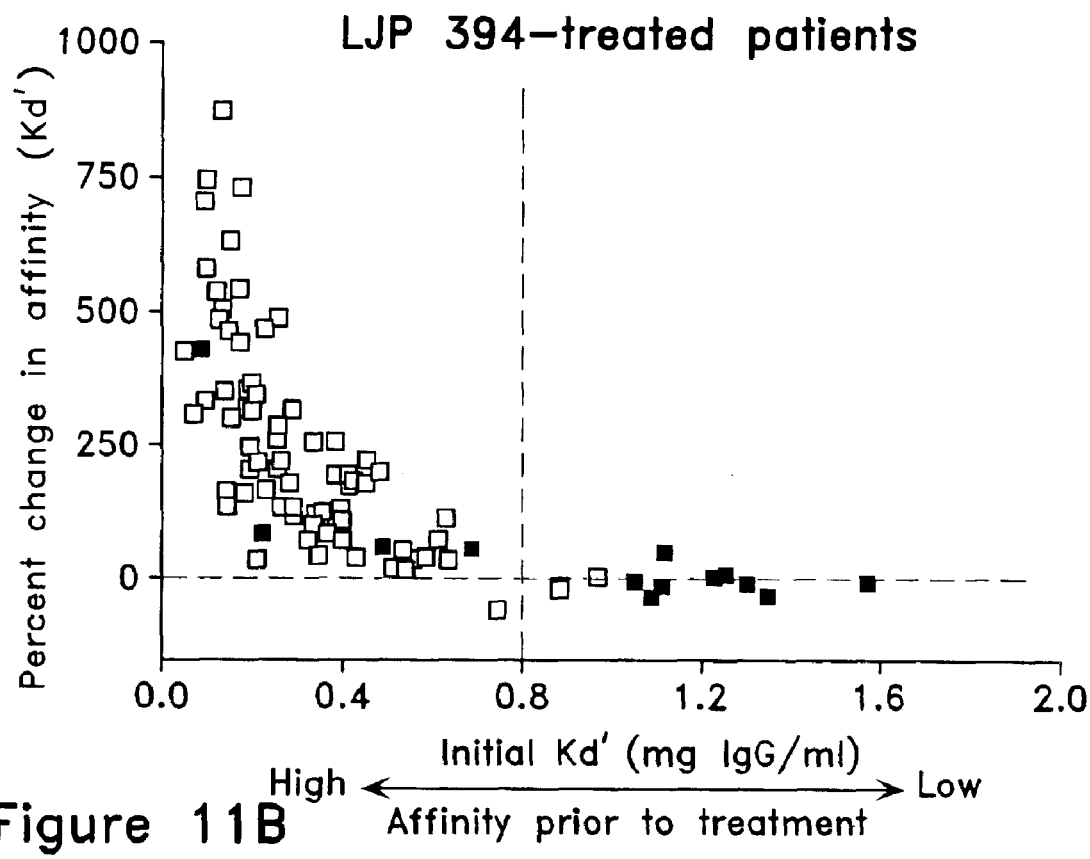
FIGS. 11B (LJP 394-treated patients) is similar to FIG. 11A except that an expanded population of patients has been used for analysis.
Figure 11C:
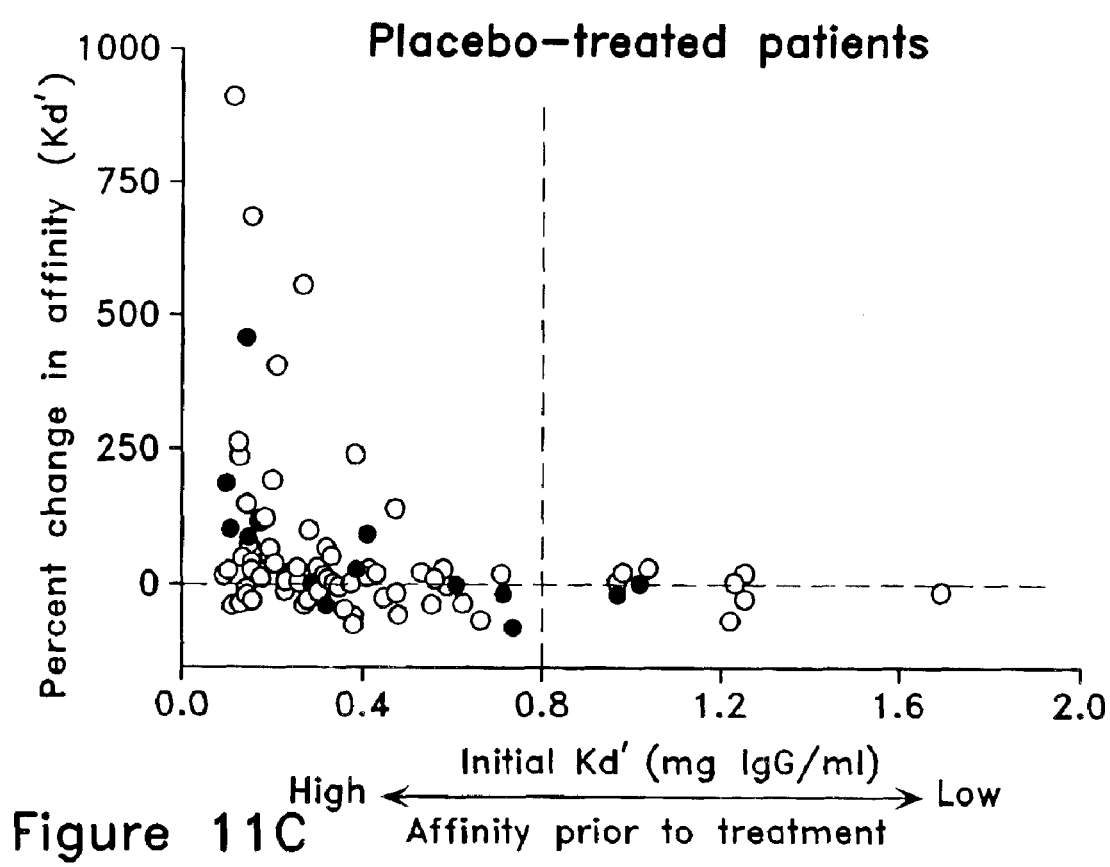
FIG. 11C depicts the percent change in Kd' for placebo-treated patients using an expanded population of patients. The patients experiencing flares are represented by solid squares for LJP 394-treated patients and solid circles for placebo-treated patients.
Figure 12:
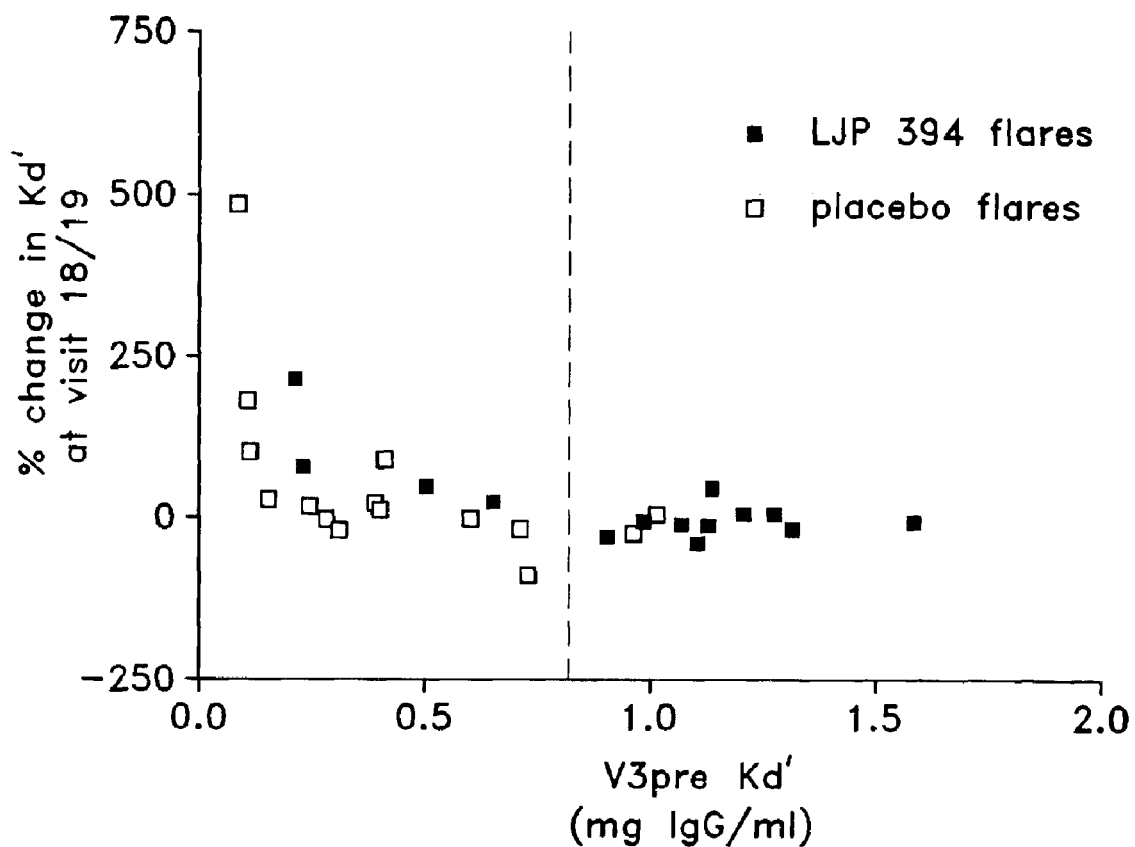
FIG. 12 is a graph depicting renal flares in patients receiving conjugate LJP 394 (solid squares) and in patients receiving placebo (open squares). Each square represents a patient. X-axis is the $K_D'$ before receiving treatment (or placebo); Y-axis is the percentage change in $K_D'$ after 4 months of treatment (or placebo).

Renal flares. FIG. 11A is similar to the graph in FIG. 5A, except that patients that presented with SLE-associated flares are identified by darkened boxes. FIGS. 11B (LJP 394-treated patients) is similar to FIG. 11A except that an expanded population of patients has been used for analysis. FIG. 11C shows the percent change in affinity for placebo-treated patients. The solid shapes (square for LJP 394-treated patients and circle for placebo-treated patients) indicate the patients who experienced renal flares during the treatment period. The clustering of lupus flares in the low affinity patients is evident in FIGS. 11 and 12. These data indicate that patients with high affinity for LJP 394 respond better to the drug by both serological and clinical measures and experienced fewer renal flares.

Figure 13:
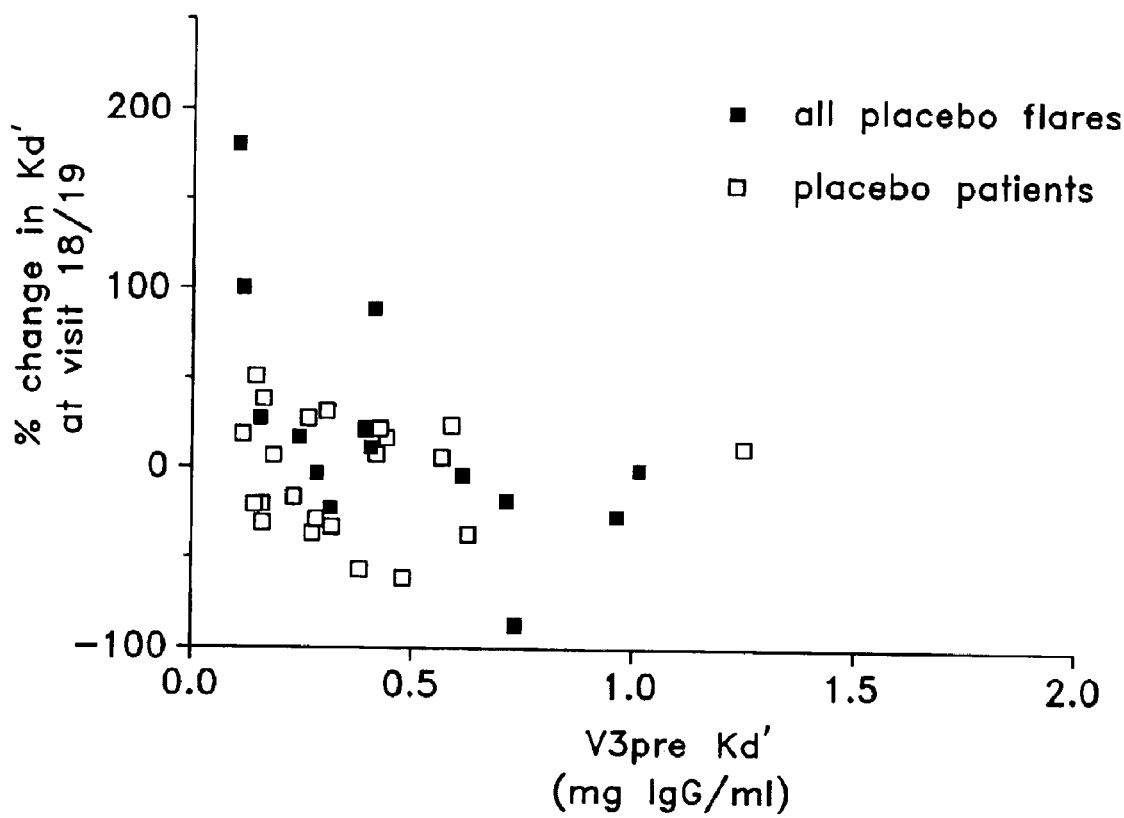
FIG. 13 is a graph depicting change in $K_D'$ in patients receiving a placebo (i.e., not receiving treatment) after four months, with solid squares indicating incidence of renal flares and open squares indicating placebo patients. The results indicate a random distribution of flares relative to initial $K_D'$ and relative to change in $K_D'$.

As indicated in FIG. 13, there appears to be no effect of placebo treatment on Kd' over 4 months of administration of placebo. While the number of data points is limited in this graph, the lack of effect of placebo treatment on Kd' is identical to the first study.

Figure 14:
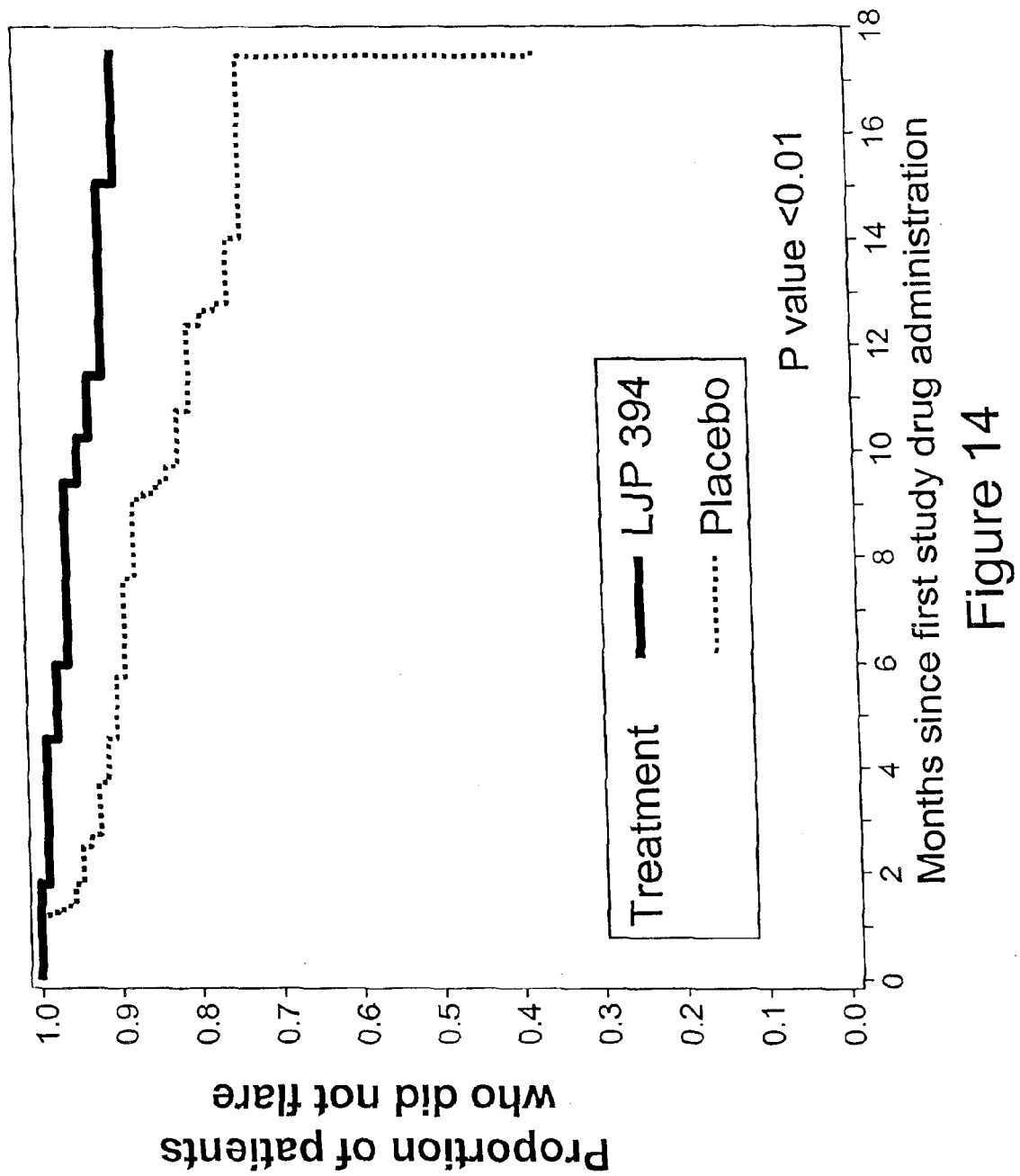
FIG. 14 is a graph depicting time to the development of renal flares for the high affinity patients. The solid line represents patients who have been treated with LJP 394 and the dotted line represents patients who have been treated with a placebo. The x-axis is the time since first dose of LJP 394 (or placebo) in months and the y-axis is the percentage of individuals that have not experienced a renal flare.

FIG. 14 depicts a renal flare analysis for high affinity individuals (Kd' of less than 0.8 mg/ml). The X-axis is time since the first dose of LJP 394 (or placebo) measured in months and wherein the Y-axis is the proportion of individuals who did not experience a renal flare. A higher proportion of high affinity patients receiving LJP 394 did not have a renal flare as compared to high affinity placebo patients. For placebo-treated patients, more flares occurred and these flares occurred earlier in the trial.

Example 4

Dependence on Corticosteroids and/or Cyclophosphamide

Figure 15:
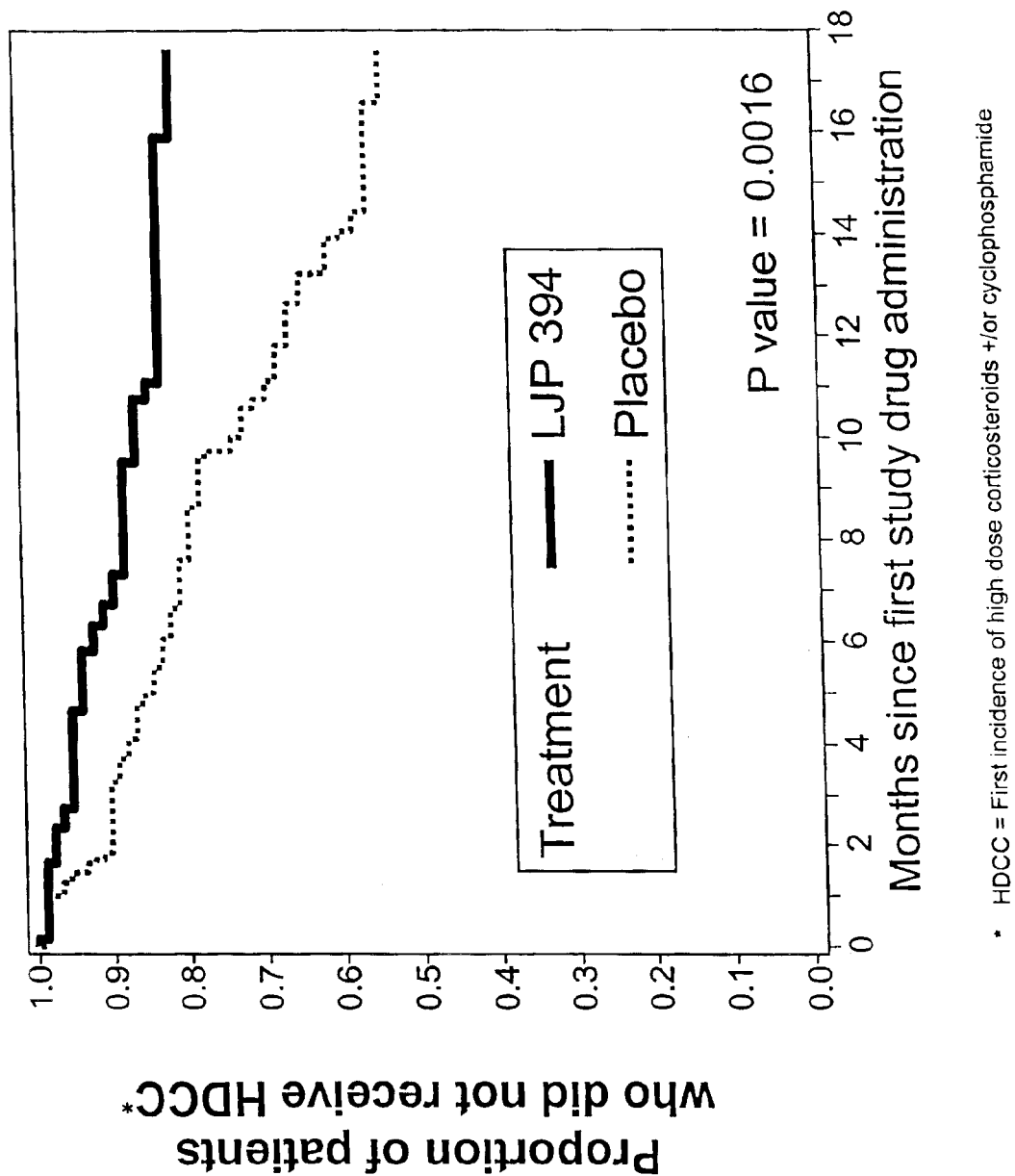
FIG. 15 is a graph depicting time to institution of high dose corticosteroids and/or cyclophosphamide (HDCC) treatment in the high affinity group. HDCC treatment is the first intervention with high dose corticosteroid and/or cyclophosphamide in the high affinity patients. The solid line represents patients treated with LJP 394 and the dotted line represents patients treated with placebo. The x-axis is the time since first dose of LJP 394 (or placebo) in months and the y-axis is the percentage of individuals that have not received HDCC intervention.

High affinity patients (Kd'<0.8 mg/ml) in study 2 (see Example 3), were analyzed in terms of time to the first intervention with high dose corticosteroid and/or cyclophosphamide (HDCC) treatment. The results of this analysis are depicted in FIG. 15. The solid line indicates the LJP 394-treated individuals while the dotted line indicates the placebo-treated individuals. The X-axis indicates time since first dose of LJP 394 (or placebo) in terms of months and the Y-axis indicates the percentage of individuals that did not receive HDCC intervention. HDCC intervention refers to the first intervention with an increased dosage of corticosteroid alone or with cyclophosphamide such that the increase dosage is at least a 15 mg/day increment and such that the total amount of corticosteroid and/or cyclophosphamide treatment is greater than 20 mg/day. HDCC may be administered using standard clinical protocols. A clinician may monitor a patient and determine when HDCC treatment is needed by evaluating factors including, but not limited to, proteinuria levels, hematuria levels, and serum creatinine levels. In general, patients who experience renal flares are given HDCC treatment. More HDCC intervention was required in high affinity placebo-treated patients than in high affinity LJP 394-treated patients and the HDCC intervention was required earlier in the patients treated with placebo.

Example 5

Use of LJP 394 Affects Clinical Outcome

Figure 16:
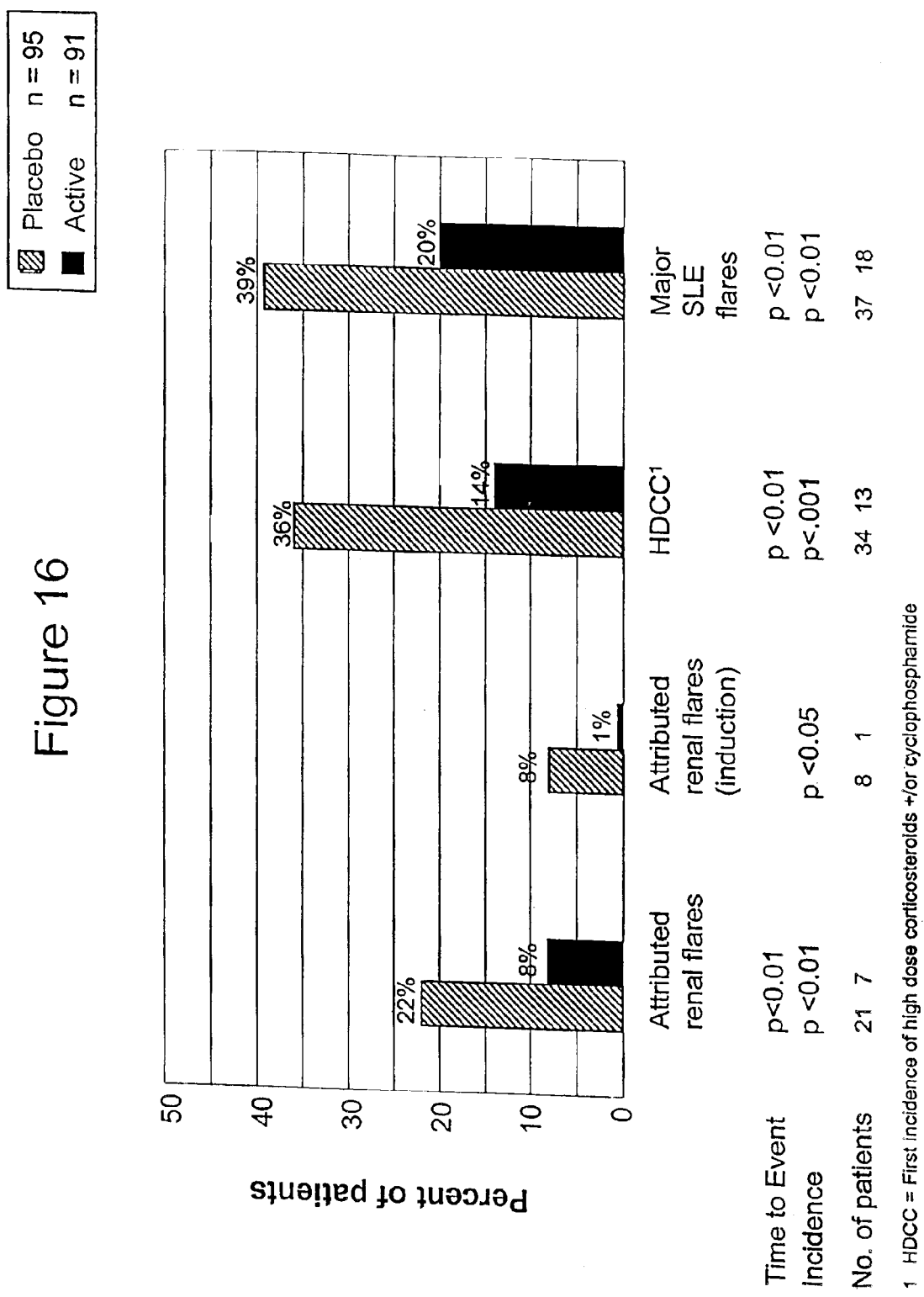
FIG. 16 is a graph depicting a summary of clinical outcomes in the high affinity group (Kd'≦0.8 mg/ml)).

Four parameters of clinical outcome: renal flares throughout the trial, renal flares during the induction period, HDCC intervention and major SLE flares, were analyzed for the high affinity group and the results are depicted in FIG. 16. The slashed bars represent high affinity placebo-treated patients and the solid bars represent LJP 394-treated high affinity (Kd'<0.8 mg/ml) patients. HDCC intervention refers to the first incidence of the administration of increased dosage corticosteroids and/or cyclophosphamide, as defined herein. Major SLE flares include hospitalization due to SLE, first occurrence of high dose prednisone, first occurrence of high dose cyclophosphamide, and/or death due to SLE. The induction period during which renal flares were measured is the first 4 months of the LJP 394 treatment at 100 mg/week (or placebo). For the duration of the treatment, after the initial induction period, there was intermittent dosing. For the non-induction period, the dosage was 50 mg/week of LJP 394 (or placebo) with periods of no treatment. FIG. 16 illustrates that high affinity patients responded significantly better to LJP 394 treatment than placebo-treated patients and that the clinical outcome of the high affinity patients is markedly better.

Figure 17:
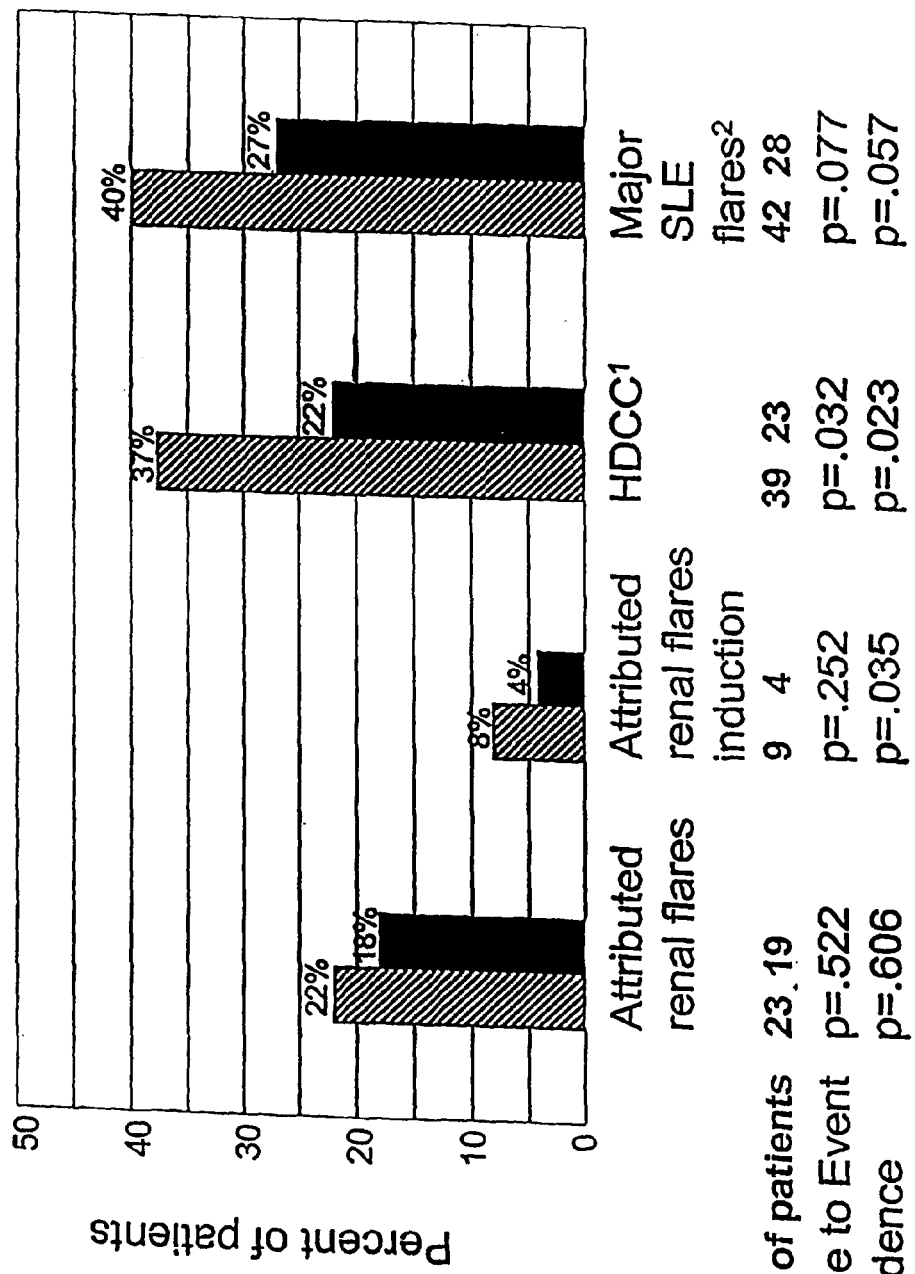
FIG. 17 is a graph depicting a summary of clinical outcomes in the entire patient population (the "intent to treat" population).

In contrast, FIG. 17 shows the entire patient population pool (i.e., the "intent to treat" population) which contains both low and high affinity patients. The LJP 394-treated patients showed some improvement in clinical outcome over the placebo-treated patients; however, the clinical outcome for this "mixed" LJP 394-treated group is not as striking compared to the results in high affinity patients (as shown in FIG. 16). Thus, the high affinity patients exhibit more positive clinical outcomes (i.e., fewer renal flares throughout the trial, fewer renal flares during the induction period, more time to HDCC intervention, and fewer major SLE flares).

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

We claim:

1. A method of treating systemic lupus erythematosus (SLE) in an individual, comprising administering to the individual a conjugate comprising (a) a non-immunogenic valency platform molecule and (b) two or more molecules comprising double stranded DNA (dsDNA) epitopes, wherein the dsDNA epitopes are polynucleotides which specifically bind to an antibody from the individual which specifically binds to double stranded DNA, wherein the polynucleotides comprise single stranded or double stranded sequences, and wherein affinity of the polynucleotides for the antibody from the individual is used as a basis for selecting the individual to receive or continue to receive the treatment, and wherein said treatment comprises administering an effective amount of said conjugate to the individual.

2. The method of claim 1, wherein the polynucleotides are double stranded DNA.

3. A method of treating SLE in an individual, comprising administering to the individual a conjugate comprising (a) a non-immunogenic valency platform molecule and (b) two or more polynucleotides which specifically bind to an antibody from the individual which specifically binds to double stranded DNA, said polynucleotides consisting essentially of the double stranded sequence 5'-GTGTGTGTGTGTGTGTGTGT-3'(SEQ ID NO:1), wherein the apparent equilibrium dissociation constant ($K_D'$) for the polynucleotides with respect to the antibody from the individual before or upon initiation of treatment is less than about 0.8 mg IgG per ml, wherein said $K_D'$ value or a functional equivalent thereof is used as a basis for selecting the individual to receive the treatment, and wherein said treatment comprises administering an effective amount of said conjugate to the individual.

4. The method of claim 3, wherein the $K_D'$ is less than about 0.5.

5. The method of claim 3, wherein the $K_D'$ is less than about 0.2.

6. The method of claim 3, wherein the platform molecule is

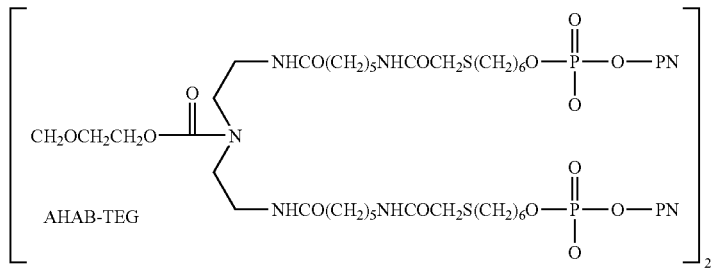

wherein PN is the polynucleotide.

7. The method of claim 6, wherein the polynucleotides consist of the double stranded sequence 5'-GTGTGTGTGTGTGTGTGTGT-3'(SEQ ID NO:1).

8. A method of treating SLE in an individual comprising:
(a) assessing affinity of an anti-double stranded DNA antibody from the individual with respect to a dsDNA epitope which is to be used in treatment, wherein the individual is selected for treatment based on said antibody affinity; and
(b) treating said selected individual by administering to said selected individual an effective amount of a conjugate comprising (i) a non-immunogenic valency platform molecule and (ii) two or more of the dsDNA epitopes, wherein the dsDNA epitopes are polynucleotides which specifically bind to an antibody from the individual which specifically binds to double stranded DNA, wherein the polynucleotides comprise single stranded or double stranded sequences.

9. The method of claim 8, wherein the platform molecule is

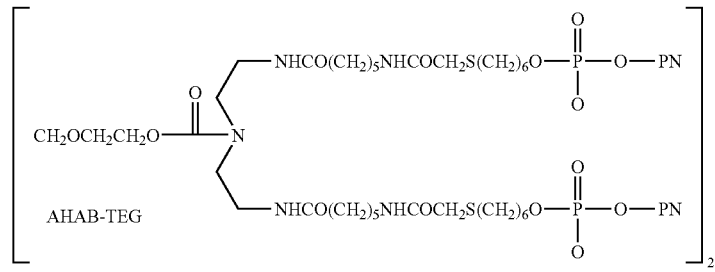

wherein PN is the polynucleotide.

10. The method of claim 8, wherein the polynucleotides are double stranded DNA.

11. A method of treating SLE in an individual, comprising
   (a) assessing before initiation of treatment an apparent equilibrium dissociation constant ($K_D'$) or a functional equivalent thereof for a polynucleotide in a conjugate and an antibody from the individual which specifically binds to double stranded DNA, said conjugate comprising (i) a non-immunogenic valency platform molecule and (ii) two or more polynucleotides which specifically bind to an antibody from the individual which specifically binds to double stranded DNA, said polynucleotides consisting essentially of the double stranded sequence 5'-GTGTGTGTGTGTGTGTGTGT-3' (SEQ ID NO: 1), wherein the individual is selected to receive the treatment if the $K_D'$ is less than about 0.8 mg IgG per ml; and
   (b) administering an effective amount of the conjugate to the selected individual in an amount sufficient to increase the $K_D'$.

12. The method of claim 11, wherein the $K_D'$ is less than about 0.5.

13. The method of claim 11, wherein the $K_D'$ is less than about 0.2.

14. The method of claim 11, wherein the platform molecule is

15. A method of treating SLE in an individual, comprising:
   (a) assessing before or upon initiation of treatment an apparent equilibrium dissociation constant ($K_D'$) for a dsDNA epitope in a conjugate and an antibody from the individual which specifically binds to double stranded DNA, said conjugate comprising (i) a non-immunogenic valency platform molecule and (ii) two or more molecules comprising said epitopes, wherein the said epitopes are polynucleotides which specifically bind to an antibody from the individual which specifically binds to double stranded DNA, wherein the polynucleotides comprise single stranded or double stranded sequences, and
   (b) administering to the individual the conjugate in an amount sufficient to increase the $K_D'$, wherein treatment is continued if $K_D'$ is increased at least about 20% compared to $K_D'$ before or upon initiation of treatment, and wherein said treatment comprises administration of an effective amount of said conjugate to the individual.

16. The method of claim 15, wherein the polynucleotides consist essentially of the double stranded sequence 5'-GTGTGTGTGTGTGTGTGTGT-3' (SEQ ID NO:1).

17. The method of claim 15, wherein the polynucleotides consist of the double stranded sequence 5'-GTGTGTGTGTGTGTGTGTGT-3' (SEQ ID NO: 1).

18. The method of claims 15, 16, or 17 wherein the treatment is continued if $K_D'$ is increased at least about 50% compared to $K_D'$ before or upon initiation of treatment.

19. The method of claims 15, 16, or 17 wherein the treatment is continued if $K_D'$ is increased at least about 100% compared to $K_D'$ before or upon initiation of treatment.

20. The method of claim 16 wherein the platform molecule is

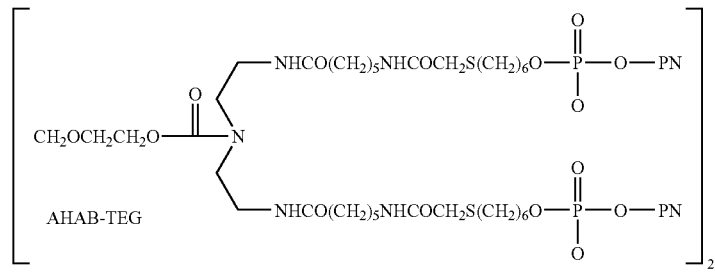

wherein PN is the nucleotide.

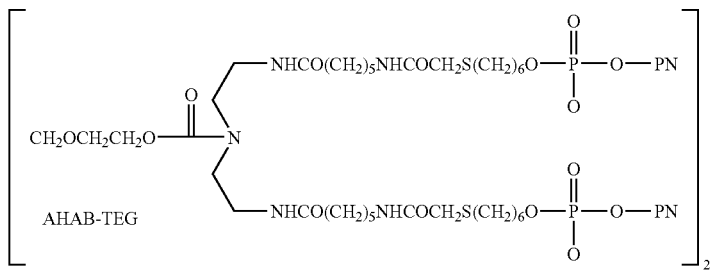

wherein PN is the polynucleotide.

21. The method of claim 1, wherein said affinity is measured by surface plasmon resonance assay.

22. The method of claim 1, wherein the polynucleotides comprise the double stranded sequence 5'-GTGTGTGTGTGTGTGTGTGT-3' (SEQ ID NO: 1).

23. The method of claim 1, wherein the polynucleotides consist essentially of the double stranded sequence 5'-GTGTGTGTGTGTGTGTGTGT-3' (SEQ ID NO1).

24. The method of claim 1, wherein the polynucleotides consist of the double stranded sequence 5'-GTGTGTGTGTGTGTGTGTGT-3' (SEQ ID NO: 1).

25. The method of claim 1, wherein the platform molecule is

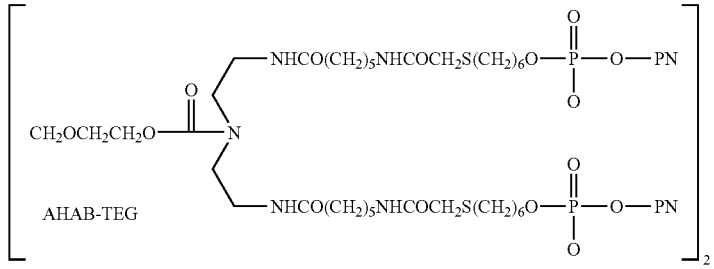

wherein PN is the polynucleotide.

26. The method of claim 25, wherein the polynucleotides comprise the double stranded sequence 5'-GTGTGTGTGTGTGTGTGTGT-3' (SEQ ID NO:1).

27. The method of claim 25, wherein the polynucleotides consist essentially of the double stranded sequence 5'-GTGTGTGTGTGTGTGTGTGT-3' (SEQ ID NO: 1).

28. The method of claim 25, wherein the polynucleotides consist of the double stranded sequence 5'-GTGTGTGTGTGTGTGTGTGT-3' (SEQ ID NO: 1).

29. The method of claim 3, wherein the $K_D'$ value is measured by surface plasmon resonance assay.

30. The method of claim 3, wherein the conjugate comprises four polynucleotides consisting essentially of the double stranded sequence 5'-GTGTGTGTGTGTGTGTGTGT-3' (SEQ ID NO: 1).

31. The method of claim 3, wherein the conjugate comprises four polynucleotides consisting of the double stranded sequence 5'-GTGTGTGTGTGTGTGTGTGT-3' (SEQ ID NO:1).

32. The method of claim 8, wherein said antibody affinity is measured by surface plasmon resonance assay.

33. The method of claim 8, wherein the polynucleotides comprise the double stranded sequence 5'-GTGTGTGTGTGTGTGTGTGT-3' (SEQ ID NO: 1).

34. The method of claim 8, wherein the polynucleotides consist essentially of the double stranded sequence 5'-GTGTGTGTGTGTGTGTGTGT-3' (SEQ ID (NO: 1).

35. The method of claim 8, wherein the polynucleotides consist of the double stranded sequence 5'-GTGTGTGTGTGTGTGTGTGT-3' (SEQ ID NO: 1).

36. The method of claim 9, wherein the polynucleotides comprise the double stranded sequence 5'-GTGTGTGTGTGTGTGTGTGT-3' (SEQ ID NO: 1).

37. The method of claim 9, wherein the polynucleotides consist essentially of the double stranded sequence 5'-GTGTGTGTGTGTGTGTGTGT-3' (SEQ ID NO:1).

38. The method of claim 9, wherein the polynticleotides consist of the double stranded sequence 5'-GTGTGTGTGTGTGTGTGTGT-3' (SEQ ID NO: 1).

39. The method according of claim 11, wherein the $K_D'$ value is measured by surface plasmon resonance assay.

40. The method of claim 11, wherein the conjugate comprises four polynucleotides consisting essentially of the double stranded sequence 5'-GTGTGTGTGTGTGTGTGTGT-3' (SEQ ID NO: 1).

41. The method of claim 11, wherein the conjugate comprises four polynucleotides consisting of the double stranded sequence 5'-GTGTGTGTGTGTGTGTGTGT-3' (SEQ ID NO: 1).

42. The method of claim 14, wherein the polynucleotides consist essentially of the double stranded sequence 5'-GTGTGTGTGTGTGTGTGTGT-3' (SEQ ID NO: 1).

43. The method of claim 14, wherein the polynucleotides consist of the double stranded sequence 5'-GTGTGTGTGTGTGTGTGTGT-3' (SEQ ID NO: 1).

44. The method of claim 15, wherein the $K_D'$ value is measured by surface plasmon resonance assay.

45. The method of claim 15, wherein the conjugate comprises four polynucleotides comprising the double stranded sequence 5'-GTGTGTGTGTGTGTGTGTGT-3' (SEQ ID NO: 1).

46. The method of claim 20, wherein the polynucleotides consist of the double stranded sequence 5'-GTGTGTGTGTGTGTGTGTGT-3' (SEQ ID NO: 1).

47. The method of claim 1, wherein the individual is a human.

48. The method of claim 3, wherein the individual is a human.

49. The method of claim 8, wherein the individual is a human.

50. The method of claim 11, wherein the individual is a human.

51. The method of claim 15, wherein the individual is a human.

52. The method of claim 1, wherein said polynucleotides comprise single stranded sequences.

53. The method of claim 1, wherein said polynucleotides comprise double stranded sequences.

54. The method of claim 2, wherein said double stranded DNA comprises the sequence 5'-GTGTGTGTGTGTGTGTGTGT-3' (SEQ ID NO: 1).

55. The method of claim 2, wherein said double stranded DNA consists essentially of the sequence 5'-GTGTGTGTGTGTGTGTGTGT-3' (SEQ ID NO: 1).

56. The method of claim 2, wherein said double stranded DNA consists of the sequence 5'-GTGTGTGTGTGTGTGTGTGT-3' (SEQ ID NO: 1).

57. The method of claim 8, wherein said polynucleotides comprise single stranded sequences.

58. The method of claim 8, wherein said polynucleotides comprise double stranded sequences.

59. The method of claim 10, wherein said double stranded DNA comprises the sequence 5'-GTGTGTGTGTGTGTGTGTGT-3' (SEQ ID NO: 1).

60. The method of claim 10, wherein said double stranded DNA consists essentially of the sequence 5'-GTGTGTGTGTGTGTGTGTGT-3' (SEQ ID NO: 1).

61. The method of claim 10, wherein said double stranded DNA consists of the sequence 5'-GTGTGTGTGTGTGTGTGTGT-3' (SEQ ID NO: 1).

62. The method of claim 15, wherein said polynucleotides comprise single stranded sequences.

63. The method of claim 15, wherein said polynucleotides comprise double stranded sequences.

64. The method of claim 54, wherein the apparent equilibrium dissociation constant ($K_D'$) for the double stranded DNA with respect to the antibody from the individual before or upon initiation of treatment is less than about 0.8 mg IgG per ml, wherein said $K_D'$ value or a functional equivalent thereof is used as a basis for selecting the individual to receive the treatment.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
gtgtgtgtgt gtgtgtgtgt                                       20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
cacacacaca cacacacaca                                       20